(12) United States Patent
Combs et al.

(10) Patent No.: US 9,034,341 B2
(45) Date of Patent: May 19, 2015

(54) CONTROL OF RAGE FUSION PROTEIN GLYCOSYLATION AND RAGE FUSION PROTEIN COMPOSITIONS

(75) Inventors: Rodney G. Combs, Wildwood, MO (US); Susanna Roe, Wentzville, MO (US); Derrick L. Ruble, Wentzville, MO (US)

(73) Assignee: TransTech Pharma, LLC, High Point, NC (US)

( * ) Notice: Subject to any disclaimer, the term of this patent is extended or adjusted under 35 U.S.C. 154(b) by 0 days.

(21) Appl. No.: 13/265,132

(22) PCT Filed: Apr. 15, 2010

(86) PCT No.: PCT/IB2010/051650
§ 371 (c)(1),
(2), (4) Date: Oct. 18, 2011

(87) PCT Pub. No.: WO2010/122460
PCT Pub. Date: Oct. 28, 2010

(65) Prior Publication Data
US 2012/0039908 A1 Feb. 16, 2012

Related U.S. Application Data

(60) Provisional application No. 61/170,897, filed on Apr. 20, 2009.

(51) Int. Cl.
| | | |
|---|---|---|
| *A61K 39/00* | (2006.01) | |
| *C07K 14/705* | (2006.01) | |
| *C12P 21/00* | (2006.01) | |
| *C07K 16/42* | (2006.01) | |

(52) U.S. Cl.
CPC ......... *C07K 14/70503* (2013.01); *C12P 21/005* (2013.01); *C07K 2317/41* (2013.01); *C07K 16/4291* (2013.01); *C07K 2317/515* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,867,973 A | 9/1989 | Goers et al. |
| 5,567,677 A | 10/1996 | Castensson et al. |
| 5,656,261 A | 8/1997 | Cerami et al. |
| 5,658,570 A | 8/1997 | Newman et al. |
| 5,714,350 A | 2/1998 | Co et al. |
| 5,747,035 A | 5/1998 | Presta et al. |
| 5,843,725 A | 12/1998 | Sledziewski et al. |
| 5,853,703 A | 12/1998 | Cerami et al. |
| 5,864,018 A | 1/1999 | Morser et al. |
| 5,891,341 A | 4/1999 | Li et al. |
| 6,007,865 A | 12/1999 | Cerami et al. |
| 6,018,026 A | 1/2000 | Sledziewski et al. |
| 6,165,476 A | 12/2000 | Strom et al. |
| 6,225,448 B1 | 5/2001 | Tao et al. |
| 6,267,958 B1 | 7/2001 | Andya et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,350,861 B1 | 2/2002 | Co et al. |
| 6,380,165 B1 | 4/2002 | Al-Abed et al. |
| 6,440,749 B1 | 8/2002 | Cerami et al. |
| 6,465,422 B1 | 10/2002 | Schmidt et al. |
| 6,555,340 B1 | 4/2003 | Schmidt et al. |
| 6,555,651 B2 | 4/2003 | Stern et al. |
| 6,563,015 B1 | 5/2003 | Stern et al. |
| 6,670,136 B2 | 12/2003 | Schmidt et al. |
| 6,677,299 B2 | 1/2004 | Stern et al. |
| 6,753,150 B2 | 6/2004 | Schmidt et al. |
| 6,761,888 B1 | 7/2004 | Schenk |
| 6,790,443 B2 | 9/2004 | Stern et al. |
| 6,825,164 B1 | 11/2004 | Stern et al. |
| 6,908,741 B1 | 6/2005 | Shahbaz |
| 6,939,545 B2 | 9/2005 | Jacobs et al. |
| 6,946,277 B2 | 9/2005 | Khowala et al. |
| 6,998,125 B2 | 2/2006 | Hanna et al. |
| 7,026,444 B2 | 4/2006 | Schmidt et al. |
| 7,081,241 B1 | 7/2006 | Schmidt et al. |
| 7,101,838 B2 | 9/2006 | Stern et al. |
| 7,125,675 B2 | 10/2006 | Schmidt et al. |
| 7,189,830 B2 | 3/2007 | Gillies et al. |
| 7,258,857 B2 | 8/2007 | Stern et al. |
| 7,470,521 B2 | 12/2008 | O'Keefe et al. |
| 7,901,688 B2 | 3/2011 | Mjalli et al. |
| 7,981,423 B2 | 7/2011 | Mjalli et al. |
| 7,981,424 B2 | 7/2011 | Mjalli et al. |
| 8,344,120 B2 | 1/2013 | Mjalli et al. |

(Continued)

FOREIGN PATENT DOCUMENTS

| | | |
|---|---|---|
| EP | 0417563 | 8/1990 |
| EP | 0417014 | 10/1990 |

(Continued)

OTHER PUBLICATIONS

Ding et al., J Biol Chem. Oct. 13, 1995;270(41):24580-4.*
Osawa et al., Biochim Biophys Acta. Oct. 2007;1770(10):1468-74. Epub Jul. 19, 2007.*
Hossler et al., Glycobiology. Sep. 2009;19(9):936-49. doi: 10.1093/glycob/cwp079. Epub Jun. 3, 2009.*
Srikrishna et al., "N-Glycans on the Receptor for Advanced Glycation End Products Influence Amphoterin Binding and Neurite Outgrowth," Journal of Neurochemistry, 80:998-1008 (2002).

(Continued)

*Primary Examiner* — Michael Szperka
(74) *Attorney, Agent, or Firm* — Samuel B. Rollins

(57) ABSTRACT

The invention relates to methods for controlling the glycosylation of a RAGE fusion protein. The invention also relates to compositions comprising an amount of a RAGE fusion protein where at least 0.5% of the amount of the RAGE fusion protein is aglycosylated and wherein no more than 53.2% of the amount of the RAGE fusion protein is aglycosylated.

14 Claims, 28 Drawing Sheets

(56) References Cited

U.S. PATENT DOCUMENTS

| | | |
|---|---|---|
| 2001/0039256 A1 | 11/2001 | Stern et al. |
| 2001/0053357 A1 | 12/2001 | Stern et al. |
| 2002/0002203 A1 | 1/2002 | Rahbar |
| 2002/0006391 A1 | 1/2002 | Smith et al. |
| 2002/0013256 A1 | 1/2002 | Rahbar et al. |
| 2002/0022234 A1 | 2/2002 | Al-Abed et al. |
| 2002/0037496 A1 | 3/2002 | Jacobson et al. |
| 2002/0077293 A1 | 6/2002 | Cahoon et al. |
| 2002/0082273 A1 | 6/2002 | Bush et al. |
| 2002/0086282 A1 | 7/2002 | Pillarisetti et al. |
| 2002/0102604 A1 | 8/2002 | Edwards et al. |
| 2002/0106726 A1 | 8/2002 | Schmidt et al. |
| 2002/0116725 A1 | 8/2002 | Stern et al. |
| 2002/0122799 A1 | 9/2002 | Stern et al. |
| 2002/0148009 A1 | 10/2002 | Khowala et al. |
| 2003/0144201 A1 | 7/2003 | Tracey et al. |
| 2004/0121372 A1 | 6/2004 | Schmidt et al. |
| 2004/0142382 A1 | 7/2004 | Veldman et al. |
| 2004/0142391 A1 | 7/2004 | Schmidt et al. |
| 2004/0228855 A1 | 11/2004 | Stern et al. |
| 2005/0008649 A1 | 1/2005 | Shin et al. |
| 2005/0026811 A1 | 2/2005 | Mjalli et al. |
| 2005/0033017 A1 | 2/2005 | Yamamoto et al. |
| 2005/0129682 A1 | 6/2005 | Schmidt et al. |
| 2005/0170382 A1 | 8/2005 | Stern et al. |
| 2005/0244849 A1 | 11/2005 | Pittman et al. |
| 2006/0024298 A1* | 2/2006 | Lazar et al. ............... 424/133.1 |
| 2006/0030527 A1 | 2/2006 | Mjalli et al. |
| 2006/0057679 A1 | 3/2006 | O'Keefe et al. |
| 2006/0078562 A1 | 4/2006 | Mjalli et al. |
| 2006/0084145 A1 | 4/2006 | Anderson et al. |
| 2006/0140933 A1 | 6/2006 | Pittman et al. |
| 2007/0014791 A1 | 1/2007 | Schmidt et al. |
| 2007/0099829 A1 | 5/2007 | Stern et al. |
| 2007/0167360 A1 | 7/2007 | Yan et al. |
| 2008/0019986 A1 | 1/2008 | Stern et al. |
| 2008/0045455 A1 | 2/2008 | Mjalli et al. |
| 2008/0075733 A1 | 3/2008 | Mjalli et al. |
| 2008/0171701 A1 | 7/2008 | Stern |
| 2008/0199467 A1 | 8/2008 | Mjalli et al. |
| 2008/0207499 A1 | 8/2008 | Barile |
| 2008/0214453 A1 | 9/2008 | Stern et al. |
| 2009/0004190 A1 | 1/2009 | Mjalli et al. |
| 2009/0060925 A1 | 3/2009 | Mjalli et al. |
| 2011/0124102 A1 | 5/2011 | Mjalli et al. |
| 2011/0244516 A1 | 10/2011 | Mjalli et al. |

FOREIGN PATENT DOCUMENTS

| | | |
|---|---|---|
| EP | 1 380 593 | 1/2004 |
| RU | 2219947 | 12/2003 |
| WO | WO 94/10308 | 5/1994 |
| WO | WO 97/26913 | 7/1997 |
| WO | WO 97/39121 | 10/1997 |
| WO | WO 97/39125 | 10/1997 |
| WO | WO 98/22138 | 5/1998 |
| WO | WO 98/40071 | 9/1998 |
| WO | WO 99/07402 | 2/1999 |
| WO | WO 99/13912 | 3/1999 |
| WO | WO 99/18987 | 4/1999 |
| WO | WO 99/45907 | 9/1999 |
| WO | WO 99/54485 | 10/1999 |
| WO | WO 00/18970 | 4/2000 |
| WO | WO 00/20458 | 4/2000 |
| WO | WO 00/20621 | 4/2000 |
| WO | WO 01/05422 | 1/2001 |
| WO | WO 01/12598 | 2/2001 |
| WO | WO 01/18060 | 3/2001 |
| WO | WO 01/29269 | 4/2001 |
| WO | WO 01/76584 | 10/2001 |
| WO | WO 01/79849 | 10/2001 |
| WO | WO 01/86002 | 11/2001 |
| WO | WO 01/92210 | 12/2001 |
| WO | WO 01/92892 | 12/2001 |
| WO | WO 02/14519 | 2/2002 |
| WO | WO 02/30889 | 4/2002 |
| WO | WO 02/066978 | 8/2002 |
| WO | WO 02/068636 | 9/2002 |
| WO | WO 2004/004661 | 1/2004 |
| WO | 2004/016229 | 2/2004 |
| WO | WO 2004016229 A2 * | 2/2004 |
| WO | WO 2004/055055 | 7/2004 |
| WO | 2004/099231 | 11/2004 |
| WO | WO 2005/019429 | 3/2005 |
| WO | WO 2005/049852 | 6/2005 |
| WO | WO 2005/051995 | 6/2005 |
| WO | WO 2005/061538 | 7/2005 |
| WO | WO 2005/108584 | 11/2005 |
| WO | WO 2006/002971 | 1/2006 |
| WO | 2006/017643 | 2/2006 |
| WO | 2006/017647 | 2/2006 |
| WO | WO 2006/012373 | 2/2006 |
| WO | WO 2006/012415 | 4/2006 |
| WO | WO 2006/036922 | 4/2006 |
| WO | WO 2006/119510 | 11/2006 |
| WO | 2007/094926 | 8/2007 |
| WO | 2007/130302 | 11/2007 |
| WO | WO 2007130302 A2 * | 11/2007 |
| WO | 2008/055260 | 5/2008 |
| WO | 2008/100470 | 8/2008 |
| WO | 2008/100670 | 8/2008 |
| WO | 2008/157378 | 12/2008 |
| WO | 2009/004190 | 1/2009 |
| WO | 2008/123999 | 10/2009 |

OTHER PUBLICATIONS

Taguchi et al., "Blocking of RAGE—Amphoterin Signaling Suppresses Tumour Growth and Metastases," Nature, 405:354-360.

Tao and Morrison, "Studies of Aglycosylated Chimeric Mouse-Human IgG Role of Carbohydrate in the Structure and Effector Functions Mediated by the Human IgG Constant Region," The Journal of Immunology, 143(8)2595-2601.

Taylor and Wall, "Selective Removal of α Heavy-Chain Glycosylation Sites Causes Immunoglobulin A Degradation and Reduced Secretion," Molecular and Cellular Biology, 8(10):4197-4203 (1988).

Teillet et al., "Food Restriction Prevents Advanced Glycation End Product Accumulation and Retards Kidney Aging in Lean Rats," J. Am. Soc. Nephrol., 11:1488-1497 (2000).

Terman et al., "Identification of a New Endothelial Cell Growth Factor Receptor Tyrosine Kinase," Oncogene, 6:1677-1683 (1991).

Ullrich and Schlessinger, et al., "Signal Transduction by Receptors with Tyrosine Kinase Activity," Cell, 61:203-212 (1990).

Vlassara, "Advanced Glycation End-products and Atherosclerosis," The Finnish Medical Society DUODECIM, Ann. Med., 28:419-246 (1996).

Wallick et al., "Glycosylation of a VH Residue of a Monoclonal Antibody Against α(1→6) Dextran Increases its Affinity for Antigen," J. Exp. Med. 168:1099-1109 (1988).

Wautier et al., "Receptor-Mediated Endothelial Cell Dysfunction in Diabetic Vasculopathy, Soluble Receptoir for Advanced Glycation End Products Blocks Hyperpermeability in Diabetic Rats," J. Clin. Invest. 97(1):238-243 (1996).

Wilton et al., "Expression and Purification of Recombinant Human Receptor for Advanced Glycation Endproducts in *Escherichia coli*," Protein Expression and Purification, 47:25-35 (2006).

Wright et al., "Antibody Variable Region Glycosylation: Position Effects on Antigen Binding and Carbohydrate Structure," The EMBO Journal, 10(10):2717-2723 (1991).

Yan, "RAGE and Amyloid-β Peptide Neurotoxicity in Alzheimer's Disease," Nature, 392:685-691 (1996).

Yarden and Ullrich, "Growth Factor Receptor Tyrosine Kinases," Ann. Rev. Biochem. 57:443-478 (1988).

Yonekura et al., "Novel Splice Variants of the Receptor for Advanced Glycation End-products Expressed in Human Vascular Endothelial Cells and Pericytes, and their Putative Roles in Diabetes-Induced Vascular Injury," Biochem. J. 370:1097-1109 (2003).

International Search Report in PCT/IB2010/051650 (Apr. 15, 2010).

International Preliminary Report on Patentability (Oct. 25, 2011).

(56) References Cited

OTHER PUBLICATIONS

Written Opinion of the International Search Authority (Oct. 25, 2011).
Recombinant Human RAGE Fc Chimera, Catalog No. 1145-RG. R&D Systems, Jul. 22, 2009.
Recombinant Mouse RAGE Fc Chimera, Catalog No. 1179-RG. R&D Systems, Nov. 5, 2009.
Recombinant Rat RAGE Fc Chimera, Catalog No. 1616-RF. R&D Systems, Jun. 2, 2010.
Ayoubi et al., "Production of Recombinant Proteins in Chinese Hamster Ovary Cells Overexpressing the Subtilisin-like Proprotein Converting Enzyme Furin," Molecular Biology Reports, 23:87-95 (1996).
Brownlee et al., "Advanced Glycosylation End Products in Tissue and the Biochemical Basis of Diabetic Complications," The New England Journal of Medicine, 318:1315-1321 (1988).
Bucciarelli et al., "RAGE is a Multiligand Receptor of the Immunoglobulin Superfamily: Implications for Homeostasis and Chronic Disease," Cell. Mol. Life Sci., 59:1117-1128 (2002).
Chavakis et al., "RAGE (receptor for advanced glycation end products): a Central Player in the Inflammatory Response," Microbes and Infection 6:1219-1225 (2004).
Chen et al., "Non-Glycosylated Human B7-1(CD80) Retains the Capacity to Bind its Counter-Receptors," FEBS Letters, 428:127-134 (1998).
Cruz et al., "Metabolic Shifts by Nutrient Manipulation in Continuous Cultures of BHK Cells," Biotechnology and Bioengineering, 66(2):104-113 (1999).
Dattilo et al., "The Extracellular Region of the Receptor for Advanced Glycation End Products is Composed of Two Independent Structual Units," Biochemistry, 46:6957-6970 (2007).
DeVries et al., "The fms-Like Tyrosine Kinase, a Receptor for Vascular Endothelial Growth Factor," Science, 255:989-991 (1992).
Ding et al., "N-Glycosylation of the Human Granulocyte-Macrophage Colony-Stimulating Factor Receptor Alpha Subunit is Essential for Ligand Binding and Signal Transduction," The Journal of Biological Chemistry, 270 (41):24580-24584 (1995).
Donadel et al., "Human Polyreactive and Monoreactive Antibodies: Effect of Glycosylation on Antigen Binding," Glycobiology, 4(4):491-496 (1994).
Drews, "Genomic Sciences and the Medicine of Tomorrow," Nature Biotechnology, 14:1516-1518 (1996).
Elbein, "Inhibitors of Glycoprotein Synthesis," Methods in Enzymology, 98:135-154 (1985).
Elbein, "Inhibitors of the Biosynthesis and Processing of N-Linked Oligosaccharide Chains," Ann. Rev. Biochem., 56:497-534 (1987).
Frost et al., "Glycosylation of High-Affinity Thrombin Receptors Appears Necessary for Thrombin Binding," Biochemical and Biophysical Research Communications, 180(1):349-355 (1991).
Gorczyca et al., "Effect of Glycosylation Inhibitors on Binding Properties of the Fcγ Receptors from Guinea Pig Peritoneal Macrophages," Acta Biochemica Polonica, 38(1):135-137 (1991).
Hammes et al., "Diabetic Retinopathy Risk Correlates with Intracellular Concentrations of the Glycoxidation Product Nε-(carboxymethyl) Lysine Independently of Glycohaemoglobin Concentrations," Diabetologia, 42:603-607 (1999).
Hanford et al., "Purification and Characterization of Mouse Soluble Receptor for Advanced Glycation End Products (sRAGE)," The Journal of Biological Chemistry, 279(48):50019-50024 (2004).
Henning et al., "Influence of Glycosylation Inhibitors on Dihydropyridine Binding to Cardiac Cells," Molecular and Cellular Biochemistry, 160/161:47-52 (1996).
Herz et al., "Proteolytic Processing of the 600 kd Low Density Lipoprotein Receptor-Related Protein (LRP) Occurs in a Trans-Golgi Compartment," The EMBO Journal, 9(6):1769-1776 (1990).
Hofman et al., "RAGE Mediates a Novel Proinflammatory Axis: A Central Cell Surface Receptor for S100/Calgranulin Polypeptides," Cell, 97:889-901 (1999).
Hudson et al., "Blockade of Receptor for Advanced Glycation Endproducts: A New Target for Therapeutic Intervention in Diabetic Complications and Inflammatory Disorders," Archives of Biochemistry and Biophysics, 419:80-88 (2003).
Hudson and Schmidt, "RAGE: A Novel Target for Drug Intervention in Diabetic Vascular Disease," Pharmaceutical Research, 21(7):1079-1086 (2004).
Koch et al., "A Secreted Soluble Form of ApoE Receptor 2 Acts as a Dominant-Negative Receptor and Inhibits Reelin Signaling," The EMBO Journal, 21(22):5996-6004 (2002).
Kokkola et al., "RAGE is the Major Receptor for the Proinflammatory Activity of HMGB1 in Rodent Macrophages," Scandinavian Journal of Immunology, 61:1-9 (2005).
Leatherbarrow et al., "Effector Functions of a Monoclonal Aglycosylated Mouse IgG2a: Binding and Activation of Complement Component C1 and Interaction with Human Monocyte Fc Receptor," Molecular Immunology, 22 (4):407-415 (1985).
Luhrs, The Role of Glycosylation in the Biosynthesis and Acquisition of Ligand-Binding Activity of the Folate-Binding Protein in Cultured KB Cells, Blood, 77(6):1171-1180 (1991).
Medzihradszky, "Characterization of Protein and Glycoconjugates," Methods in Enzymology, 405:116-138 (2005).
Mulligan and Rees, "Chimaeric Gα Proteins: Their Potential Use in Drug Discovery," TiPS, 20:118-124 (1999).
Muraoka and Shulman, "Structural Requirements for IgM Assembly and Cytolytic Activity," 142(2):695-701 (1989).
Mustinen and Alitalo, "Endothelial Receptor Tyrosine Kinases Involved in Angiogenesis," The Journal of Cell Biology, 129(4):895-898 (1995).
Neeper et al., "Cloning and Expression of a Cell Surface Receptor for Advanced Glycosylation End Products of Proteins," The Journal of Biological Chemistry, 267(21):14998-15004 (1992).
Osawa et al., "De-N-Glyosylation or G82S Mutation of RAGE Sensitizes its Interaction with Advanced Glycation Endproducts," Biochimica et Biophysica Acta, 1770:1468-1474 (2007).
Ostendorp et al., "Expression and Purification of the Soluble Isoform of Human Receptor for Advanced Glycation End Products (sRAGE) from *Pichia pastoris*," Biochemical and Biophysical Research Communications, 347:4-11 (2006).
Ostendorp et al., "Structural and Functional Insights into RAGE Activation by Multimeric S100B," The EMBO Journal, 26:3868-3878 (2007).
Park et al., "Suppression of Accelerated Diabetic Atherosclerosis by the Soluble Receptor for Advanced Glycation Endproducts," Nature Medicine, 4(9):1025-1031 (1998).
Peter-Katalinic, "Methods in Enzymology:O-Glycosylation of Proteins," Methods in Enzymology, 405:139-171 (2005).
Ramasamy et al., "Advanced Glycation End Products and RAGE: A Common Thread in Aging, Diabetes, Neurodegeneration, and Inflammation," Glycobiology, 15(7):16R-28R (2005).
Riechmann et al., "Reshaping Human Antibodies for Therapy," Nature, 332:323-327 (1988).
Rocken et al., "Advanced Glycation End Products and Receptor for Advanced Glycation End Products in AA Amyloidosis," Americal Journal of Pathology, 162(4):1213-1220 (2003).
Sato et al., "Distinct Roles of the Receptor Tyrosine Kinases Tie-1 and Tie-2 in Blood Vessel Formation," Nature, 376:70-74 (1995).
Schmidt et al., Cellular Receptors for Advanced Glycation End Product, Arteriosclerosis and Thrombosis, 14 (10):1521-1528 (1994).
Schmidt et al., "Activation of Receptor for Advanced Glycation End Products: A Mechanism for Chronic Vascular Dysfunction in Diabetic Vasculopathy and Atherosclerosis," Circulation Research, 84(5):489-497 (1999).
Schmidt and Stern, "RAGE: A New Target for the Prevention and Treatment of the Vascular and Inflammatory Complication of Diabetes," TEM, 11(9):368-375 (2000).
Schmidt et al., "The Multiligand Receptor RAGE as a Progression Factor Amplifying Immune and Inflammatory Responses," the Journal of Clinical Investigation, 108(7):949-955 (2001).
Shibuya et al., "Nucleotide Sequence and Expression of a Novel Human Receptor-Type Tyrosine Kinase Gene (flt) Closely Related to the fms Family," Oncogene, 5:519-524 (1990).
Sox and Hood, "Attachment of Carbohydrate to the Variable Region of Myeloma Immunoglobulin Light Chains," Proceedings of the National Academy of Sciences, 66(3):975-982 (1970).

(56) References Cited

OTHER PUBLICATIONS

"Recombinant Human RAGE/Fc Chimera," R&D Systems, Inc., Catalog Number: 1145-RG, Mar. 5 (2004).
Arancio, O. et al., RAGE potentiates A-beta-induced Perturbation of Neuronal Function in Transgenic Mice, EMBO Journal, Vo. 23, pp. 4096-4105, 2004.
Armour, K.L. et al., "The contrasting IgG-binding interaction of human and herpes simplex virus Fc receptors," Biochemical Society Transactions, 2002, 30:495-500.
Ausubel, F. et al., Short Protocols of Molecular Biology, 4th Edition, Chapter 2, 1999.
Bin Zhou, et al., "TTP4000, a Soluble Fusion Protein Inhibitor of Receptor for Advanced Glycation End Products (RAGE) is an Effective Therapy in Animal Models of Alzheimer's Disease" Experimental Biology 2013: Biochemistry and Molecular Biology Section, Apr. 22, 2013.
Bin Zhou, et al., "TTP4000, a Soluble Fusion Protein Inhibitor of Receptor for Advanced Glycation End Products (RAGE) is an Effective Therapy in Animal Models of Alzheimer's Disease," FASEB J (Meeting Abstract Supplement) Apr. 9, 2013 27:803.1.
Bleck, G., "An Alternative Method for the Rapid Generation of Stable, High Expressing Mammalism Cell Lines," BioProcessing Journal, Sep./Oct. 2005, pp. 1-7.
Bonnardel-Phu, E. et al., Acute Modulation of Albumin Microvascular Leakage by Advanced Glycation Ends Products in Microcirculation of Diabetic Rats in Vivo, Diabetes, vol. 48, pp. 2052-2058, 1999.
Bucciarelli, L., RAGE Blockage Stabilizes established Atherosclerosis in Diabetic Apolipoprotein E-Null Mice, Circulation vol. 106, pp. 2827-2835, 2002.
Burstein, Y. et al., Partial Amino-Acid Sequence of the Precursor of an Immunoglobulin Light Chain containing NH2-Terminal Pyroglutamic Acid, Proc. Natl. Acad. Sci. USA, vol. 73, No. 8, pp. 2604-2608, 1976.
Canfield, S. et al., "The Binding Affinity of Human IgG for its High Affinity Fc Receptor is Determined by Multiple Amino Acids in the CH2 Domain and is Modulated by the Hinge Region," J. Exp. Med., 1991, 173:1483-1491.
Chelius et al., "Formation of Pyroglutamic Acid from N-Terminal Glutamic Acid in Immunoglobulin Gamma Antibodies" Analytical Chemistry, 78:2370-2376, (2006).
Crall, F. et al., The Extramural and Intramural Coronary Arteries in Juvenile Diabetes Mellitus, American Journal of Medicine, vol. 64, pp. 221-230, 1978.
Deane, R. et al., "Rage mediates amyloid-beta peptide transport across the blood-brain barrier and accumulation in brain," 2003, Nature Medicine, 9:907-913.
Decision of Grant mailed Aug. 14, 2009 corresponding to Eurasian Patent Application No. 200700402.
Decision of Grant mailed Oct. 7, 2009 corresponding to Georgian Patent Application No. AP 2005 009905.
Decision on Grant mailed Jul. 23, 2009 corresponding to Uzbekistan Patent Application Serial No. IAP20070074.
Decision on Grant mailed May 5, 2010 corresponding to Uzbekistan Patent Application No. IAP 2007-0073.
Deed of Letters Patent issued Jan. 7, 2010 corresponding to New Zealand Patent Application No. 552128.
Degenhardt, T. et al., Chemical Modification of Proteins by Methylglyoxal, Cellular and Molecular Biology, vol. 44, No. 7, pp. 1139-1145, 1998.
Dyer, D. et al., Accumulation of Maillard Reaction Products in Skin Collagen in Diabetes and Aging, J. Clin. Invest., vol. 91, pp. 2463-2469, 1993.
Dyer, D. et al., Formation of Pentosidine during Nonenzymatic Browning of Proteins by Glucose, Journal of Bilogoical Chemistry, vol. 266, No. 18, pp. 11654-11660, 1991.
Edelman, G. et al., "The Covalent Structure of an Entire gamma-G Immunoglobulin Molecule," 1969, Proc. Natl. Acad. Sci. USA, 63:78-85.
Ellison, J. et al., Linkage and Sequence Holomolgy of Two Human Immunoglobulin gamma heavy Chain Constant region Genes, Proc. Natl., Acad. Sci. USA, vol. 79, pp. 1984-1988, 1982.
Examination Report and Notice of Acceptance of Complete Specification mailed May 10, 2010 corresponding to New Zealand Patent Application No. 552842.
Examination Report mailed Sep. 1, 2014 corresponding to European Patent Application No. 10718284.2.
First Examination Report issued by Intellectual Property Office of New Zealand on May 5, 2008 corresponding to Application No. 552128.
Flyvbjerg, A. et al., Long Term Renal Effects of a Neutralizing Rage Antibody in Obese Type 2 Diabetic Mice, Diabetes, vol. 53, pp. 166-172, 2004.
GenBank Accession No. M91211, Dec. 9, 1993.
GenBank Accession No. NP 001127, 1992.
Girouard, H. and Iadecola, C., "Neurovascular coupling in the normal brain and in hypertension, stroke, and Alzheimer disease," 2006, J. Appl. Physiol., 100:328-335.
Guo, J. et al., Inflammation-Dependent Cerebral Deposition of Serum Amyloid A Protein in a Mouse Model of Amyloidosis, Journal of Neuroscience, vol. 22, No. 14, pp. 5900-5909, 2002.
Hamby, R. et al., Reappraisal of the Role of the Diabetic State in Coronary Artery Disease, Chest, vol. 2, pp. 251-257, 1976.
Hofmann, M. et al., Rage and Arthritis: the G82S Polymorphism Amplifies the Inflammatory Response, Genes and Immunity, vol. 3, pp. 123-135, 2002.
Hori, et al., "The Receptor for Advanced Glycation End Products (RAGE) is a Cellular Binding Site for Amphoterin," The Journal of Biological Chemistry, 270(43); pp. 25752-25761, (1995).
Hutchins, J. et al., "Improved biodistribution, tumor targeting, and reduced immunogenicity in mice with a gamma-4 variant of Campath-1 H," 1995, Proc. Natl. Acad. Sci. USA, 92:11980-11984.
Huttunen et al., Receptor for Advanced Glycation End Products-Binding COOh-Terminal Motif of Amphoterin Inhibits Invasive Migration and Metastasis, Cancer Research, 62(12); 4805-4811, (2002).
International Search Report for PCT Application, PCT/US2005/027705, mailed Nov. 10, 2005.
International Search Report for PCT Application, PCT/US2007/001686, mailed Aug. 29, 2007.
International Search Report for PCT Application, PCT/US2007/010125, mailed Feb. 22, 2008.
International Search Report mailed Dec. 15, 2005 corresponding to Application No. PCT/US2005/027694.
International Search Report mailed Nov. 12, 2008 corresponding to Application No. PCT/US2008/001786.
Ishihara, K. et al., "The receptor for advanced glycation end-products (RAGE) directly binds to ERK by a D-domain-like docking site," FEBS Letters, 2003, 550:107-113.
Jennifer L.R. Freeman, et al., "Characterization of a Glycoprotein of TTP4000—A Soluble Decoy RAGE Antagonist" Experimental Biology 2013: Biochemistry and Molecular Biology Section, Apr. 22, 2013, Poster.
Jennifer L.R. Freeman, et al., "Characterization of a Glycoprotein of TTP4000—A Soluble Decoy RAGE Antagonist," FASEB J (Meeting Abstract Supplement) Apr. 9, 2013 27:803.2.
Johnson, M. et al., Antioxidant with Marked Lipid-and Glucose-Lowering Activity in Diabetic Rats and Mice, Diabetes, vol. 42, pp. 1179-1186, 1993.
Jones, A. et al., Analysis of Polypeptides and Proteins, Advances Drug Delivery Reviews, vol. 10, pp. 29-90, 1993.
Kannel, W. et al., Diabetes and Cardiovascular Disease—The Framingham Study, J. Am. Med. Assoc., VI. 241, pp. 2035-2038, 1979.
Kannel, W. et al., Diabetes and Glucose Tolerance as Risk Factors for Cardiovascular Disease: The Framingham Study, Diabetic Care, vol. 2, pp. 120-126, 1979.
Kumar, S. et al., "Rage at the Blood-Brain Barrier Mediates Neurovascular Dysfunction Caused by Amyloid-beta 1-40 Peptide," 2000, Neurosci. Program, p. 141 (abstract only).
Kunzendorf U, et al., "Immunomodulation in Experimental and Clinical Nephrology Using Chimeric Proteins," Kidney Blood Press

(56) References Cited

OTHER PUBLICATIONS

Res. 19(3-4):201-4, Department of Internal Medicine and Nephrology, Universitatsklinikum Benjamin Franklin, (1996).
Leder, A. et al., v-Ha-ras Transgene Abrogates the Initiation Step in Mouse Skin Tumorigenesis: Effects of Phorbol Esters and Retinoic Acid, Proc. Natl. Aced, Sci. USA, vol. 81, pp. 9178-9182, 1990.
Lee, V. et al., Peptide and Protein Drug Delivery, Marcel Dekker Inc., pp. 247-301 (1991).
Lekkerkerker, A.N. et al., "Potency of HIV-1 envelope glycoprotein gp 120 anitbodies to inhibit the interaction of DC-SIGN with HIV-1 gp120", Virology, vol. 329, No. 2, Nov. 24, 2004, pp. 465-476.
Li, F. et al., "Current Therapeutic Antibody Production and Process Optimization," 2006, BioProcessing Journal, 5:16-25.
Li, J. et al., Characterization and Functional Analysis of the Promoter of RAGE, the Receptor for Advanced Glycation End Products, Journal of Biological Chemistry, vol. 272, No. 26, pp. 16498-16506, 1997.
Li, J., et al., "Sp1-Binding Elements in the Promoter of RAGE are Essential for Amphoterinmediated Gene Expression in Cultured Neuroblastoma Cells," The Journal of Biological Chemistry, 273(47); pp. 30870-30878, (1998).
Liliensiek, B. et al., Receptor for Advanced Glycation End Products (RAGE) regulates Sepsis but not the Adaptive Immune Response, Journal of Clinical Investigation, vol. 113, No. 11, pp. 1641-1650, 2004.
Lue, L. et al., Involvement of Microglial Receptor for Advanced Glycation Endproducts (RAGE) in Alzheimer's Disease: Identification of a Cellular Activation Mechanism, Experimental Neurology, vol. 171, pp. 29-45, 2001.
Lugering, N. et al., The Myeloic Related Protein MRP8/14 (27E10 antigen)—Usefulness as a Potential Marker for Disease Activity in Ulcerative Colitis and Putative Biological Function, European Journal of Clinical Investigation, vol. 25, pp. 659-664, 1995.
Luth, H. et al., Age-and-Stage-dependent Accumulation of Advanced Glycation End Products in Intracellular Deposits in Normal and Alzheimer's Disease Brains, Cerebral Cortex, vol. 15, pp. 211-220, 2005.
Mackic, J. et al., "Human Blood-Brain Barrier Receptors for Alzheimer's Amyloid-beta 1-30. Asymmetrical Binding, Endocytosis, and Transtcytosis at the Apical Side of Brain Microvascular Endothelial Cell Monolayer," 1998, J. Clin. Invest., 102:734-743.
May 15, 2006 Interview Summary issued in connection with U.S. Appl. No. 10/643,589.
Mickle et al. "Genotype-Phenotype Relationships in Cystic Fibrosis," Med. Clin. North Am., 84(2); pp. 597-607, May (2000).
Miyata, T. et al., beta-2-Microglobulin Modified with Advanced Glycation End Products is a Major Component of Hemodialysis-associated Amyloidosis, J. Clin. Invest., vol. 92, pp. 1243-1525, 1993.
Miyata, T. et al., the Receptor for Advanced Glycation End Products (RAGE) is a Central Mediator of the Interaction of AGE-beta-2 Microglobulin with Human Mononuclear Phagocytes via an Oxidant-Sensitive Pathway, J. Clin. Invest., vol. 98, No. 5, pp. 1088-1094, 1996.
Mohler, K. et al., Soluble Tumor Necrosis Factor (TNF) Receptors are Effective Therapeutic Agents in Lethal Endotoxemia and Function Simultaneously as Both TNF Carriers and TNF Antafonists, Journal of Immunology, vol. 151, No. 3, pp. 1548-1561, 1993.
Morgan, B. et al., Chapter 26-Approaches to the Discovery of Non-Peptide Ligands for Peptide Receptors and Peptidases, Ann Reports Med. Chem., vol. 24, pp. 243-252, 1989.
Morton, Phillip A., et al., "Differential Effects of CTLA-4 Substitutions on the Binding of Human CD80 (B7-1) and CD86 (B7-2)," The Journal of Immunology, 156: 1047-1054, The American Associates of Immunologists, (1996).
Needleman, S. et al., A General Method Applicable to the Search for Similarities in the Amino Acid Sequence of Two Proteins, J. Mol. Biol., vol. 48, pp. 443-453, 1970.

Nickerson, P. et al., "Prolonged islet allograft acceptance in the absence of interleukin 4 expression", Transplant Immunology, vol. 4, No. 1, Mar. 1996, pp. 81-85.
Notice of Acceptance mailed Aug. 12, 2009 corresponding to New Zealand Patent Application Serial No. 552128.
Notice of Acceptance mailed Mar. 9, 2010 corresponding to South African Patent Application No. 2009/06459.
Notice of Allowance mailed Apr. 29, 2010 corresponding to U.S. Appl. No. 11/629,437.
Notice of Allowance mailed Jan. 25, 2010 corresponding to U.S. Appl. No. 11/629,437.
Notice of Allowance mailed Mar. 23, 2010 corresponding to U.S. Appl. No. 11/197,038.
Notification of Acceptance mailed May 11, 2010 corresponding to South African Patent Application No. 2007/0643.
Office Action mailed Apr. 13, 2009 corresponding to Application Serial No. UZ IPA20070074.
Office Action mailed Apr. 16, 2009 corresponding to Indian Patent Application No. 740/DELNP/2007.
Office Action mailed Apr. 24, 2006 in connection with U.S. Appl. No. 10/643,589.
Office Action mailed Apr. 28, 2010 corresponding to Vietnam Patent Application No. 1-2007-00486.
Office Action mailed Apr. 8, 2010 corresponding to U.S. Appl. No. 12/069,499.
Office Action mailed Apr. 9, 2010 corresponding to Canadian Patent Application No. 2,570,324.
Office Action mailed Aug. 12, 2009 corresponding to U.S. Appl. No. 11/789,637.
Office Action mailed Aug. 25, 2010 corresponding to Egyptian Patent Application No. PCT96/2007.
Office Action mailed Aug. 5, 2009 corresponding to Indonesian Patent Application No. W-00 2007 00370.
Office Action mailed Dec. 1, 2009 corresponding to Australian Patent Application No. 2005271449.
Office Action mailed Dec. 10, 2008 in connection with U.S. Appl. No. 11/197,644.
Office Action mailed Dec. 18, 2009 corresponding to Chinese Patent Application No. 200580025947.7.
Office Action mailed Dec. 24, 2009 corresponding to New Zealand Patent Application No. 552842.
Office Action mailed Dec. 28, 2009 corresponding to U.S. Appl. No. 11/789,637.
Office Action mailed Feb. 12, 2009 corresponding to U.S. Appl. No. 11/197,038.
Office Action mailed Feb. 16, 2009 corresponding to Application Serial No. EA 200870244.
Office Action mailed Feb. 24, 2010 corresponding to Canadian Patent Application No. 2,575,830.
Office Action mailed Feb. 26, 2009 corresponding to U.S. Appl. No. 11/197,038.
Office Action mailed Feb. 3, 2009 in connection with U.S. Appl. No. 10/990,310.
Office Action mailed Feb. 5, 2008 corresponding to Eurasian Patent Application No. 200700402.
Office Action mailed Jan. 11, 2008 in connection with U.S. Appl. No. 11/197,644.
Office Action mailed Jan. 15, 2009 corresponding to Uzbekistan Patent Application No. IAP 2007 0073.
Office Action mailed Jan. 4, 2008 corresponding to U.S. Appl. No. 11/197,038.
Office Action mailed Jul. 10, 2009 corresponding to U.S. Appl. No. 11/629,437.
Office Action mailed Jul. 15, 2009 corresponding to U.S. Appl. No. 11/197,038.
Office Action mailed Jul. 29, 2009 corresponding to European Patent Application Serial No. 07 716 896.1.
Office Action mailed Jul. 30, 2010 corresponding to Canadian Patent Application No. 2,638,907.
Office Action mailed Jun. 11, 2009 corresponding to U.S. Appl. No. 11/629,437.

(56) References Cited

OTHER PUBLICATIONS

Office Action mailed Jun. 12, 2009 by the European Patent Office (received notice Jun. 22, 2009) corresponding to Application No. 05 778 764.0 2401.
Office Action mailed Jun. 16, 2010 corresponding to Philippine Patent Application No. 1-2007-500024.
Office Action mailed Jun. 18, 2008 corresponding to New Zealand Patent Application No. 552842.
Office Action mailed Jun. 21, 2007 in connection with U.S. Appl. No. 10/643,589.
Office Action mailed Jun. 23, 2010 corresponding to U.S. Appl. No. 11/197,644.
Office Action mailed Mar. 18, 2009 corresponding to U.S. Appl. No. 10/643,589.
Office Action mailed Mar. 2, 2009 corresponding to European Patent Application No. 05 779 648.4.
Office Action mailed Mar. 24, 2010 corresponding to Ukraine Patent Application No. 200702273.
Office Action mailed May 12, 2010 corresponding to Canadian Patent Application No. 2,651,348.
Office Action mailed May 31, 2010 corresponding to New Zealand Patent Application No. 571692.
Office Action mailed May 7, 2010 corresponding to New Zealand Patent Application No. 569545.
Office Action mailed Nov. 17, 2008 corresponding to Application Serial No. UZ IAP20070074.
Office Action mailed Nov. 20, 2012 corresponding to U.S. Appl. No. 13/029,622.
Office Action mailed Nov. 6, 2008 corresponding to U.S. Appl. No. 10/643,589.
Office Action mailed Oct. 18, 2007 in connection with U.S. Appl. No. 10/643,589.
Office Action mailed Oct. 23, 2009 corresponding to U.S. Appl. No. 11/197,644.
Office Action mailed Oct. 31, 2008 corresponding to Chinese Patent Application No. 200580026106.8.
Office Action mailed Sep. 15, 2009 corresponding to Ukraine Patent Application No. 2007 02216.
Office Action mailed Sep. 24, 2007 by the Patent Office of Uzbekistan in connection with Uzbekistan Patent Application No. IAP20070074.
Office Action mailed Sep. 24, 2007 corresponding to Uzbekistan Patent Application No. IAP 2007 0073.
Office Action mailed Sep. 26, 2006 in connection with U.S. Appl. No. 10/643,589.
Official Notice of Readiness to Grant mailed Apr. 2009 corresponding to Eurasian Patent Application No. 200700402.
Opposition filed by ALAFAR in Sep. 2007 against Patent Application No. SP-07-7297 in Ecuador.
Opposition filed by ALAFAR on Jul. 25, 2007 against Ecuador Patent Application No. SP-07-7221 and translation.
Park, J. et al., "Involvement of Toll-like Receptors 2 and 4 in Cellular Activation by High Mobility Group Box 1 Protein," 2004, J. Biol. Chem., 279:7370-7377.
Parker, L. et al., "Toll-Like Receptor (TLR)2 and TLR4 Agonists Regulate CCr Expression in Human Monocytic Cells," 2004, J. Immunol., 172:4977-2986.
Parkkinen, J. et al., Amphoterin, the 30-kDa Protein in a Family of HMG1-type Polypeptides, Journal of Biological Chemistry, vol. 268, No. 26, pp. 19726-19738, 1993.
Pearson, W. et al., Improved Tools for Biological Sequence Comparsion, Proc. Natl. Acad. Sci. USA, vol. 85, pp. 2444-2448, 1998.
Pending Claims for U.S. Appl. No. 13/029,622 filed Jul. 27, 2012.
Peppel et al., "A Tumor Necrosis Factor (TNF) Receptor-IgG Heavy Chain Chimeric Protein as a Bivalent Antagonist of TNF Activity," J. Exp. Med. 1;174 (6): 1483-9, Dec. (2000).
Petzold, A. et al., Cerebrospinal Fluid S100B correlates with Brain Atrophy in Alzheimer's Disease, Neuroscience Letters, vol. 336, pp. 167-170, 2003.

Preliminary Favourable Decision of Grant mailed Oct. 7, 2009 corresponding to Georgian Patent Application No. AP 2005 009904.
Pyorala, K. et al., Diabetes and Atherosclerosis, An Epidemiologic View, Diabests/Metabolism Reviews, vol. 3, No. 2, pp. 463-524, 1987.
Rammes, A. et al., Myeloid-related Protein (MRP) 8 and MRP14, Calcium-binding Proteins of the S100 Family, are Secreted by Activated Monocytes via a Novel, Tubulin-dependent Pathway, Journal of Biological Chemistry, vol. 272, No. 14, pp. 9496-9502, 1997.
Rauvala, H. et al., Isolation and Some Characteristics of an Adhesive Factor of Brain that Enhances Neurite Outgrowth in Central Neurons, Journal of Biological Chemistry, vol. 262, No. 34, pp. 16625-16635, 1987.
Reddy, S. et al., N-epsilon-(Carboxymethyl)lysine is a Dominant Advanced Glycation End Product (AGE)Antigen in Tissue Proteins, Biochemistry, vol. 34, pp. 10872-10878, 1995.
Renard, C. et al., "Recombinant Advanced Glycation End Product Receptor Pharmacokinetics in Normal and Diabetic Rats," Molecular Pharmacology, 52: 54-62, The American Society for Pharmacology and Experimental Theapeutics, (1997).
Renard, C. et al., The Human and Rat Recombinant Receptors for Advanced Glycation End Products have a High Degree of Homology but Different Pharmacokinetic Properties in Rats, Journal of Pharmacology and Experimental Therapeutics, vol. 290, No. 3, pp. 1458-1466, 1999.
Robertson, W. et al., Atherosclerosis in Persons with Hypertension and Diabetes Mellitus, Laboratory Investigation, vol. 18, No. 5, pp. 538-551, 1968.
Rouhiainen et al., "Regulation of Monocyte Migration by Amphoterin (HMGB1)," Blood, vol. 104:4, pp. 1174-1176, 2004.
Sasaki, N. et al., Immunohistochemical Distribution of the Receptor for Advanced Glycation End Products in Neurons and Astrocytes in Alzheimer's Disease, Brain Research, vol. 888, pp. 256-262, 2001.
Schafer, B. et al., The S100 Family of EF-Hand Calcium-Binding Proteins: Functions and Pathology, TIBS, vol. 21, 1996.
Schleicher, E. et al., Increased Accumulation of the Glycoxidation Product N-epsilon-(carboxymethyl)lysine in Human Tissues in Diabetes and Aging, J. Clin. Invest, vol. 99, No. 3 pp. 457-468, 1997.
Schlueter, C. et al., "Accession: NP_001127[gi:10835203], Degini-tion: advanced glycosylation end product-specific receptor isoform 1 precursor [Homosapiens]," NCBI Entrez Nucleotide [online]: Dec. 21, 2003 upraod, NCBI, [retrieved on May 31, 2012].
Schmidt, A. et al., "Receptor for Advanced Glycation End Products (AGEs) has a Central Role in Vessel Wall Interactions and Gene Activation in Response to Circulating AGE Proteins," Proc. Natl. Acad. Sci., 91; pp. 8807-8811, (1994).
Schmidt, A. et al., The Dark Side of Glucose, Nature Medicine, vol. 1, No. 10, pp. 1002-1004, 1995.
Schmidt, A. et al., The V-Domain of Receptor for Advanced Glycation Endproducts (RAGE) Mediates Binding of AGESs: A Novel Target for Therapy of Diabetic Complications (Abstract), Circulation, vol. 96, No. Supp. 194, pp. 137, 1987.
Schmidt, Ann Marie et al. , "Isolation and Characterization of Two Binding Proteins for Advanced Glycosylation End Products from . . . ," The Journal of Bilolgical Chemistry, pp. 14987-14997, vol. 267, No. 21, The American Society for Biochemistry and Molecular Biology, Inc., Jul. 25 (1992).
Search Report and Written Opinion of Octrooicentrum Nederland mailed Feb. 8, 2008 corresponding to Application No. 2000476.
Search Report mailed Mar. 27, 2008 corresponding to Georgian Patent Application No. AP 2005 009905.
Shoji-Hosaka Emi et al., "Enhanced FC-Dependent Cellular Cytotoxicity of FC Fusion Proteins Derived From TNF Receptor II and LFA-3 By Fucose Removal From ASN-Linked . . . ," Journal of Biochemistry, Japanese Biochemical Society/OUP, vol. 140, No. 6, Jan. 1, 2006, pp. 777-783.
Simon, R. et al., Peptoids: A Modular Approach to Drug Discovery, Proc. Natl. Acad. Sci. USA, vol. 89, pp. 9367-9371, 1992.
Smith, T. et al., Comparison of Biosequences, Advances in Applied Mathematics, Chapter 2, pp. 428-488, 1981.
Sousa, M. et al., Interaction of the Receptor for Advanced Glycation End Products (RAGE) with Transthyretin Triggers Nuclear Tran-

(56) References Cited

OTHER PUBLICATIONS scription Factor kB (NF-kB) Activation, Laboratory Investigation, vol. 80, No. 7, pp. 1101-1110, 2000.
Stern et al., "Receptor for Advanced Glycation Endproducts (RAGE) and the Complications of Diabetes," Ageing Research Reviews, 1(1); 1-15, (2002).
Stevenson. Characterization of protein and peptide stability and solubility in non-aqueous solvents. Curr Pharm Biotechnol. Sep. 2000;1(2):165-82.
Tanaka, et al., "The Receptor for Advanced Glycation End Products is Induced by the Glycation Products Themselves and Tumor Necrosis Factor-alpha through Nuclear Factor-kB, and by 17-beta-Estradiol through Sp-1 in . . . ," The Journal of Biological Chemistry, 275(33); pp. 25781-25790 (2000).
Tenno, T. et al., "High-throughput construction method for expression vector of peptides for NMR study suited for isotopic labeling," Protein Engineering, Design & Selection, 2004, 17:305-314.
Waller, B. et al., Status of the Coronary Arteries at Necropsy in Diabetes Mellitus with Onset after Age 30 years, Am. J. Med., vol. 69, pp. 498-506, 1980.
Weiss, P. et al., "Flexible Methodology for Developing Mammalian Cell Lines," The BioPharm International Guide, Feb. 2006, pp. 30-35.
Wilbur, W. et al., Rapid Similarity Searches of Nucleic Acid and Protein Data Banks, Proc. Natl. Acad. Sci., USA, vol. 80, pp. 726-730, 1983.
Wines, Bruce D. et al., "The IgG Fc Contains Distinct Fc Receptor (FcR) Binding Sites: The Leukocyte Receptors Fc-gamma-RI and Fc-gamma-RIIa Bind to a Region in the Fc Distinct from . . . ," The Journal of Immunology, 164: 5313-5318, The American Association of Immunologists, (2000).
Written Opinion and Search Report dated Feb. 11, 2010 corresponding to Singapore Patent Application No. 200807721-6.
Written Opinion of the Australian Patent Office mailed Mar. 5, 2008 corresponding to Singapore Patent Application No. 200700673-7.
Written Opinion of the Australian Patent Office mailed Nov. 21, 2008 corresponding to Singapore Patent Application No. 200700673-7.
Written Opinion of the Austrian Patent Office mailed Jun. 17, 2009 corresponding to Singapore Patent Application No. 200700364-3.
Written Opinion of the International Search Authority for related PCT Application, PCT/US2007/010125, mailed Feb. 22, 2008.
Written Opinion of the International Searching Authority mailed Aug. 29, 2007 corresponding to Application No. PCT/US2007/001686.
Written Opinion of the International Searching Authority mailed Dec. 15, 2005 corresponding to Application No. PCT/US2005/027694.
Written Opinion of the International Searching Authority mailed Nov. 10, 2005 corresponding to Application No. PCT/US2005/027705.
Written Opinion of the International Searching Authority mailed Nov. 12, 2008 corresponding to Application No. PCT/US2008/001786.
Yan et al., "Two-Amino Acid Molecular Switch in an Epithelial Morphogen that Regulates Binding to Two Distinct Receptors," Science 290; 523-527, (2000).
Yan, S. D. et al., "Amyloid-beta Peptide-Receptor for Advanced Glycation Endproduct Interaction Elicits Neuronal Expression of Macrophage-Colony Stimulating Factor: A Proinflammatory Pathway in Alzheimer Disease," Proc. Natl. Acad. Sci., 94: pp. 5296-5301, (1997).
Yan, S. et al., Rage-A-beta Interactions in the Pathophysiology of Alzheimer Disease, Restorative Neurology and Neuroscience, vol. 12, pp. 167-173, 1998.
Yan, S. et al., Receptor-dependent Cell Stress and Amyloid Accumulation in Systemic Amyloidosis, Nature Medicine, vol. 6, No. 6, pp. 643-651, 2000.
Yan, S. et al., Suppression of Experimental Autoimmune Encephalomyelitis by Selective Blockade of Encephalitogenic T-cell Infiltration of the Central Nervous System, Nature Medicine, vol. 9, No. 3, pp. 287-293, 2003.
Yeh, C. et al., Requirement for p38 and p44/p42 Mitogen-Activates Protein Kinases in RAGE-Mediated Nuclear Factor-k-beta Transcriptional Activation and Cytokine Secretion, Diabetes, vol. 50, pp. 1495-1504, 2001.
Zhou, Z. et al., Receptor for AGE (RAGE) Mediates Neointimal Formation in Response to Arterial Injury, Circulation, vol. 107, pp. 2238-2243, 2003.
Zhou, Z. et al., Regulation of Osteoclast Function and Bone Mann by RAGE, Journal of Experimental Medicine, vol. 203, No. 4, pp. 1067-1080, 2006.
Zimmer, D. et al., The S100 Protein Family: History, Function, and Expression, Brain Research Bulletin, vol. 37, No. 4, pp. 417-429, 1995.
Robert Rothlein, et al. "TTP4000, a soluble fusion protein inhibitor . . . Alzheimer's disease," poster presented: Cambridge Health Science, 2nd Annual Successful Targeting of Alzheimer's Disease, Philadelphia, PA, Jun. 16-17, 2010.

* cited by examiner

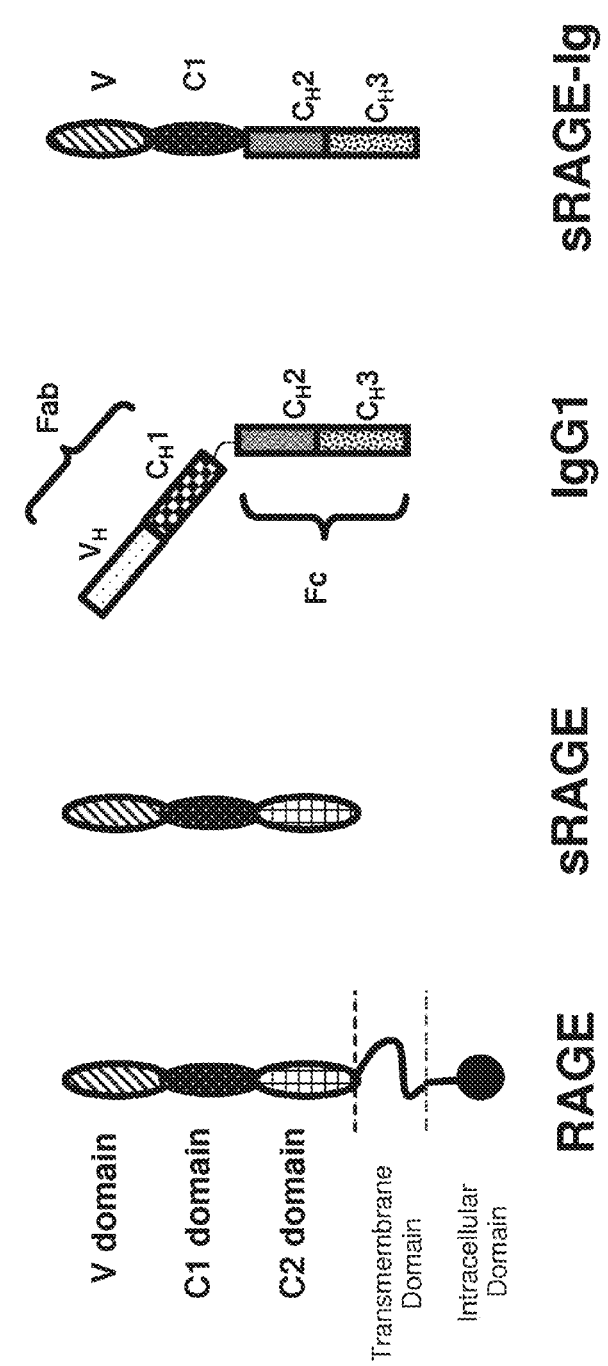

FIGURE 2A

MAAGTAVGAW VLVLSLWGAV VGAQNITARI GEPLVLKCKG APKKPPPQRLE

WKLNTGRTEA WKVLSPQGGG PWDSVARVLP NGSLFLPAVG IQDEGIFRCQ

AMNRNGKETK SNYRVRVYQI PGKPEIVDSA SELTAGVPNK VGTCVSEGSY

PAGTLSWHLD GKPLVPNEKG VSVKEQTRRH PETGLFTLQS ELMVTPARGG

DPRPTFSCSF SPGLPRHRAL RTAPIQPRVW EPVPLEEVQL VVEPEGGAVA

PPSVFLFPPK PKDTLMISRT PEVTCVVVDV SHEDPEVKFN WYVDGVEVHN
⎿―――――――――――――――――――――――――――――――――  C$_H$2 Domain ――――――

AKTKPREEQY NSTYRVVSVL TVLHQDWLNG KEYKCKVSNK ALPAPIEKTI
――――――――――――――――――――――――⏌⎿――――――――――――――――――  C$_H$3 Domain SKAKGQPREP QVYTLPPSRD ELTKNQVSLT CLVKGFYPSD IAVEWESNGQ
――――――――――――――――――――――――――――――――――――――――――――――――――――

PENNYKTTPP VLDSDGPFFL YSKLTVDKSR WQQGNVFSCS VMHEALHNHY
――――――――――――――――――――――――――――――――――――――――――――――――――――

TQKSLSLSPG K    (SEQ ID NO:1)
―――――――――⏌

FIGURE 2B

```
ATGGCAGCCG GAACAGCAGT TGGAGCCTGG GTGCTGGTCC TCAGTCTGTG GGGGGCAGTA GTAGGTGCTC
AAAACATCAC AGCCCGGATT GGCGAGCCAC TGGTGCTGAA GTGTAAGGGG GCCCCCAAGA AACCACCCCA
GCGGCTGGAA TGGAAACTGA ACACAGGCCG GACAGAAGCT TGGAAGGTCC TGTCTCCCCA GGGAGGAGGC
CCCTGGGACA GTGTGGCTCG TGTCCTTCCC AACGGCTCCC TCTTCCTTCC GGCTGTCGGG ATCCAGGATG
AGGGGATTTT CCGGTGCCAG GCAATGAACA GGAGACCAAG TCCAACTACC GAGTCCGTGT
CTACCAGATT CCTGGGAAGC CAGAAATTGT AGATTCTGCC TCTGAACTCA CGGCTGGTGT TCCCAATAAG
GTGGGGACAT GTGTGTCAGA GGGGAGCTAC CCTGCAGGGA CTCTTAGCTG GCACTTGGAT GGGAAGCCCC
TGGGTGCCTAA TGAGAAGGGA GTATCTGTGA AGGAACAGAC CCTGAGACAG GGCTCTTCAC
ACTGCAGTCG GAGCTAATGG TGACCCCAGC CCGGGGAGGA GATCCCCGTC CCACCTTCTC CTGTAGCTTC
AGCCCAGGCC TTCCCCGACA CGCACAGCC CCATCCAGCC CCGTGTCTGG GAGCCTGTGC
CTCTGGAGGA GGTCCAATTG GTGGTGGAGC CAGAAGGTGG AGCAGTAGCT CCTCCGTCAG TCTTCCTCTT
CCCCCAAAA CCCAAGGACA CCCTCATGAT CTGGAGGTCA CATGCGTGGT GGTGGACGTG
AGCCACGAAG ACCCTGAGGT CAAGTTCAAC TGGTACGTGG ACGGCGTGGA GGTGCATAAT GCCAAGACAA
AGCCGCGGGA GGAGCAGTAC AACAGCACGT ACCGTGTGGT CAGCGTCCTC ACCGTCCTGC ACCAGGACTG
GCTGAATGGC AAGGAGTACA AGTGCAAGGT CTCCAACAAA GCCCTCCCAG CCCCCATCGA GAAAACCATC
TCCAAAGCCA AAGGGCAGCC CCGAGAACCA CAGGTGTACA CCCTGCCCCC ATCCCGGGAT GAGCTGACCA
AGAACCAGGT CAGCCTGACC TGCCTGGTCA AAGGCTTCTA TCCCAGCGAC ATCGCCGTGG AGTGGGAGAG
CAATGGGCAG CCGGAGAACA ACTACAAGAC CACGCCTCCC GTGCTGGACT CCGACGGCTC CTTCTTCCTC
TACAGCAAGC TCACCGTGGA CAAGAGCAGG TGGCAGCAGG GGAACGTCTT CTCATGCTCC GTGATGCATG
AGGCTCTGCA CAACCACTAC ACGCAGAAGA GCCTCTCCCT GTCTCCGGGT AAATGA   (SEQ ID NO:2)
```

FIGURE 9

T1pE = pENITAR (684.36 Da)

T10 = VLPNGSLFLPAVGIQDEGIFR (2241.22 Da)

T31 = EEQYNSTYR (1188.50 Da)

FIGURE 13A

Antibody 5.948.1 Heavy Chain amino acid sequence:

qvqlvqsgaevkkpgasvkvsckasgyftfsydinwvrqatgqglewmgwmdpns
gntgyagkfqgrvtmtrNtsistaymelssIrsedtavyycarghydsdgvysfsgmd
vwgqgttvtvssASTKGPSVFPLAPCSRSTSESTAALGCLVKDYFP
EPVTVSWNSGALTSGVHTFPAVLQSSGLYSLSSVVTVPSSNF
GTQTYTCNVDHKPSNTKVDKTVERKCCVECPPCPAPPVAGP
SVFLFPPKPKDTLMISRTPEVTCVVVDVSHEDPEVQFNWYVD
GVEVHNAKTKPREEQFNSTFRVVSVLTVVHQDWLNGKEYKC
KVSNKGLPAPIEKTISKTKGQPREPQVYTLPPSREEMTKNQVS
LTCLVKGFYPSDIAVEWESNGQPENNYKTTPPMLDSDGSFFL
YSKLTVDKSRWQQGNVFSCSVMHEALHNHYTQKSLSLSPGK
(SEQ ID NO:8)

Figure 13B

Antibody 5.948.1: nucleic acid sequence encoding heavy chain (V domain in capital letters)

CAGGTGCAGCTGGTGCAGTCTGGGGCTGAGGTGAAGAAGCCTGGGGCCTCAGTGAAGG
TCTCCTGCAAGGCTTCTGGATACACCTTCACCAGTTATGATATCAACTGGGTGCGACAGG
CCACTGGACAAGGGCTTGAGTGGATGGGATGGACCCTAACAGTGGTAACAGAGGC
TATGCACAGAAGTTCCAGGGCAGAGTCACCATGACCAGGAACACCTCCATAAGCACAGC
CTACATGGAGCTGAGCAGCCTGAGATCTGAGGACACGGCCGTGTATTACTGTGCGAGAG
GCCACTATGATAGTGATAGTGGTTATTACTCCTTCTCCGGTATGGACGTCTGGGGCCAAGGGA
CCACGGTCACCGTCTCCTCAgcctccaccaagggcccatcggtcttccccctggcgccctgctccaggagcacctc
gagagcacagcggccctgggctgcctggtcaaggactacttccccgaaccggtgacggtgtcgtggaactcaggcgctctgaccagcggcgtgcacaccttcccagctgtcctacagtcctcaggactctactccctcagcagcgtggtgaccgtgccctccagcaacttcggcacccagacctacatctgcaacgtgaatcacaagcccagcaacaccaaggtggacaagacagttgagcgcaaatgttgtg
gagtgccaccgtgcccagcacctgaactcctggggggaccgtcagtcttcctcttccccccaaaacccaaggacaccctcatgatctc
ccggacccctgaggtcacgtgcgtggtggtggacgtgagccacgaagaccctgaggtcaagttcaactggtacgtggacggcgt
ggaggtgcataatgccaagacaaagccgcggggaggagcagtacaacagcacgtaccgtgtggtcagcgtcctcaccgtcctgcac
caggactggctgaacggcaaggagtacaagtgcaaggtctccaacaaagccctcccagcccccatcgagaaaaccatctccaa
aaccaaagggcagccccgagaaccacaggtgtacaccctg
cccccatcccgggaggagatgaccaagaaccaggtcagcctgacctgcctggtcaaaggcttctaccccagcgacatcgccgtg
gagtgggagagcaatgggcagccggagaacaactacaagaccacacctcccatgctggactccgacggctccttcttcctctacaa
gcaagtcaccgtggacaagagcaggtggcagcaggggaacgtcttctcatgctccgtgatgcatgaggctctgcacaaccactaca
cacgcagaagagcctctccctgtctccggg (SEQ ID NO:9)

Figure 13C

Antibody 5.948.1 Kappa Light Chain amino acid sequence:

divmtqsplslpvtpgepasiscrssq sllhrngvnyldwylqkpgqspqlliylgsnrasgvpdr
fsgsgsgtdftlkisrveaedvgvycmqalqtpatfggtkveikRTVAAPSVFIFPPS
DEQLKSGTASVVCLLNNFYPREAKVQWKVDNALQSGNSQESVTE
QDSKDSTYSLSSTLTLSKADYEKHKVYACEVTHQGLSSPVTKSFNR
GEC (SEQ ID NO:10)

Figure 13D

Antibody 5.948.1: nucleic acid sequence encoding Kappa Light Chain

GATATTGTGATGACTCAGTCTCCACTCTCCCTGCCCGTCACCCCTG
GAGAGCCGGCCTCCATCTCCTGTAGGTCTAGTCAGAGCCTCCTGC
ATAGGAATGGATACAACTACTTGGATTGGTACCTGCAGAAGCCAGG
GCAGTCTCCACAGCTCCTGATCTATTTGGGTTCTAATCGGCCTCC
GGGGTCCCTGACAGGTTCAGTGGCAGTGGATCAGGCACAGATTTT
ACACTGAAAATCAGCAGAGTGGAGGCTGAGGATGTTGGGGTTTATT
ACTGCATGCAAGCTCTACAAACTCCTCGGCCCACTTTCGGCGGAG
GGACCAAGGTGGAGATCAAAcgaactgtggctgcaccatctgtcttcatcttcccgcca
tctgatgagcagttgaaatctggaactgcctctgttgtgtgcctgctgaataacttctatcccagagag
gccaaagtacagtggaaggtggataacgccctccaatcgggtaactcccaggagagtgtcacag
agcaggacagcaaggacagcacctacagcctcagcagcaccctgacgctgagcaaagcagac
tacgagaaacacaaagtctacgcctgcgaagtcacccatcagggcctgagctcgcccgtcacaa
agagcttcaacaggggagagtgt (SEQ ID NO:11)

4 species of glycan-occupancy on the heavy chain of Antibody 5.948.1

Glycan-Occupancy Profile of Antibody 5.948.1 on Day 14 of process without inhibitor Glycan-Occupancy Profile of Antibody 5.948.1 on Day 14 of process with inhibitor (2-deoxy-D-glucose)

Glycan-Occupancy Profile Detail Comparison of Antibody 5.948.1 on Day 14 with and without inhibitor (2-Deoxy-D-glucose)

Glycan-Occupancy Profile Comparison of Antibody 5.948.1 without inhibitor (2-deoxy-D-glucose) on day 7 (S5), day 12 (S6) & day 14 (S7) of the process Glycan-Occupancy Profile of Antibody 5.948.1 on Day 14 of process with no inhibitor, Deglycosylated and Denatured

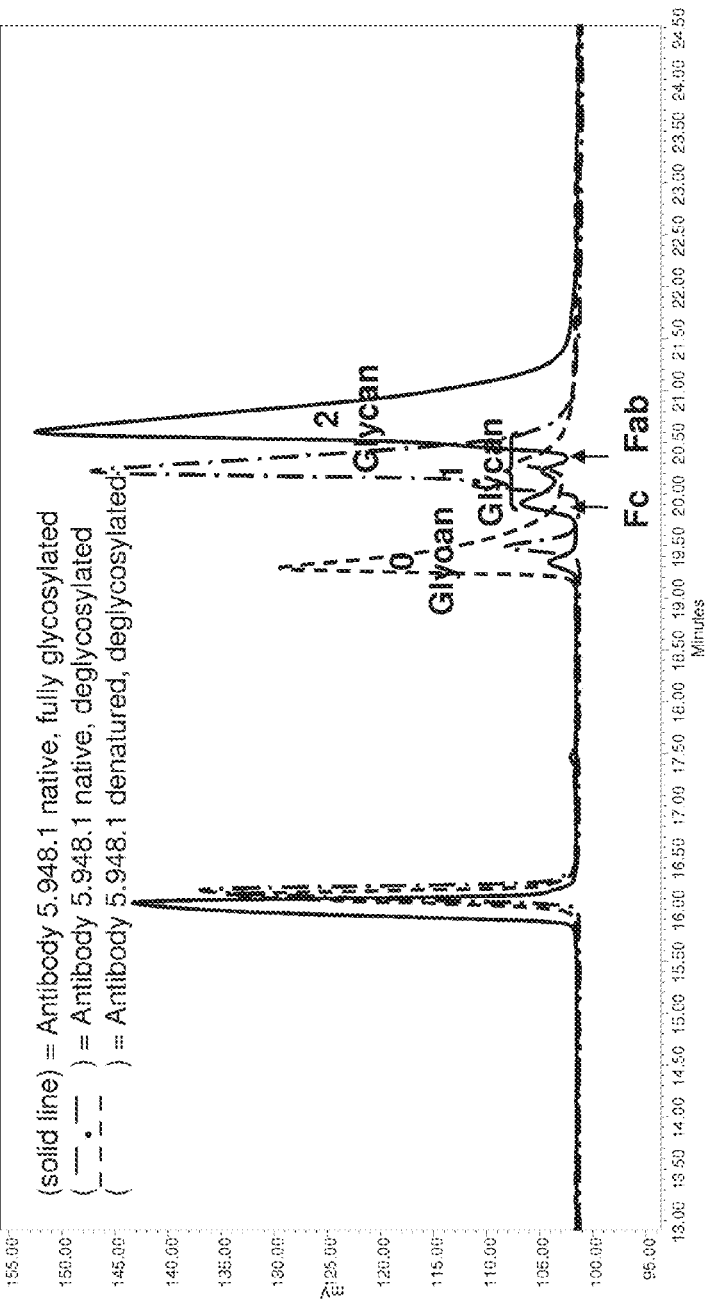

US 9,034,341 B2

CONTROL OF RAGE FUSION PROTEIN GLYCOSYLATION AND RAGE FUSION PROTEIN COMPOSITIONS

CROSS-REFERENCE TO RELATED APPLICATIONS

This application claims priority under 35 U.S.C. §120 as a United States national stage entry of International Application No. PCT/IB2010/051650, filed Apr. 15, 2010, which claims priority under U.S.C. §119(e) to U.S. Provisional Patent Application No. 61/170,897, filed Apr. 20, 2009, which is herein incorporated by reference in its entirety.

SEQUENCE LISTING

This application contains a Sequence Listing submitted as an electronic text file named "PC33848A_ST25.txt", having a size in bytes of 24,754, and created on Jun. 20, 2011. The information contained in this electronic file is hereby incorporated by reference in its entirety.

BACKGROUND OF THE INVENTION

The present invention relates to methods for controlling glycosylation of proteins and compositions and methods relating thereto. The invention further relates to methods of decreasing glycosylation and/or the glycan site occupancy of glycoproteins thereby affecting their biological characteristics and/or functions. The invention also relates to compositions produced using the methods of the invention to control glycosylation and uses thereof.

Proteins and polypeptides have become increasingly important therapeutic agents. In most cases, these proteins and polypeptides are produced in cell culture, from cells that have been engineered and/or selected to produce unusually high levels of the particular protein or polypeptide of interest. Control and optimization of cell culture conditions is critically important for successful commercial production of proteins and polypeptides.

Many proteins and polypeptides produced in cell culture are glycoproteins that contain covalently linked carbohydrate structures including oligosaccharide chains. These oligosaccharide chains are linked to the protein in the endoplasmic reticulum and the Golgi apparatus via either N-linkages or O-linkages. The oligosaccharide chains may comprise a significant portion of the mass of the glycoprotein. The oligosaccharide chains are thought to play key roles in the function of the glycoprotein including facilitating correct folding of the glycoprotein, mediating protein-protein interactions, conferring stability, conferring advantageous pharmacodynamic and/or pharmacokinetic properties, inhibiting proteolytic digestion, targeting the glycoprotein to the proper secretory pathway and targeting the glycoprotein to a particular organ or organs.

Generally, N-linked oligosaccharide chains are added to the nascent, translocating protein in the lumen of the endoplasmic reticulum (see Alberts et al., 1994, In: Molecular Biology of the Cell, incorporated herein by reference). The oligosaccharide is added to the amino group on the side chain of an asparagine residue contained within the target consensus sequence of Asn-X-Ser/Thr, where X may be any amino acid except proline. The initial oligosaccharide chain is usually trimmed by specific glycosidase enzymes in the endoplasmic reticulum, resulting in a short, branched core oligosaccharide composed of two N-acetylglucosamine and three mannose residues.

After initial processing in the endoplasmic reticulum, the glycoprotein is shuttled via small vesicles to the Golgi apparatus, where the oligosaccharide chain undergoes further processing before being secreted to the cell surface. The trimmed N-linked oligosaccharide chain may be modified by the addition of several mannose residues, resulting in a high-mannose oligosaccharide. Alternatively, one or more monosaccharides units of N-acetylglucosamine may be added to the core mannose subunits to form complex oligosaccharides. Galactose may be added to the N-acetylglucosamine subunits, and sialic acid subunits may be added to the galactose subunits, resulting in chains that terminate with either a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

In addition to being modified by the N-linked glycosylation pathway, glycoproteins may also be modified by the addition of O-linked oligosaccharide chains to specific serine or threonine residues as they are processed in the Golgi apparatus. The residues of an O-linked oligosaccharide are added one at a time and the addition of each residue is catalyzed by a specific enzyme. In contrast to N-linked glycosylation, the consensus amino acid sequence for O-linked glycosylation is less well defined.

Glycosylation of proteins, especially immunoglobulins, has been shown to have significant effects on their biological functions. For instance, for immunoglobulins, glycosylation has been demonstrated to affect effector functions, structural stability, and rate of secretion from antibody-producing cells (Leatherbarrow et al., 1985, Mol. Immunol. 22:407). The carbohydrate groups responsible for these properties are generally attached to the constant (C) regions of the antibodies. For example, glycosylation of IgG at asparagine 297 in the $C_H2$ domain is required for full capacity of IgG to activate the classical pathway of complement-dependent cytolysis (Tao and Morrison, 1989, J. Immunol. 143:2595). Glycosylation of IgM at asparagine 402 in the $C_H3$ domain is necessary for proper assembly and cytolytic activity of the antibody (Muraoka and Shulman, 1989, J. Immunol. 142:695). Removal of glycosylation sites as positions 162 and 419 in the $C_H1$ and $C_H3$ domains of an IgA antibody led to intracellular degradation and at least 90% inhibition of secretion (Taylor and Wall, 1988, Mol. Cell. Biol. 8:4197).

Glycosylation of immunoglobulins in the variable (V) region, comprising the antigen binding site, has also been observed. Sox and Hood (1970, Proc. Natl. Acad. Sci. USA 66:975), reported that about 20% of human antibodies are glycosylated in the V region. Glycosylation of the V domain is believed to arise from fortuitous occurrences of the N-linked glycosylation signal Asn-Xaa-Ser/Thr in the V region sequence and has not been recognized in the art as playing an important role in immunoglobulin function.

More recently, it has been demonstrated that glycosylation at CDR2 of the heavy chain, in the antigen binding site, of a murine antibody specific for alpha-(1-6)dextran increases its affinity for dextran (Wallick et al., 1988, J. Exp. Med. 168:1099; and Wright et al., 1991, EMBO J. 10:2717). It has also been demonstrated that mutation to remove a glycosylation site within the antigen binding site of an anti-CD33 antibody, more specifically, removal of an N-linked glycosylation site within a framework region of the V domain of the antibody M195, enhanced antibody binding with the antigen (U.S. Pat. No. 6,350,861, to Co et al.). However, the N-linked glycosylation site present in the Fc portion of the antibody was not removed and was, preferably, glycosylated to maintain the effector function of the molecule.

Additionally, glycolysis-inhibiting substances have been added to cell culture medium to reduce accumulation of the metabolic waste product lactate thereby increasing cell viability and protein production of antibodies. See, e.g., International Patent Application No. PCT/US2007/083473 now published as WO 2008/055260 on May 8, 2008 (addition of glycolysis inhibiting compound to cell culture reduced lactate concentration and increased production of antibody specific for growth and differentiation factor 8 (GDF-8)). While glycolysis-inhibition may also have affected the level of protein glycosylation, the effect of the inhibitor on protein glycosylation was not assessed or even discussed. Moreover, the anti-GDF-8 antibodies produced in cell culture did not comprise any potential glycosylation site in the antigen binding site (see WO 2008/055260 at page 49, paragraph 170, citing Veldman et al., U.S. Patent Publication No. 2004/0142382, describing the anti-GDF-8 antibodies Myo22, Myo28 and Myo29). Thus, even assuming the glycosylation of the anti-GDF-8 antibody at the heavy chain constant domain was affected under the culture conditions disclosed, no effect of altered glycosylation of the antigen binding site could have been assessed since it appears that the antibodies produced lacked a potential glycosylation site in the antigen binding region (e.g., the V domain).

A major problem with protein therapeutics has been reduced or low affinity for the ligand or antigen. Loss of or decreased affinity is highly undesirable, and requires that more of the therapeutic protein will have to be injected into the patient, at higher cost and greater risk of adverse effects. Even more critically, protein with reduced affinity may have decreased biological functions, such as complement lysis, antibody-dependent cellular cytotoxicity, and virus neutralization. Further, the protein may have decreased antagonist function by way of decreased competition between the antigen or binding partner and the therapeutic protein compared with the endogenous ligand or binding partner the interaction of which is sought to be inhibited. For example, the loss of affinity in the partially humanized antibody HUVHCAMP may have caused it to lose all ability to mediate complement lysis (see, Riechmann et al., 1988, Nature, 332, 323-327, at Table 1).

Further, given the unpredictability of protein conformation, mutation of even a single amino acid, especially at the antigen binding site or ligand binding site of the protein can have drastic effects on the biological activity of a potential therapeutic protein.

Thus, there exists a need in the art for therapeutic proteins that have an altered affinity for a ligand or, in the case of an antibody, an antigen, particularly an increased affinity and/or increased specificity for an antigen or ligand, and, desirably, potentially lower immunogenicity and improved effector function conferred by naturally-occurring constant region glycosylation. Alternatively, there exists a need for a therapeutic protein, especially an antibody or an Fc fusion protein comprising an immunoglobulin constant region, or a portion thereof, having improved binding affinity and/or specificity for an antigen or a ligand, but which has decreased or no effector function mediated by glycosylation of the glycosylation site present in the antibody heavy chain constant region. There is a further need to inhibit or remove glycosylation of a therapeutic protein antigen or ligand binding site without the need to introduce any mutation into the amino acid sequence of the antigen or ligand binding site. Thus, there exists a need in the art for methods to increase the efficacy and reduce the required doses of immunoglobulins and other proteins of therapeutic importance, and for therapeutic proteins produced by such methods, and the present invention meets these needs without requiring the introduction of any mutation into the antigen binding site of an antibody or the ligand binding site of a therapeutic protein.

Despite the importance of therapeutic glycoproteins and the advances in cell culture processes, there is an unmet need for novel processes for producing such proteins under conditions where glycosylation of the ligand binding site may be controlled without requiring the introduction of an amino acid mutation into such a critical portion of the protein. The present invention meets this need.

SUMMARY OF THE INVENTION

The present invention includes a method for decreasing the glycosylation level of a protein. The method comprises expressing a protein comprising at least one glycosylation site in a host cell grown in culture in the presence of a glycosylation inhibiting amount of a glycosylation inhibitor, wherein the protein comprises a lower level of glycosylation compared with an otherwise identical protein produced in an otherwise identical host cell grown under otherwise identical conditions in the absence of the inhibitor, thereby controlling the glycosylation level of the protein.

In one aspect, the glycosylation site is in a ligand binding site or an antigen binding site.

In another aspect, the glycosylation level is selected from the group consisting of glycan site occupancy at the glycosylation site and the extent of glycosylation at the glycosylation site.

In yet another aspect, the glycosylation site is selected from the group consisting of an O-linked glycosylation site and an N-linked glycosylation site.

In a further aspect, the glycosylation site is an N-linked glycosylation site, and further wherein the glycosylation site comprises the amino acid sequence asparagine-X-serine or asparagine-X-threonine where X is any amino acid except proline.

In another aspect, the glycosylation inhibitor is at least one inhibitor selected from the group consisting of tunicamycin, a tunicaymycin homolog, streptovirudin, mycospocidin, amphomycin, tsushimycin, antibiotic 24010, antibiotic MM 19290, bacitracin, corynetoxin, showdomycin, duimycin, 1-deoxymannonojirimycin, deoxynojirimycin, N-methyl-1-dexoymannojirimycin, brefeldin A, a glucose analog, a mannose analog, 2-deoxy-D-glucose, 2-deoxyglucose, D-(+)-mannose, D-(+) galactose, 2-deoxy-2-fluoro-D-glucose, 1,4-dideoxy-1,4-imino-D-mannitol (DIM), fluoroglucose, fluoromannose, UDP-2-deoxyglucose, GDP-2-deoxyglucose, a hydroxymethylglutaryl-CoA reductase inhibitor, 25-hydroxycholesterol, hydroxycholesterol, swainsonine, cycloheximide, puromycin, actinomycin D, monensin, m-Chlorocarbonyl-cyanide phenylhydrazone (CCCP), compactin, dolichyl-phosphoryl-2-deoxyglucose, N-Acetyl-D-Glucosamine, hygoxanthine, thymidine, cholesterol, glucosamine, mannosamine, castanospermine, glutamine, bromoconduritol, conduritol epoxide, a conduritol derivative, aglycosylmethyl-p-nitrophenyltriazene, β-Hydroxynorvaline, threo-β-fluoroasparagine, D-(+)-Gluconic acid δ-lactone, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl] trimethyl ammonium iodide, iodoacetate, and fluoroacetate.

In another aspect, the glycosylation inhibitor is 2-deoxy-D-glucose.

In yet another aspect, the glycosylation inhibiting amount ranges from about 0.5 g/L to 3 g/L.

In a further aspect, the method further comprises maintaining the glucose concentration in the culture in an amount ranging from about 0.05 g/L to 10 g/L.

In another aspect, the host cell is selected from the group consisting of a yeast cell, an insect cell, and a mammalian cell.

In yet another aspect, the mammalian host cell is selected from the group consisting of a CHO cell, an NS0 cell, NS0/1, Sp2/0, a human cell, HEK 293, BHK, COS, Hep G2, PER.C6, COS-7, TM4, CV1, VERO-76, MDCK, BRL 3A, W138, MMT 060562, TR1, MRC5, and FS4.

In yet a further aspect, the host cell is a CHO cell.

In another aspect, the glycosylation site is at least one glycosylation site comprising an amino acid sequence selected from the group consisting of asparagine-isoleucine-threonine (NIT), asparagine-glycine-serine (NGS), asparagine-serine-threonine (NST), and asparagine-threonine-serine (NTS).

The invention encompasses a protein produced according to a method for decreasing the glycosylation level of a protein where the method comprises expressing a protein comprising at least one glycosylation site in a host cell grown in culture in the presence of a glycosylation inhibiting amount of a glycosylation inhibitor, wherein the protein comprises a lower level of glycosylation compared with an otherwise identical protein produced in an otherwise identical host cell grown under otherwise identical conditions in the absence of the inhibitor, thereby controlling the glycosylation level of the protein, where the glycosylation site is a ligand binding site or an antigen binding site, where the glycosylation level is selected from the group consisting of glycan occupancy at the glycosylation site and the extent of glycosylation at the glycosylation site, where the glycosylation site is selected from the group consisting of an O-linked glycosylation site and an N-linked glycosylation site, where the glycosylation site is at least one glycosylation site comprising an amino acid sequence selected from the group consisting of asparagine-isoleucine-threonine (NIT), where the glycosylation inhibitor is 2-deoxy-D-glucose, the glycosylation inhibiting amount ranges from about 0.5 g/L to 3 g/L, the method comprises maintaining the glucose concentration in the culture in an amount ranging from about 0.05 g/L to 10 g/L, where the host cell is selected from the group consisting of a yeast cell, an insect cell and a mammalian cell.

In one aspect, the mammalian cell is a CHO cell and the asparagine-glycine-serine (NGS), asparagine-serine-threonine (NST), and asparagine-threonine-serine (NTS).

In another aspect, the protein is an antibody, or an antigen-binding portion thereof, and further wherein the antibody is an anti-human IgE antibody.

In another aspect, the antibody is a human antibody comprising a heavy chain variable region comprising the amino acid sequence of SEQ ID NO:8 and a light chain variable region having the amino acid sequence of SEQ ID NO:10.

In yet another aspect, the antibody comprises at least one N-linked glycosylation site that is not occupied and/or comprises at least one carbohydrate moiety less than the otherwise identical antibody produced in the absence of the glycosylation inhibitor wherein the site is selected from the group consisting of a glycosylation site at asparagine 73 (N73) and a glycosylation site at asparagine 301 (N301) of the heavy chain relative to the amino acid sequence of SEQ ID NO:8.

In a further aspect, the antibody comprises an N-linked glycosylation site at asparagine 73 that is not occupied.

In another aspect, the protein comprises the ligand binding site (LBS) of a receptor of advanced glycation endproducts (RAGE) comprising an amino acid sequence selected from the group consisting of SEQ ID NO: 13, SEQ ID NO:14 and SEQ ID NO:15.

In yet another aspect, the protein is a RAGE fusion protein comprising the amino acid sequence of SEQ ID NO:1 without the signal sequence which comprises from amino acid residue 1 through amino acid residue number 23, wherein said fusion protein lacks the terminal lysine residue (Lys438).

In a further aspect, the RAGE fusion protein comprises at least one N-linked glycosylation site that is not occupied and/or comprises at least one carbohydrate moiety less than an otherwise identical RAGE fusion protein produced in the absence of the glycosylation inhibitor wherein the site is at least one site selected from the group consisting of asparagine at amino acid residue number 2 (N2), asparagine at amino acid residue number 58 (N58), and asparagine at amino acid residue number 288 (N288), all with respect to the amino acid sequence of SEQ ID NO:1 without the signal sequence (amino acids 1 through 23).

In one aspect, the protein comprises at least two N-linked glycosylation sites that are not occupied and/or comprise at least one carbohydrate moiety less.

In another aspect, the protein comprises three N-linked glycosylation sites at least one of which is not occupied and/or comprises at least one carbohydrate moiety less.

In yet another aspect, the protein exhibits increased binding with an antigen compared with the otherwise identical protein produced in the absence of the inhibitor.

In a further aspect, the protein exhibits increased binding with a RAGE ligand compared with the otherwise identical protein produced in the absence of the inhibitor.

In one aspect, the method further comprises a temperature shift from a temperature ranging from about 34° C. to 39° C. to a temperature ranging from about 28° C. to 33° C.

In yet another aspect, the method comprises a temperature shift from a temperature ranging from about 34° C. to 37° C. to a temperature ranging from about 30.5° C. to 31.5° C.

The invention encompasses a pharmaceutical composition comprising a protein produced according to a method for decreasing the glycosylation level of a protein, where the method comprises expressing a protein comprising at least one glycosylation site in a host cell grown in culture in the presence of a glycosylation inhibiting amount of a glycosylation inhibitor, wherein the protein comprises a lower level of glycosylation compared with an otherwise identical protein produced in an otherwise identical host cell grown under otherwise identical conditions in the absence of the inhibitor, thereby controlling the glycosylation level of the protein, where the glycosylation site is in a ligand binding site or an antigen binding site, wherein the glycosylation level is selected from the group consisting of glycan site occupancy at the glycosylation site and the extent of glycosylation at the glycosylation site, wherein the glycosylation site is an N-linked glycosylation site comprising the amino acid sequence asparagine-X-serine or asparagine-X-threonine where X is any amino acid except proline, where the glycosylation inhibitor is 2-deoxy-D-glucose, where the glycosylation inhibiting amount ranges from about 0.5 g/L to 3 g/L, and the method further comprises maintaining the glucose concentration in the culture in an amount ranging from about 0.05 g/L to 10 g/L, and wherein the host cell is a CHO cell.

In another aspect, the glycosylation site is at least one glycosylation site comprising an amino acid sequence selected from the group consisting of asparagine-isoleucine-threonine (NIT), asparagine-glycine-serine (NGS), asparagine-serine-threonine (NST), and asparagine-threonine-serine (NTS).

The invention encompasses a composition comprising an amount of a fusion protein, wherein the fusion protein comprises a RAGE polypeptide linked to an immunoglobulin polypeptide, wherein the RAGE polypeptide comprises a fragment of human RAGE (SEQ ID NO: 3) wherein the fragment of human RAGE comprises a ligand binding site and at least one amino acid residue that may be glycosylated, wherein the immunoglobulin polypeptide comprises a $C_H2$ domain or a portion of a $C_H2$ domain of an immunoglobulin and a $C_H3$ domain of an immunoglobulin, and wherein the N-terminal residue of the immunoglobulin polypeptide is linked to the C-terminal residue of the RAGE polypeptide; and wherein at least 0.5% of the amount of the fusion protein is aglycosylated.

In one aspect, at least 30% of the total amount of the fusion protein is aglycosylated.

In another aspect, the percentage of the amount of the fusion protein in the fully glycosylated form is less than the percentage of the amount of the fusion protein in all of the non-fully glycosylated forms.

In yet another aspect, the fusion protein comprises at least three amino acid residues that may be glycosylated, wherein a first potential site of glycosylation is an amino acid residue of the RAGE ligand binding site, a second potential site of glycosylation is an amino acid residue of the RAGE polypeptide, and a third potential site of glycosylation is an amino acid residue of the immunoglobulin polypeptide.

The invention encompasses a composition comprising a protein comprising at least one potential glycosylation site, wherein the amount of fully glycosylated protein is less than the amount of less than fully glycosylated protein, and further comprising a pharmaceutically acceptable carrier.

In one aspect, the protein comprises two potential glycosylation sites, and where the amount of fully glycosylated protein is less than the combined amount of protein comprising one site that is not glycosylated and/or comprises a lower level of glycosylation and the amount of protein comprising two sites that are not glycosylated and/or comprise a lower level of glycosylation.

Alternate embodiments of the invention are described below, such as those employing various culture conditions, glycoproteins and involving different glycosylation inhibitors.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s) which are presently preferred. It should be understood, however, that the invention is not limited to the precise arrangements and instrumentalities shown.

In the drawings:

FIG. 1 is a diagram depicting construction of a sRAGE-Ig fusion protein. The Receptor for Advanced Glycation End products (RAGE) is shown with its three extracellular domains (V, C1 and C2), a transmembrane domain and an intracellular domain putatively responsible for RAGE signaling. A soluble or secreted form of RAGE encompassed by the terms "soluble RAGE" and "sRAGE" is depicted as lacking the transmembrane and intracellular domains. sRAGE may act as decoy receptor and is shown in the diagram as the RAGE extracellular domain only. A full-length human heavy chain IgG1 molecule is depicted showing the variable binding domain ($V_H$) which together with the first constant domain $C_H1$ forms an antibody binding fragment (Fab) which is joined to the second and third constant domains ($C_H2$ and $C_H3$) of the IgG1 molecule via a flexible hinge region. The diagram further depicts a sRAGE-Ig fusion protein constructed by linking the V and C1 domains of human RAGE to the $C_H2$ and $C_H3$ domains of an IgG1 molecule, either with or without (shown) the immunoglobulin hinge region.

FIG. 2, comprising FIGS. 2A and 2B, shows the amino and nucleic acid sequences of a sRAGE-Ig fusion protein of the invention. FIG. 2A sets forth the amino acid sequence of a sRAGE-Ig fusion protein of the invention (SEQ ID NO:1). The sRAGE-Ig protein sequence comprises 461 amino acids which includes a 23 amino acid signal peptide/leader sequence, which may be 22 amino acids in certain circumstances, that is cleaved during expression to produce the 438 amino acid mature protein (or 437 amino acids where the N-terminal lysine is clipped). For purposes of this example, the numbering of amino acid residues does not include the 23 amino acid leader sequence such that the sRAGE-Ig fusion protein sequence beings with glutamine at amino acid 1 (Q1) which can cyclize to form pyro-glutamic acid (pE) at amino acid one (pE1). The human RAGE sequence was derived from GenBank accession no. NM_001136. The three underlined asparagines (N) at positions N2, N58 and N288, indicate potential sites of N-linked glycosylation. The V domain of RAGE spans from amino acid residue number 1 through amino acid residue E109 The C1 domain of RAGE overlaps the C-terminal sequence of the V domain by about 10 amino acids and spans from about amino acid G99 to E220. Underlined amino acids RALR from amino acid residue 195 through amino acid residue 198 denotes the consensus sequence for furin cleavage. Approximately eight amino acid residues at the N-terminus of the C2 domain of sRAGE (PEG-GAVAP) overlaps the C-terminal sequence of the C1 domain such that the C1/C2 junction spans from about amino acid L212 to P228. The $C_H2$ and $C_H3$ domains of an IgG1 Fc are shown as encompassing from about P229 through K438 where the terminal lysine (K) is not clipped. In the embodiment shown, the fusion protein does not comprise the complete human hinge domain of IgG1. In another embodiment, the fusion protein can comprise the hinge or any portion thereof, including wherein the hinge, if present, may be modified to, for instance, alter any effector function otherwise associated with the unmodified hinge region. FIG. 2B shows a nucleic acid sequence (SEQ ID NO:2) encoding the sRAGE-Ig fusion protein comprising the amino acid sequence of SEQ ID NO:1. Coding sequence 1-753 highlighted in bold encodes RAGE N-terminal protein sequence whereas sequence 754-1386 encodes human IgG Fc (γ1) protein sequence without the hinge region.

10/300 GL column, ambient temperature, 0.75 mL/minute flow rate, 20 μL injection volume and 40 minute run time with monitoring at 280 nm. SEC enables the relative quantitation of homodimer, heterodimer, Fc dimer and high molecular mass species with the peak results shown in the inset at the upper left hand corner.

Figure 5:
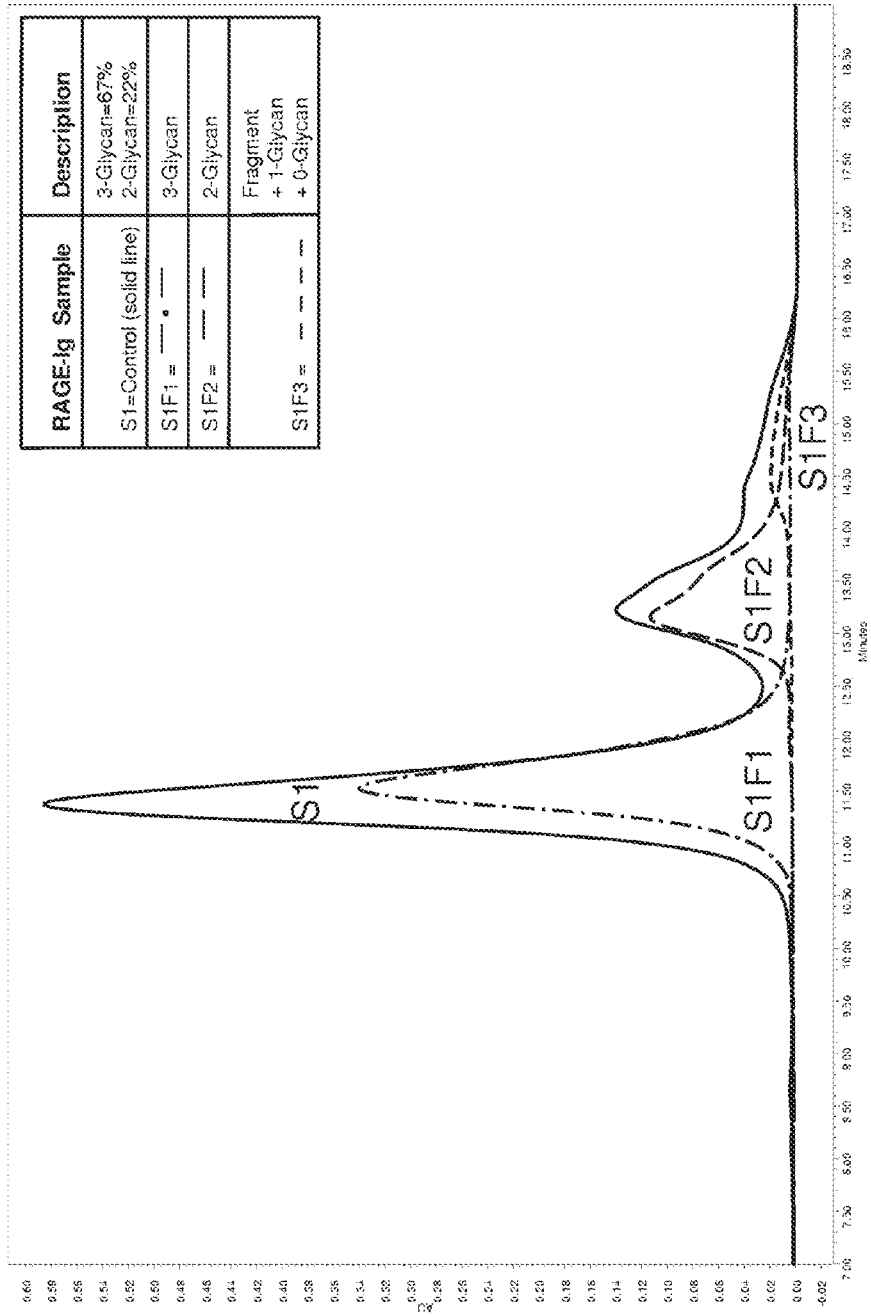

FIG. 5 shows the results of reversed phase-HPLC showing glycan site occupancy profile of sRAGE-Ig fusion protein. Overlayed chromatograms are the FLM of sRAGE-Ig fusion protein (S1) and the fractionated samples (S1F1, S1F2, and S1F3). Fraction S1F3 was extremely low in concentration, therefore it was not included in the subsequent ELISA binding assay. The inset at the upper right hand corner shows the approximate content of each glycan as a percentage of each sample/fraction.

Figure 6:
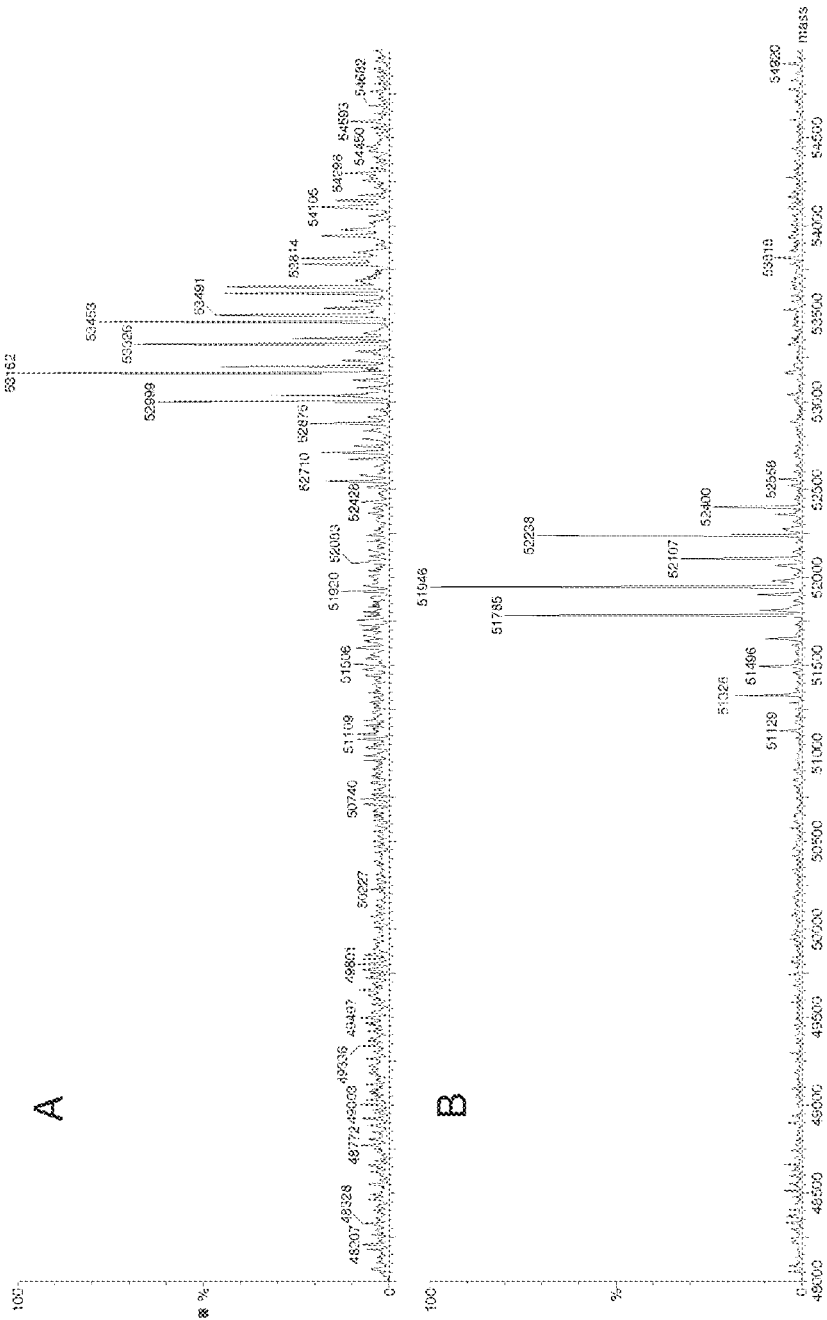

FIG. 6 is a diagram depicting the peak identity confirmation by mass spectrometry for peaks S1F1 and S1F2 shown in FIG. 5. Mass spectra data identify the peak S1F1 as 3-glycan species and S1F2 as 2-glycan species.

Figure 7:
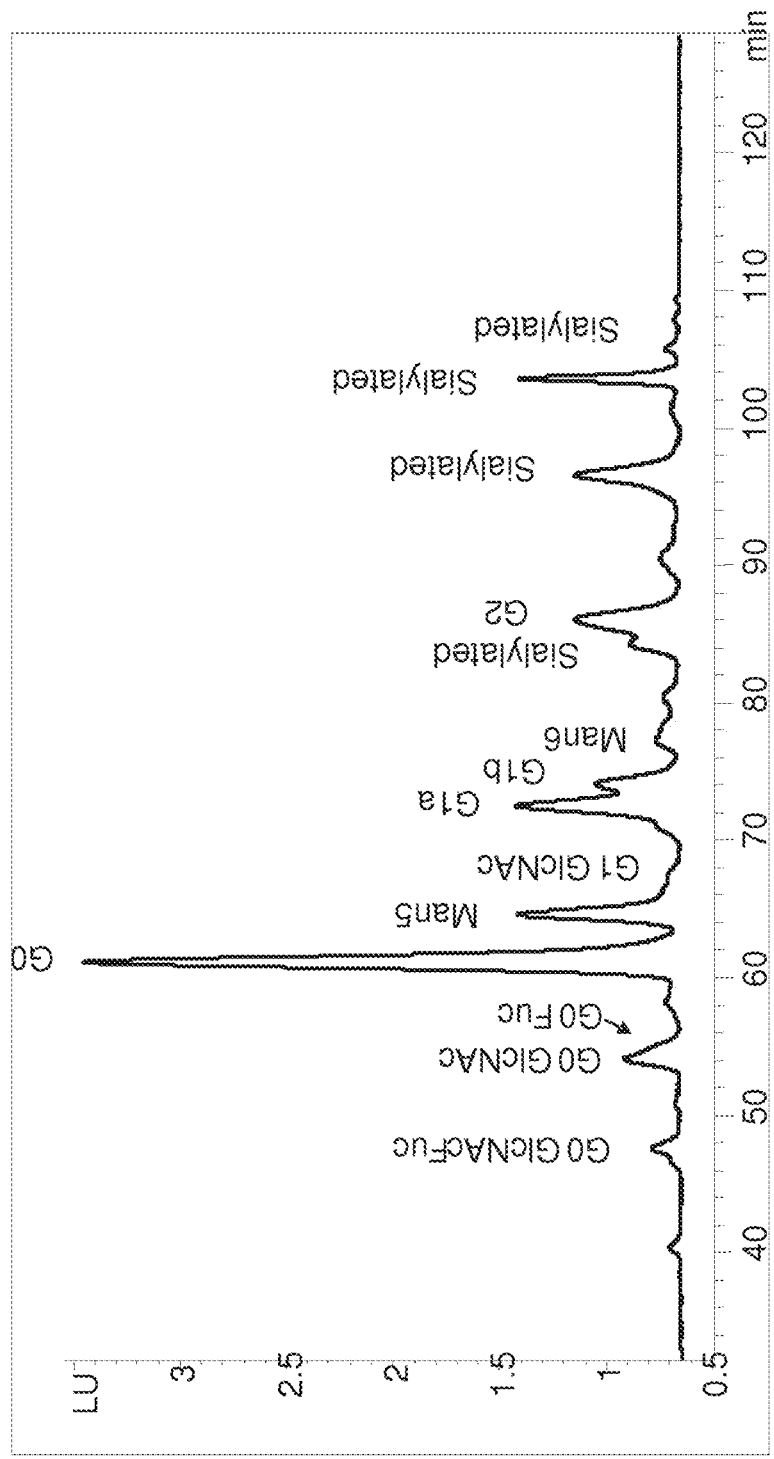

FIG. 7 is a diagram showing a normal phase HPLC analysis of the released N-linked glycans from sRAGE-Ig fusion with the peak identities indicated on the chromatogram. The relative abundances for the species are shown in Table 1.

Figure 8:
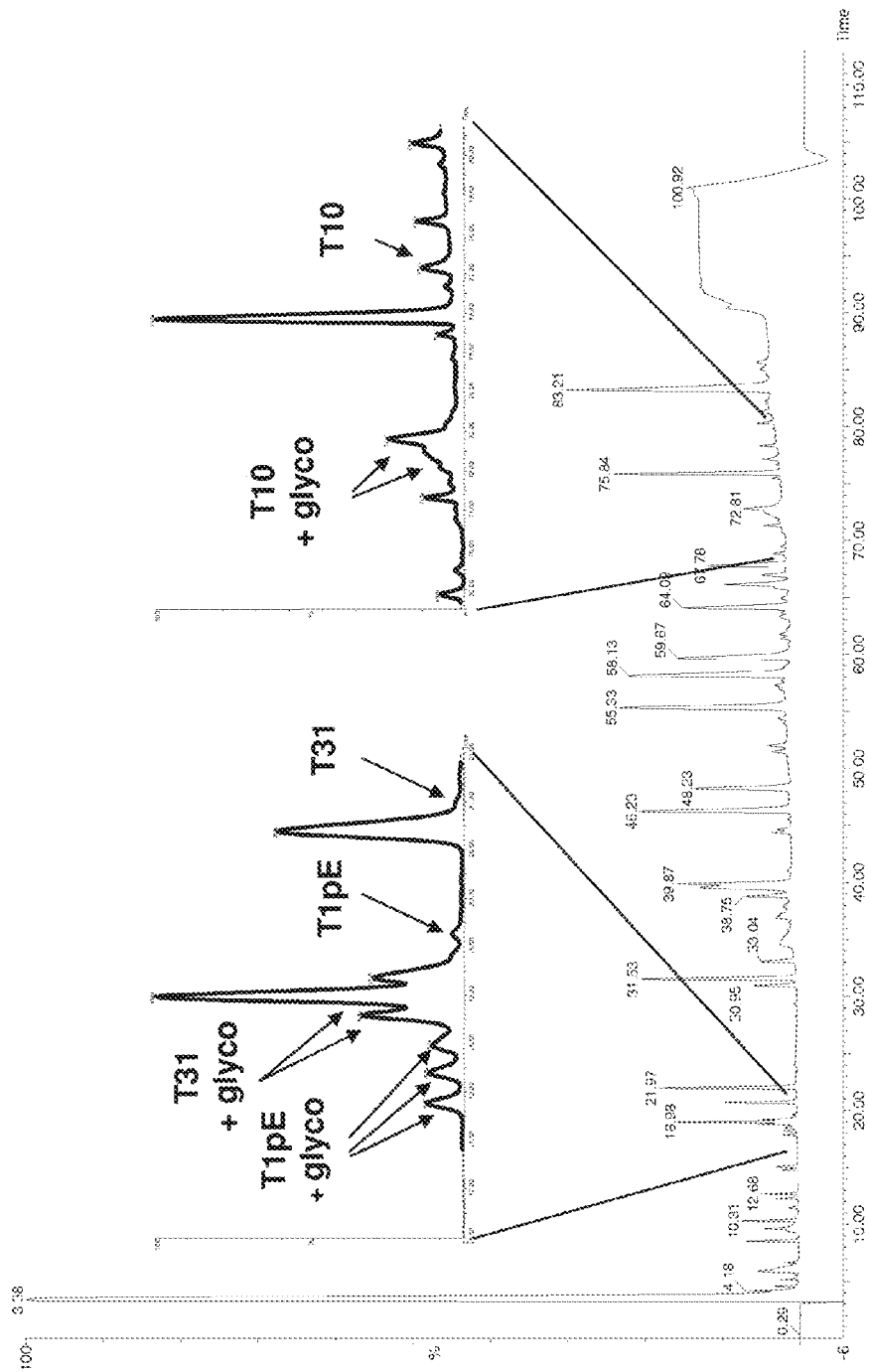

FIG. 8 is a diagram depicting the results of reversed-phase separation of the tryptic digest of sRAGE-Ig. The insets show the regions where the N-linked tryptic peptides elute.

FIG. 9 show the identity of tryptic peptides containing the consensus N-linked glycosylation sites, along with the theoretical monoisotopic molecular masses. The figure sets out the amino acid sequences of the three predicted tryptic glycopeptides from the sRAGE-Ig fusion protein digested with trypsin and show the theoretical monoisotopic molecular mass of each tryptic digest. The tryptic glycopeptides are as follows: T1pE (pENITAR) with a mass of about 638.36 Da; T10 (VLPNGSLFLPAVGIQDEGIFR) having a molecular mass of about 2241.22 Da; and T31 (EEQYNSTYR) with a molecular mass of about 1188.50 Da.

Figure 10:
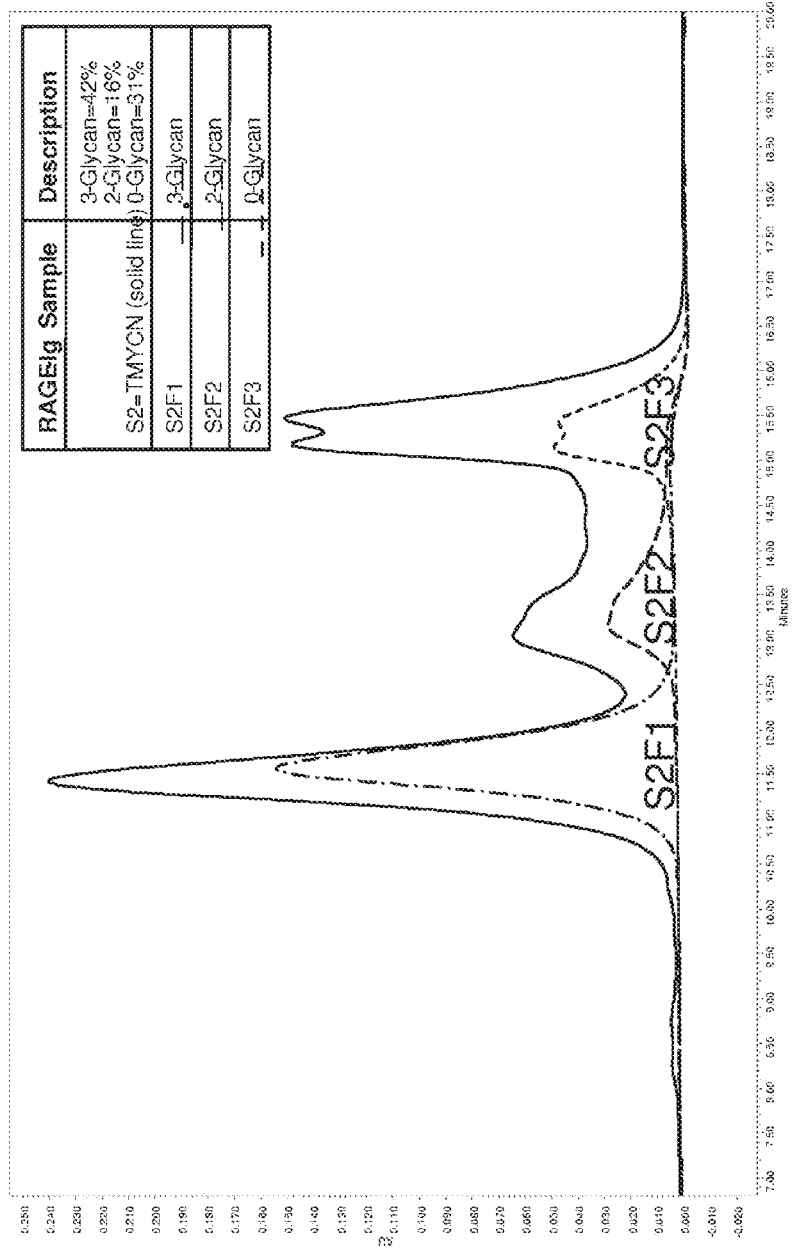

FIG. 10 is a diagram depicting a reversed phase-HPLC showing glycan site occupancy profile of sRAGE-Ig fusion protein expressed in the presence of tunicamycin. Overlayed chromatograms are the sRAGE-Ig fusion protein from tunicamycin treated cells (S2) and three fraction samples (S2F1, S2F1, and S2F3). The inset at the upper right hand corner sets out the relative percentage of each glycan in each sample or fraction thereof.

Figure 11:
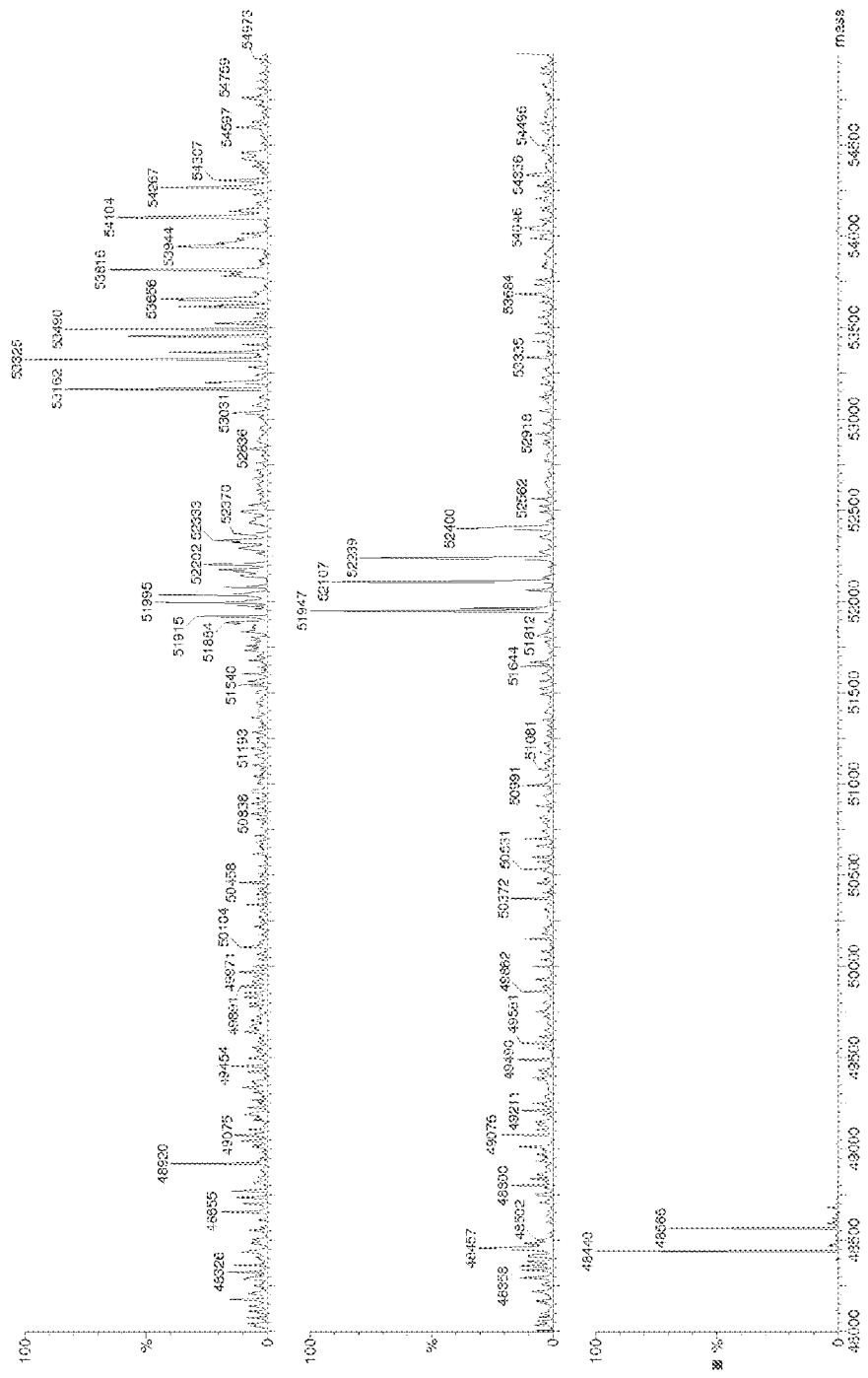

FIG. 11 is a diagram depicting peak identity confirmation by mass spectrometry for peaks S2F1, S2F2 and S2F3 shown in FIG. 10. Mass spectral data identify the peak S2F1 as 3-glycan species, S2F2 as 2-glycan species, and S2F3 as 0-glycan species.

Figure 12:
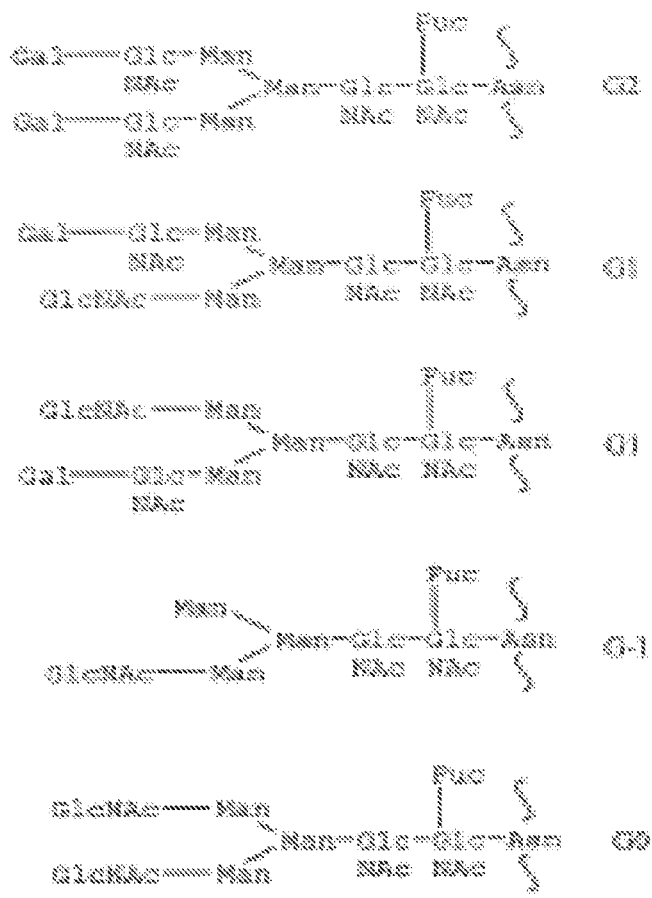

FIG. 12 is a diagram depicting exemplary biantennary glycoforms typically present in immunoglobulin heavy chain constant regions. According to the present invention, "G0" refers to a biantennary structure wherein no terminal sialic acids (NeuAcs) or Gals are present, "G1" refers to a biantennary structure having one Gal and no NeuAcs and "G2" refers to a biantennary structure with two terminal Gals and no NeuAcs.

FIG. 13, comprising FIGS. 13A through 13D, depicts the sequence of the heavy chain and the light chain of anti-IgE antibody 5.948.1. FIG. 13A depicts the amino acid sequence of mAb 5.948.1 heavy chain (SEQ ID NO:8). The variable domains are shown in lower case letters and the constant domains are show in uppercase letters. The complementarity determining regions (CDR) are underlined and the potential N-linked glycosylation site in the heavy chain variable region at asparagine 73 of framework 3 is shown in uppercase letters ("NTS"). The N-linked glycosylation site ("NST") in the heavy chain constant domain, Asn301, is underlined. FIG. 13B depicts the nucleic acid sequence encoding the heavy chain of mAb 5.948.1 (SEQ ID NO:9). FIG. 13C depicts the amino acid sequence of the mAb 5.948.1 light chain (SEQ ID NO:10). The variable domains are shown in lower case letters and the constant domains are show in uppercase letters. The complementarity determining regions (CDR) are underlined. FIG. 13D depicts the nucleic acid sequence encoding the light chain of mAb 5.948.1 (SEQ ID NO:11).

Figure 14:
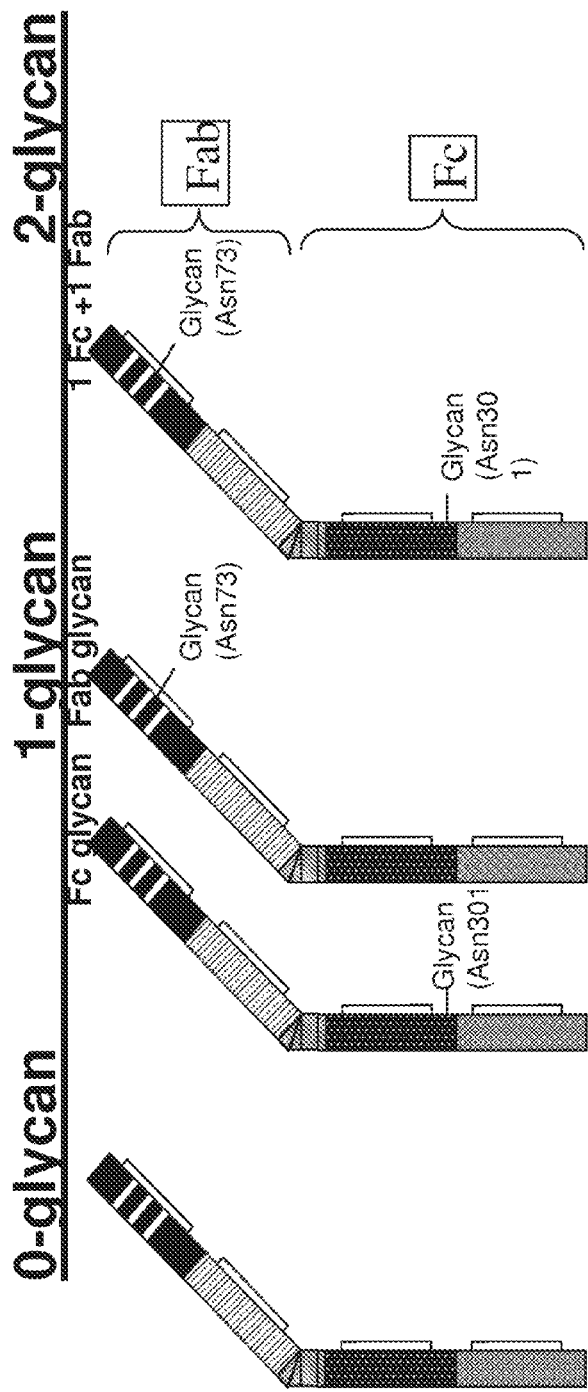

FIG. 14 is a diagram depicting the four possible glycan site occupancy variants for the heavy chain of antibody 5.948.1. The diagram shows, from left to right, the 0-glycan occupancy variant comprising no glycans at either Asn73 or Asn301; the 1-glycan occupancy variant comprising a glycan only at Asn301; the 1-glycan occupancy variant comprising a glycan only at Asn73; and the fully occupied 2-glycan occupancy site variant comprising glycans at both Asn73 and Asn301.

Figure 15:
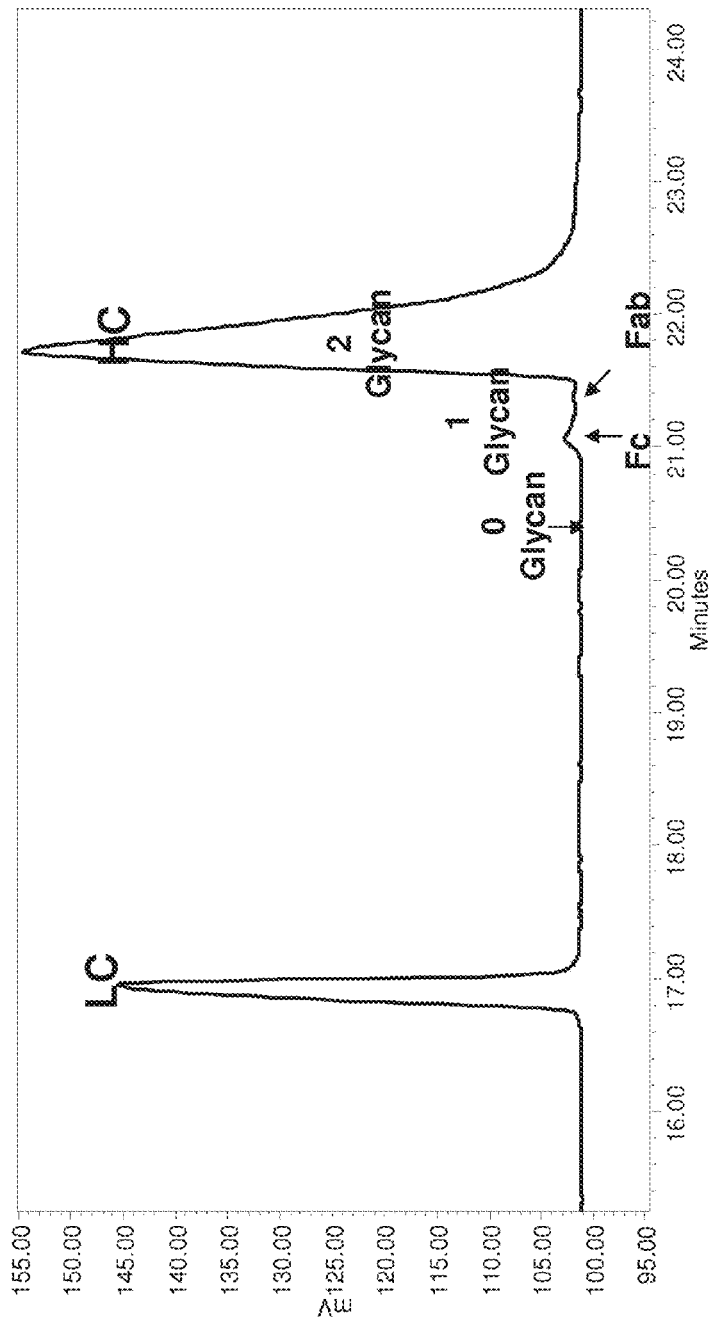

FIG. 15 is a diagram showing the glycan profile for antibody 5.948. The heavy chain was resolved into three peaks indicating the 2-glycan and 1-glycan variants. No 0-glycan occupancy variant was detected. The 1-glycan occupancy peak could be further resolved to identify a variant glycosylated in the Fc region (more prevalent) and a variant glycosylated in the Fab region of the antibody heavy chain. The data show that the fully glycosylated 2-glycan occupancy heavy chain comprises approximately 98% and the 1-glycan occupancy heavy chain comprises about 2% of the total heavy chain produced under control culture conditions.

Figure 16:
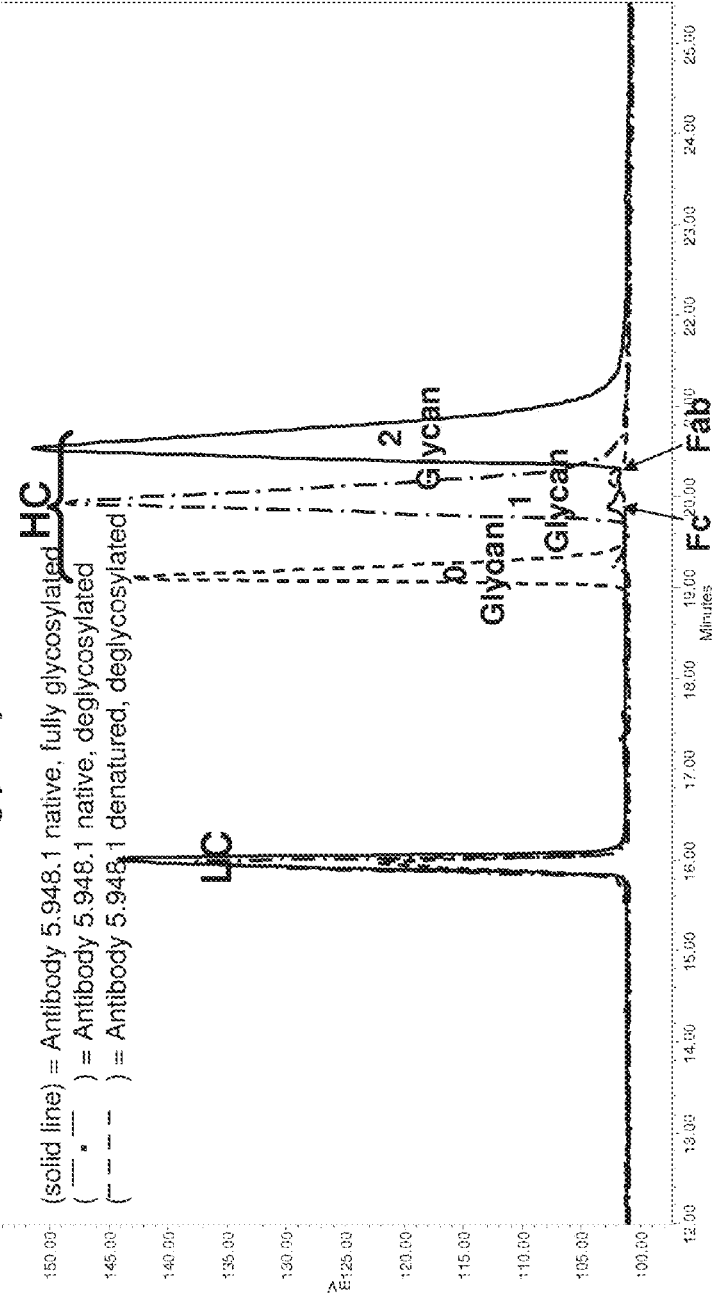

FIG. 16 is a diagram showing the glycan profile for the monoclonal antibody 5.948.1 (mAb 5.948.1) along side a sample of the 5.948.1 antibody that was deglycosylated with glycol-N-glycanase and a sample that was denatured using SDS and BME. The heavy chain for the native 5.948.1 antibody resolved as was previously seen (FIG. 15, supra) into three major peaks indicating the 2-glycan and 1-glycan variants. No 0-glycan occupancy variant was detected. The 1-glycan occupancy peak could be further resolved to identify a variant glycosylated in the Fc region and a variant glycosylated in the Fab region of the antibody heavy chain. The heavy chain of the native deglycosylated 5.948.1 antibody shows a profile that contains predominantly the 1-glycan species with some 0-glycan species. The heavy chain of the denatured deglycosylated 5.948.1 antibody shows a profile that contains predominantly the 0-glycan species.

Figure 17:
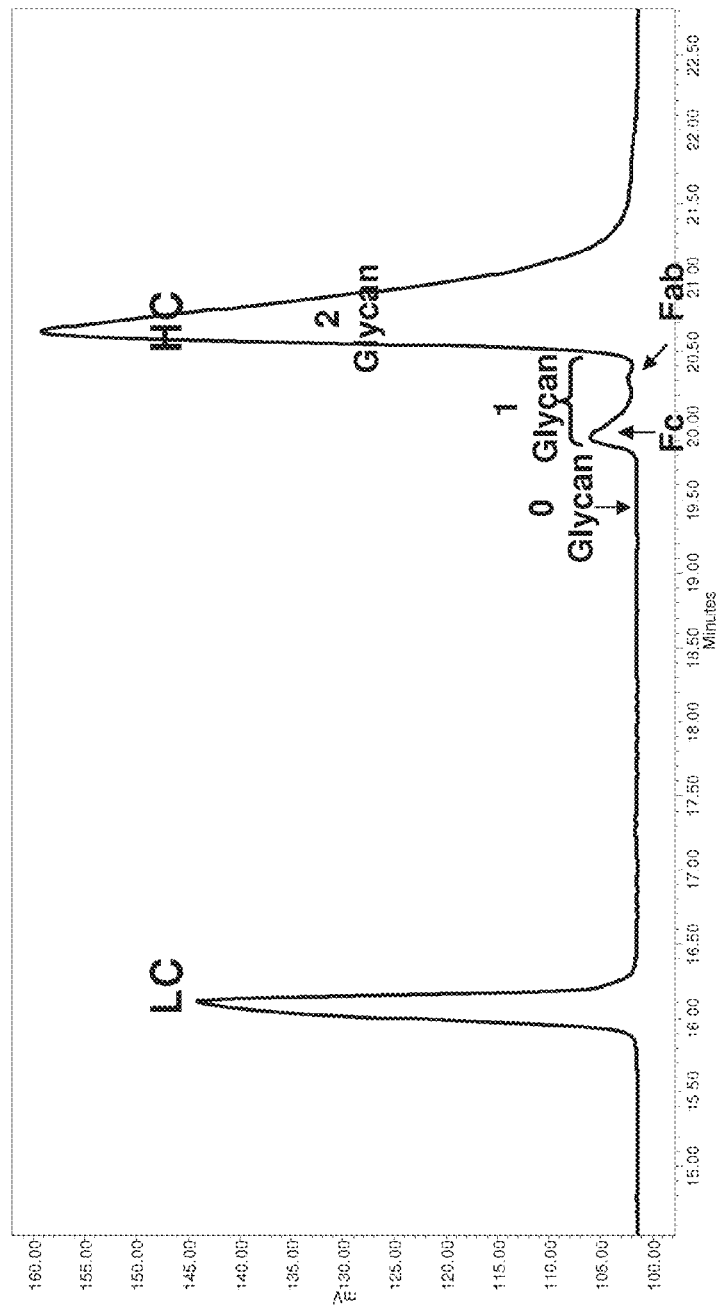

FIG. 17 is a diagram showing the glycan profile for antibody 5.948.1 produced under control conditions (i.e., in the absence of a glycosylation inhibitor) where the sample was taken from culture at day 14 (sample 7; S7). The heavy chain was resolved into three peaks indicating the 2-glycan and 1-glycan variants. No 0-glycan occupancy variant was detected. The 1-glycan occupancy peak could be further resolved to identify a variant glycosylated in the Fc region (more prevalent) and a variant glycosylated in the Fab region of the antibody heavy chain. The data show that the fully glycosylated 2-glycan occupancy heavy chain comprises approximately 98% and the 1-glycan occupancy heavy chain comprises about 2% of the total heavy chain produced under control culture conditions.

Figure 18:
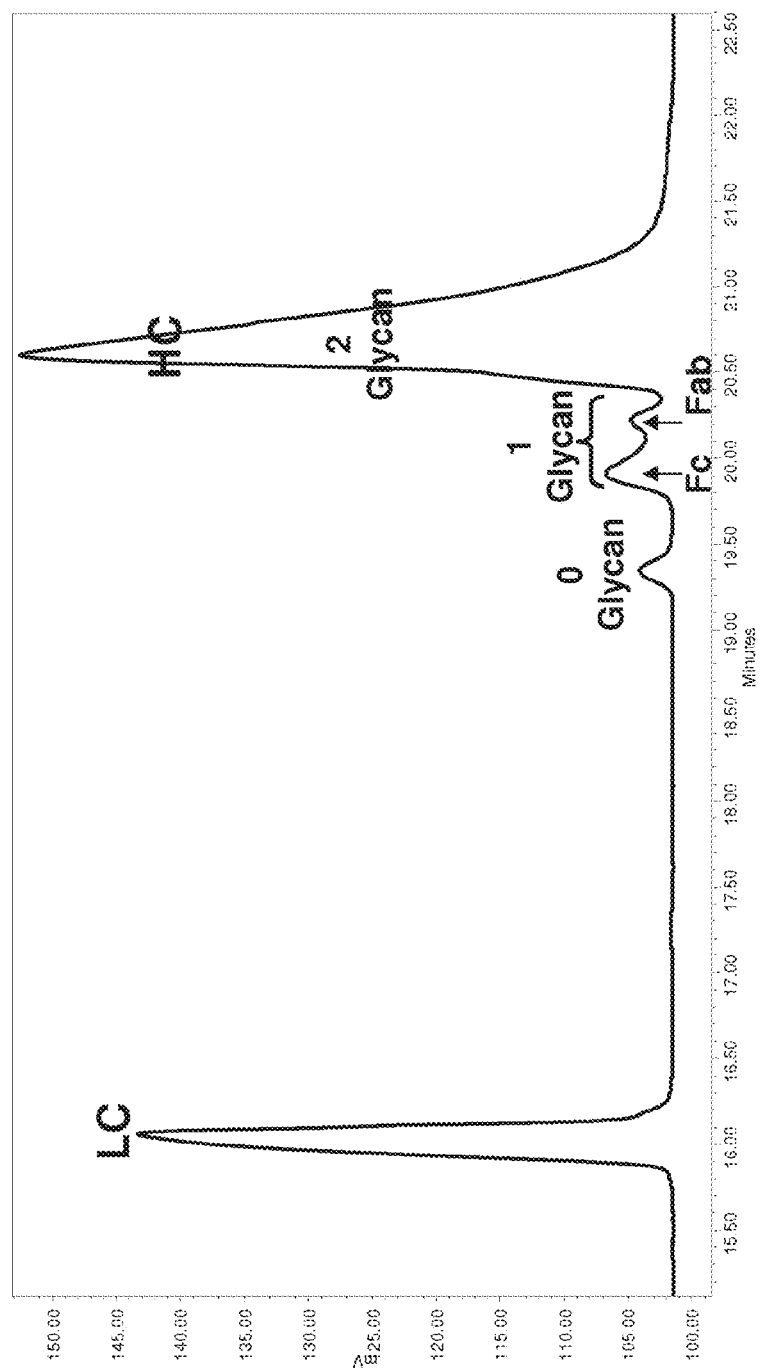

FIG. 18 is a diagram showing the glycan profile for antibody 5.948.1 produced in the presence of glycosylation inhibitor 2-deoxy-D-glucose where the sample was taken from culture at day 14 (sample 11; S11). The heavy chain was resolved into three peaks indicating the 2-glycan and 1-glycan variants. The 0-glycan occupancy variant was easily detected. The 1-glycan occupancy peak could be further resolved to identify a variant glycosylated in the Fc region (more prevalent) and a variant glycosylated in the Fab region of the antibody heavy chain.

Figure 19:
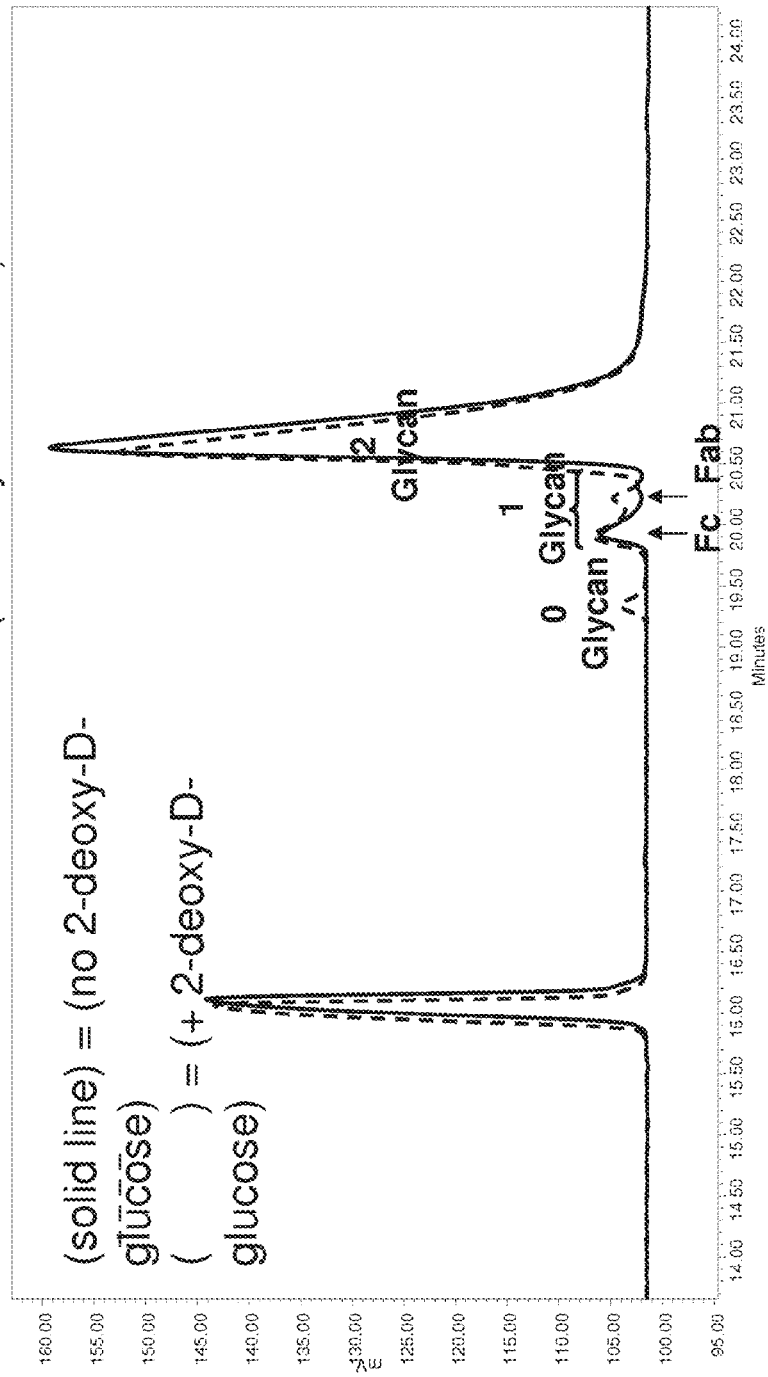

FIG. 19 is a diagram of a profile overlay comparing the glycan profile of mAb 5.948.1 produced under control conditions (in the absence of a glycosylation inhibitor) and the glycan profile of mAb 5.948.1 produced under glycosylation control conditions (i.e., in the presence of glycosylation inhibitor 2-deoxy-D-glucose) where the samples were taken from each culture at day 14 (S7 and S11, respectively). The heavy chain was resolved into four peaks indicating the 2-glycan, 1-glycan and 0-glycan variants. The 0-glycan occupancy variant was easily detected only in S11. The 1-glycan occupancy peak could be further resolved to identify a variant glycosylated in the Fc region (more prevalent) and a variant glycosylated in the Fab region of the antibody heavy chain. The data show that the 1-glycan Fab variant heavy chain is greatly increased relative to the 1-glycan Fc variant in 2-deoxy-D-glucose sample (S11) compared with the control sample (S7) where the 1-glycan variant is comprised mostly of the Fc variant.

Figure 20:
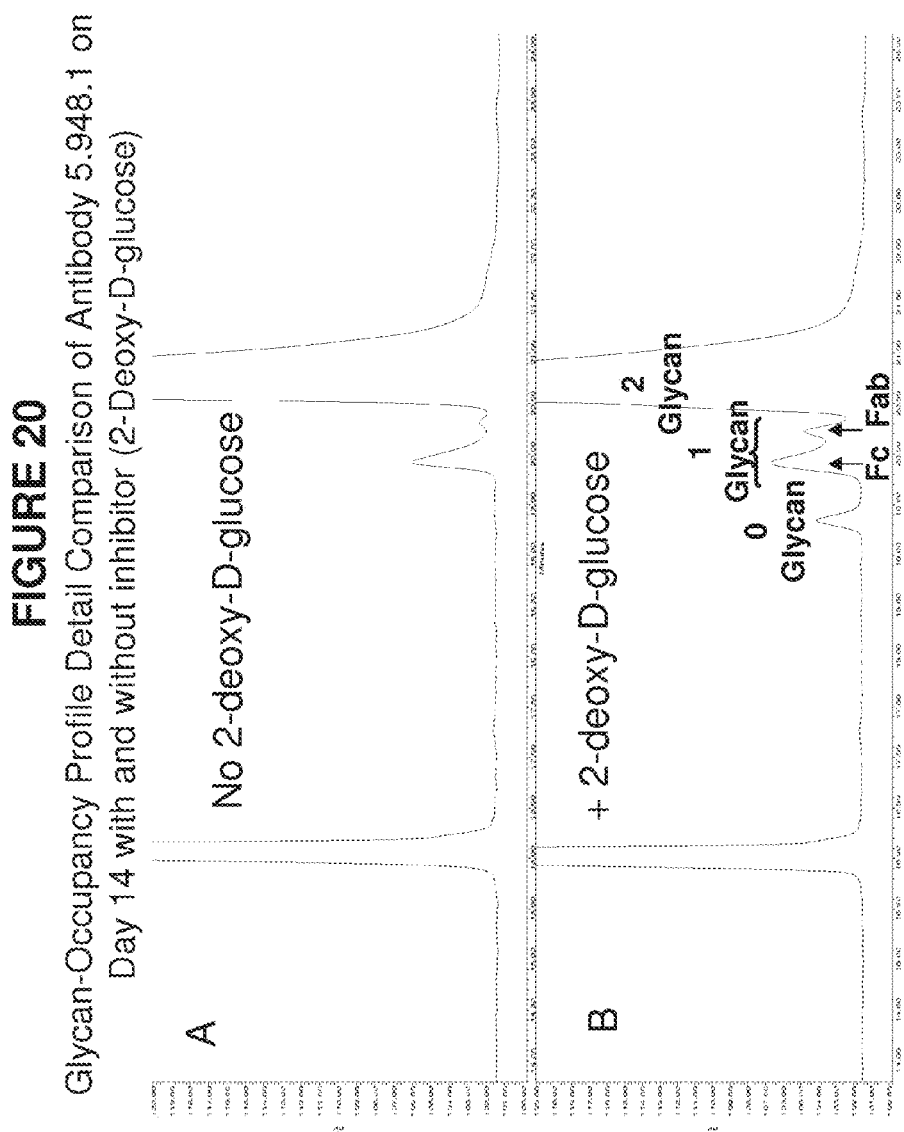

FIG. 20, comprising FIGS. 20A and 20B, is a diagram of the detail profile comparison comparing the glycan profile for antibody 5.948.1 produced in the absence and presence of a glycosylation inhibitor. FIG. 20A is a diagram showing the glycan profile for mAb 5.948.1 produced under control conditions (in the absence of a glycosylation inhibitor) where the sample was taken from culture at day 14 (S7). FIG. 20B is a diagram showing the glycan profile for mAb 5.948.1 produced in the presence of 2-deoxy-D-glucose where the sample was taken from culture at day 14 (S11). Comparison of FIG. 20A and FIG. 20B shows that the 0-glycan occupancy variant was easily detected only in S11. The 1-glycan occupancy peak could be further resolved to identify a variant glycosylated in the Fc region (more prevalent) and a variant glycosylated in the Fab region of the antibody heavy chain. The data show that the 1-glycan Fab variant heavy chain is greatly increased relative to the 1-glycan Fc variant in 2-deoxy-D-glucose sample (S11; FIG. 20B) compared with the control sample (S7; FIG. 20A) where the 1-glycan variant is comprised mostly of the Fc variant.

Figure 21:
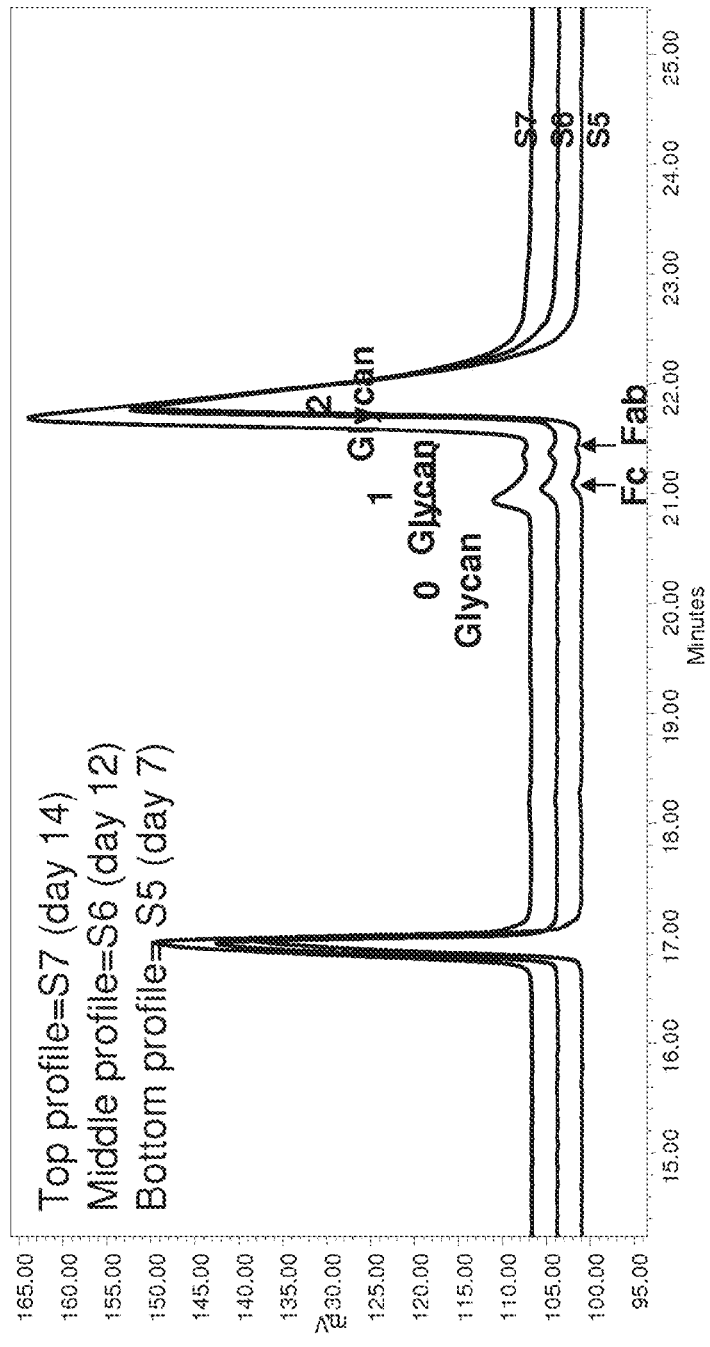

FIG. 21 is a diagram showing the glycan profile for mAb 5.948.1 produced under control conditions (i.e., in the absence of glycosylation inhibitor 2-deoxy-D-glucose) over the time course for the process. The diagram depicts three curves showing the glycan profiles of samples taken at day 7 (S5), day 12 (S6) and day 14 (S7) of culture. The data show that the relative amount of 1-glycan heavy chain glycosylated at the Fc region of the protein (Asn301) increases over time compared to the amount of 1-glycan heavy chain glycosylated at the Fab site (Asn73). The data further demonstrate that 0-glycan heavy chain is not detected in any sample taken at any time sampled.

Figure 22:
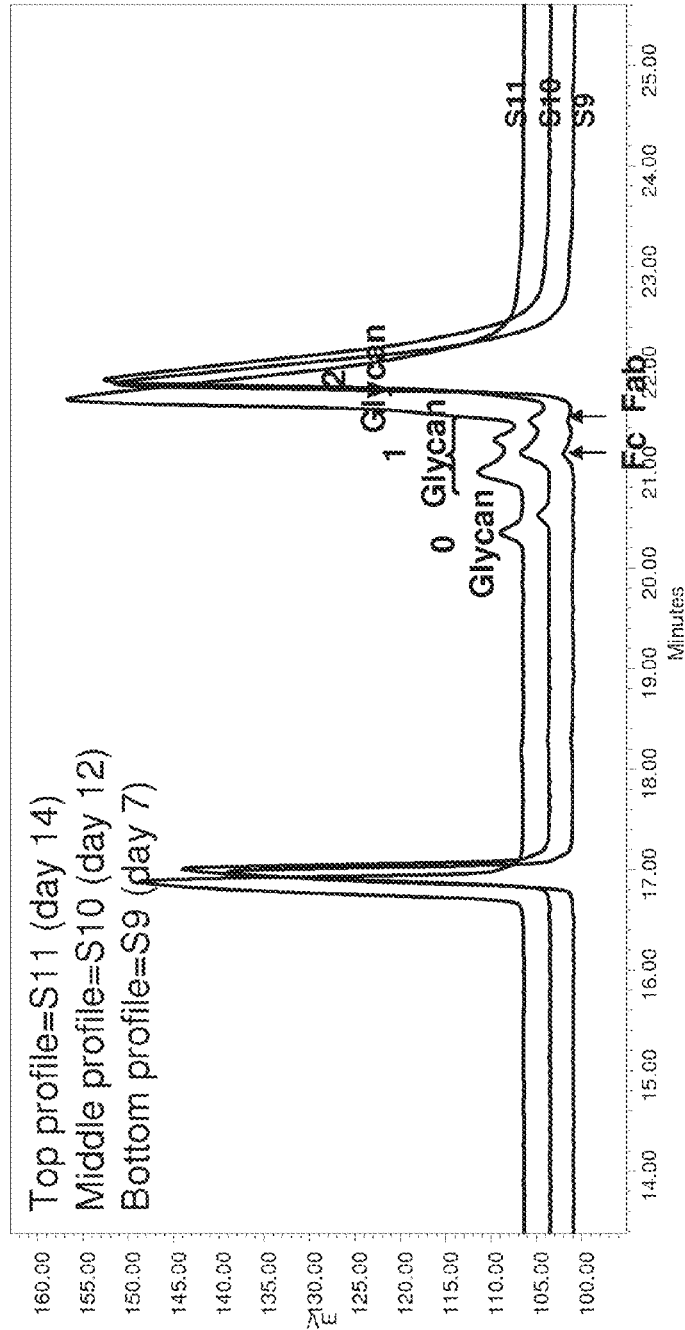

FIG. 22 is a diagram showing the glycan profile for mAb 5.948.1 produced in the presence of glycosylation inhibitor 2-deoxy-D-glucose over the time course for the process. The diagram depicts three curves showing the glycan profiles of samples taken at day 7 (S9), day 12 (S10) and day 14 (S11) of culture. The data show that the relative amount of 1-glycan heavy chain protein increases over time compared with the amount of 2-glycan heavy chain protein. Further, the data show that 1-glycan heavy chain protein glycosylated at the Fab region of the protein (Asn73) increases over time compared to the amount of 1-glycan heavy chain glycosylated at the Fc site (Asn301). This is the opposite of what is seen in the control sample where the Fc 1-glycan increases relative to the Fab 1-glycan during culture. The data further demonstrate that production of the 0-glycan heavy chain increases over time under glycosylation inhibiting conditions.

Figure 23:
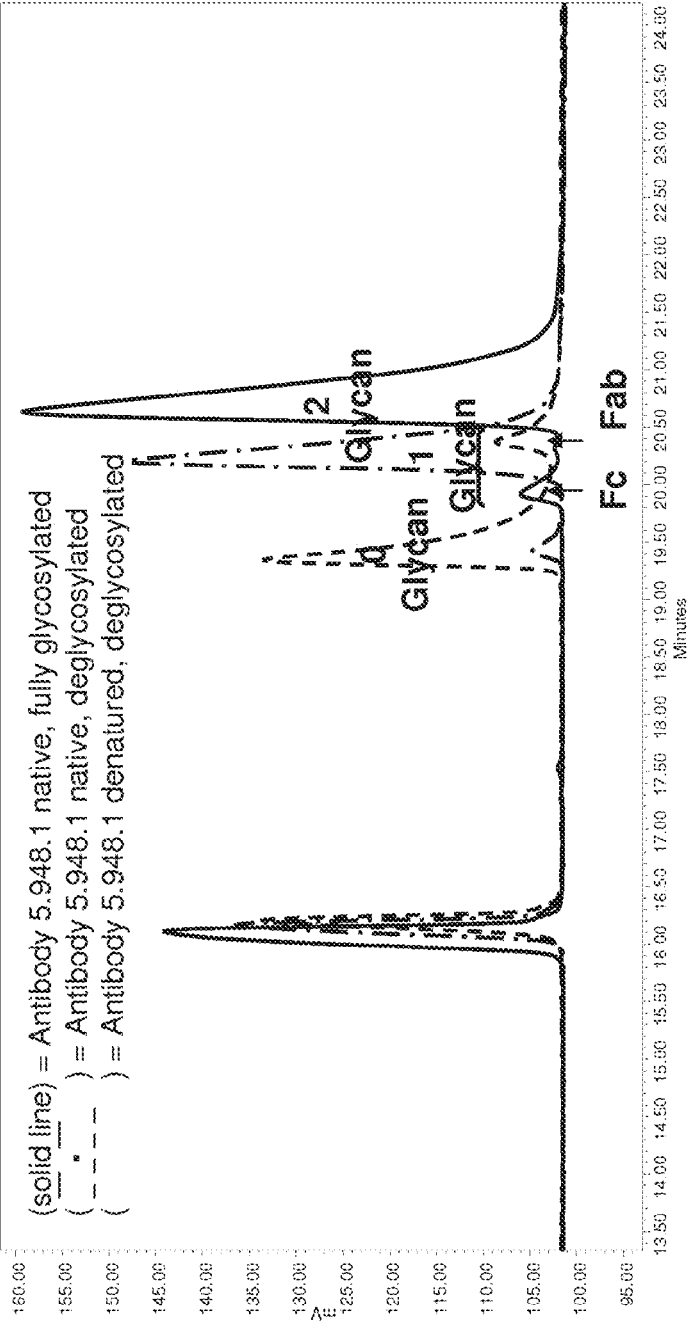

FIG. 23 is a diagram showing the glycan profile for the native antibody 5.948.1 (mAb 5.948.1) produced under control conditions (i.e., in the absence of a glycosylation inhibitor) where the sample was taken on day 14 of culture (S7) along side an equivalent sample of the 5.948.1 antibody that was deglycosylated with glycol-N-glycanase and a sample that was denatured using SDS and BME. The heavy chain for the native 5.948.1 antibody resolved as was previously seen into three major peaks indicating the 2-glycan and 1-glycan variants. No 0-glycan occupancy variant for this sample was detected in the absence of the glycosylation inhibitor 2-deoxy-D-glucose.

FIG. 24 is a diagram showing the glycan profile for the native antibody 5.948.1 (mAb 5.948.1) produced in the presence of glycosylation inhibitor 2-deoxy-D-glucose where the sample was taken on day 14 of culture (S7) (solid line) compared with an equivalent sample of the 5.948.1 antibody that was deglycosylated with glycol-N-glycanase (-•-) and a sample that was denatured using SDS and BME (- - -). The heavy chain for the native 5.948.1 antibody resolved into four peaks indicating the 2-glycan, 1-glycan and 0-glycan variants. The 0-glycan occupancy variant for this sample was easily detected and further demonstrates the production of the 0-glycan heavy chain in the presence of the glycosylation inhibitor 2-deoxy-D-glucose.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to methods well known in the art and as described in various general and more specific references that are cited and discussed throughout the present specification unless otherwise indicated. Such references include, e.g., Sambrook and Russell, 2001, In: Molecular Cloning, A Laboratory Approach, Cold Spring Harbor Press, Cold Spring Harbor, N.Y.; Ausubel et al., 2002, In: Current Protocols in Molecular Biology, John Wiley & Sons, NY; and Harlow and Lane, 1990, In: Antibodies: A Laboratory Manual, Cold Spring Harbor Laboratory Press, Cold Spring Harbor, N.Y., which are incorporated herein by reference. Enzymatic reactions and purification techniques are performed according to manufacturers specifications, as commonly accomplished in the art or as described herein. The nomenclatures used in connection with, and the laboratory procedures and techniques of, analytical chemistry, synthetic organic chemistry, cell and molecular biology, immunology, and medicinal and pharmaceutical chemistry described herein are those well known and commonly used in the art. Standard techniques are used for chemical syntheses, chemical analyses, pharmaceutical preparation, formulation, and delivery, and treatment of patients.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, 1994, Methods Mol. Biol. 243:307-31).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., 1992, Science 256:1443-1445, herein incorporated by reference. A "moderately conservative" replacement is any change having a nonnegative value in the PAM250 log-likelihood matrix.

Preferred amino acid substitutions are those which: (1) reduce susceptibility to proteolysis, (2) reduce susceptibility to oxidation, (3) alter binding affinity for forming protein complexes, and (4) confer or modify other physicochemical or functional properties of such analogs. Analogs comprising substitutions, deletions, and/or insertions can include various muteins of a sequence other than the specified peptide sequence. For example, single or multiple amino acid substitutions (preferably conservative amino acid substitutions) may be made in the specified sequence (preferably in the portion of the polypeptide outside the domain(s) forming intermolecular contacts, e.g., outside of the CDRs). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., 1991, Nature 354:105), which are each incorporated herein by reference.

Sequence similarity for polypeptides is typically measured using sequence analysis software. Protein analysis software matches similar sequences using measures of similarity assigned to various substitutions, deletions and other modifications, including conservative amino acid substitutions. For instance, Genetics Computer Group (GCG available from Genetics Computer Group, Inc.), also referred to as the Wisconsin Package, is an integrated software package of over 130 programs for accessing, analyzing and manipulating nucleotide and protein sequences. GCG contains programs such as "Gap" and "Bestfit" which can be used with default parameters to determine sequence similarity, homology and/or sequence identity between closely related polypeptides, such as homologous polypeptides from different species of organisms or between a wild type protein and a mutein thereof. See, e.g., GCG version 6.1, version 7.0, version 9.1, and version 10.0.

Polypeptide sequences also can be compared using FASTA, a program in GCG, using default or recommended parameters. FASTA (e.g., FASTA2 and FASTA3) provides alignments and percent sequence identity of the regions of the best overlap between the query and search sequences (Pearson, 1990, Methods Enzymol. 183:63-98; Pearson, 2000, Methods Mol. Biol. 132:185-219). Another preferred algorithm when comparing a sequence of the invention to a database containing a large number of sequences from different organisms is the computer program BLAST, especially blastp or tblastn, using default parameters. See, e.g., Altschul et al., 1990, J. Mol. Biol. 215:403-410; Altschul et al., 1997, Nucleic Acids Res. 25:3389-402; herein incorporated by reference.

Conventional notation is used herein to portray polypeptide sequences: the left-hand end of a polypeptide sequence is the amino-terminus; the right-hand end of a polypeptide sequence is the carboxyl-terminus.

An intact "antibody" comprises at least two heavy (H) chains and two light (L) chains inter-connected by disulfide bonds. See generally, Fundamental Immunology, Ch. 7 (Paul, W., 1989, ed., 2nd ed. Raven Press, N.Y.) (incorporated by reference in its entirety for all purposes). Each heavy chain is comprised of a heavy chain variable region (HCVR or $V_H$) and a heavy chain constant region ($C_H$). The heavy chain constant region is comprised of three domains, CH1, CH2 and CH3. Each light chain is comprised of a light chain variable region (LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The assignment of amino acids to each domain is in accordance with the definitions of Kabat, 1987 and 1991, In: Sequences of Proteins of Immunological Interest (National Institutes of Health, Bethesda, Md.), or Chothia & Lesk, 1987, J. Mol. Biol. 196: 901-917; Chothia et al., 1989, Nature 342:878-883. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)).

"Ligand binding site" as the term is used herein, refers to a portion of a polypeptide or protein, or fragment thereof, which specifically binds with another molecule, also referred to as a binding partner or cognate ligand. Preferably, the ligand binding site ("LBS") can, but need not, comprise at least one glycan site (also referred to herein as a "potential glycosylation site") which can be, but need not be, occupied by a carbohydrate moiety. An example of a ligand binding site is the ligand binding site of RAGE which comprises a glycan site at asparagine amino acid residue number 2 (Asn2 or N2), and further comprises a second glycan site at N58, and where the LBS specifically binds with a RAGE ligand, including, but not limited to, amyloid beta (Aβ), serum amyloid A (SAA), S100, carboxymethyl lysine (CML), amphoterin and CD11b/CD18.

The term "antigen binding site" or "antigen binding portion" as used interchangeably herein, refer to one or more fragments of an antibody that retain the ability to specifically bind to an antigen (e.g., IgE). It has been shown that the antigen-binding function of an antibody can be performed by fragments of a full-length antibody. Examples of binding fragments encompassed within the term "antigen binding site" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., 1989, Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)); see, e.g., Bird et al., 1988, Science 242:423-426; and Huston et al., 1988, Proc. Natl. Acad. Sci. USA 85:5879-5883. Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., 1993, Proc. Natl. Acad. Sci. USA 90:6444-6448; Poljak et al., 1994, Structure 2:1121-1123).

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al., 1995, Human Antibodies and Hybridomas 6:93-101) and use of a cysteine residue, a marker peptide and a C-terminal polyhistidine tag to make bivalent and biotinylated scFv molecules (Kipriyanov et al., 1994, Mol. Immunol. 31:1047-1058). Other examples include where one or more CDRs from an antibody are incorporated into a molecule either covalently or noncovalently to make it an immunoadhesin that specifically binds to an antigen of interest, such as IgE. In such embodiments, the CDR(s) may be incorporated as part of a larger polypeptide chain, may be covalently linked to another polypeptide chain, or may be incorporated noncovalently. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Where an "antibody" is referred to herein with respect to the present invention, it should be understood that an antigen-binding portion thereof may also be used. An antigen-binding portion competes with the intact antibody for specific binding. See generally, Paul. W., ed., 1989, In: Fundamental Immunology, Ch. 7 (2nd ed., Raven Press, N.Y.) (incorporated by reference in its entirety for all purposes). Antigen-binding portions may be produced by recombinant DNA techniques or by enzymatic or chemical cleavage of intact antibodies. In some embodiments, "antigen-binding portions" include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide. In embodiments having one or more binding sites, the binding sites may be identical to one another or may be different.

The terms "monoclonal antibody" or "monoclonal antibody composition" as used herein refer to a preparation of antibody molecules of single molecular composition. A monoclonal antibody composition displays a single binding specificity and affinity for a particular epitope The terms "human antibody", or "fully human antibody", as used herein, are intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure or antigen binding portions thereof may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "human monoclonal antibody" or "fully human monoclonal antibody" refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene, where the B cell is fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" or "class" refers to the antibody class (e.g., IgM or IgG) that is encoded by the heavy chain constant region genes. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, "subclass" refers to the further specification within an isotype of the heavy chain constant region gene, such as, for example, the IgG1, IgG2, IgG3, or IgG4 subclasses within the IgG isotype.

The phrases "an antibody recognizing an antigen" and "an antibody specific for an antigen" are used interchangeably herein with the term "an antibody which binds specifically to an antigen." The term "antibody dependent cellular cytotoxicity" or "ADCC" refers to a cell-mediated reaction in which non-specific cytotoxic cells (e.g. NK cells, neutrophils, macrophages, etc.) recognize antibody bound on a target cell and subsequently cause lysis of the target cell. Such cytotoxic cells that mediate ADCC generally express Fc receptors (FcR). The primary cells for mediating ADCC (NK cells) express FcγRIII, whereas monocytes express FcγRI, FcγRII, FcγRIII, and/or FcγRIV. FcR expression on hematopoietic cells is summarized in Ravetch and Kinet, *Annu. Rev. Immunol.* 9:457-92 (1991). To assess ADCC activity of a molecule, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., *Proc. Natl. Acad. Sci.* (USA) 95:652-656 (1998).

The terms "Fc receptor" or "FcR" are used to describe a receptor that binds to the Fc region of an antibody where the Fc region comprises a hinge region and the $C_H2$ and $C_H3$ domains of the heavy chain. For example, the FcR can be a native sequence human FcR. The FcR can be one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, Daeron, 1997, Annu. Rev. Immunol. 15:203-234). FcRs are reviewed in Ravetch and Kinet, 1991, Annu. Rev. Immunol. 9:457-92; Capel et al., 1994, Immunomethods 4:25-34; and de Haas et al., 1995, J. Lab. Clin. Med. 126:330-341. Other FcRs, including those to be identified in the future, are encompassed by the term "FcR" herein. The term also includes the neonatal receptor, FcRn, which is responsible for the transfer of maternal IgGs to the fetus (Guyer et al., 1976, Immunol. 117:587) and Kim et al., 1994, J. Immunol. 24:249). The primary FcR binding site on immunoglobulin Fc fragments resides in the hinge region between the $C_H1$ and $C_H2$. This hinge region interacts with the FcR1-3 on various leukocytes and trigger these cells to attack the target. (Wines et al., 2000, J. Immunol. 164:5313-5318). The hinge region encompasses, but is not limited to, the sequences described in U.S. Pat. No. 6,165,476.

The term "capable of inducing antibody dependent cellular cytotoxicity" refers to the ability of an agent, such as an antibody, to demonstrate ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody. Such modifications are described, for example, in U.S. Patent Publication No. 2007/0092521.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide inhibitor which recognizes and binds a cognate ligand (e.g., an anti-IgE antibody that binds with its cognate antigen, IgE) in a sample, but does not substantially recognize or bind other molecules in the sample. Thus, under designated assay conditions, the specified binding moiety (e.g., an antibody or an antigen-binding portion thereof) binds preferentially to a particular target molecule, e.g., IgE, and does not bind in a significant amount to other components present in a test sample. A variety of assay formats may be used to select an antibody that specifically binds a molecule of interest. For example, solid-phase ELISA immunoassay, immunoprecipitation, BIAcore, FACS, and Western blot analysis are among many assays that may be used to identify an antibody that specifically reacts with IgE. Typically, a specific or selective reaction will be at least twice background signal or noise and more typically more than 10 times background, even more specifically, an antibody is said to "specifically bind" an antigen when the equilibrium dissociation constant ($K_D$) is ≤1 µM, preferably ≤100 nM and most preferably ≤10 nM.

The term "$k_{on}$", as used herein, is intended to refer to the on-rate, or association rate of a particular antibody-antigen or receptor-ligand interaction, whereas the term "$k_{off}$," as used herein, is intended to refer to the off-rate, or dissociation rate of a particular antibody-antigen/receptor-ligand interaction. The term "$K_D$", as used herein, is intended to refer to the dissociation constant, which is obtained from the ratio of $k_{off}$ to $k_{on}$ (i.e., $k_{off}/k_{on}$) and is expressed as a molar concentration (M). $K_D$ values for antibodies or other binding partners can be determined using methods well established in the art. One method for determining the $K_D$ is by using surface plasmon resonance, typically using a biosensor system such as a Biacore® system.

The term "chimeric antibody" as used herein means an antibody that comprises regions from two or more different antibodies. In certain embodiments a "chimeric antibody" comprises variable region sequences derived from one species and constant region sequences derived from another species, such as an antibody in which the variable region sequences are derived from a mouse antibody and the constant region sequences are derived from a human antibody. In one embodiment, one or more of the CDRs are derived from a mouse anti-human IgE antibody. In another embodiment, all of the CDRs are derived from a mouse anti-human IgE antibody. In another embodiment, the CDRs from more than one mouse anti-human IgE antibodies are combined in a chimeric human antibody. For instance, a chimeric antibody may comprise a CDR1 from the light chain of a first mouse anti-IgE antibody, a CDR2 from the light chain of a second mouse anti-human IgE antibody and a CDR3 and CDR3 from the light chain of a third mouse anti-human IgE antibody, and the CDRs from the heavy chain may be derived from one or more other anti-IgE antibodies. Further, the framework regions may be derived from one of the same mouse anti-human IgE antibodies or from one or more different mice.

Moreover, as discussed previously herein, chimeric antibody includes an antibody comprising a portion derived from the germline sequences of more than one species.

The carbohydrate moieties of the present invention will be described with reference to commonly used nomenclature for the description of oligosaccharides. A review of carbohydrate chemistry which uses this nomenclature is found in Hubbard and Ivatt (1981) Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic acid (IUB-IUPAC Joint Commission on Biochemical Nomenclature, 1982, J. Biol. Chem. 257: 3347-3351; (1982) J. Biol. Chem. 257: 3352).

The carbohydrate structures of the present invention occur on the protein expressed as N-linked oligosaccharides. "N-linked glycosylation" refers to the attachment of the carbohydrate moiety via GlcNAc to an asparagine residue in a polypeptide chain. The N-linked carbohydrates all contain a common Man 1-6(Man1-3)Manβ1-4GlcNAcβ1-4GlcNAcβ-R core structure. Therefore, in the core structure described, R represents an asparagine residue of the produced glycoprotein. The sequence of the protein produced will contain an asparagine-X-serine, asparagine-X-threonine, and asparagine-X-cysteine, wherein X is any amino acid except proline (Asn-Xaa-Ser/Thr). "O-linked" carbohydrates, by contrast are characterized by a common core structure, which is the GalNAc attached to the hydroxyl group of a threonine or serine but no consensus sequence is required. Of the N-linked carbohydrates the most important are the "complex" N-linked carbohydrates such as the "bi-antennary" structures described herein.

The skilled artisan will recognize that the glycoprotein immunoglobulin G (IgG) is associated with three types of complex biantennary structures containing zero, one or two galactose residues (Wormland et al., 1997, Biochemistry 36:1370-1380) commonly known as G0, G1 and G2, respectively. With respect to human antibody molecules of the IgG class each has an N-linked oligosaccharide attached at the amide side chain of Asn 297 of the β-4 bend of the inner face of the CH2 domain of the Fc region (Beale and Feinstein, 1976, Q. Rev. Biophys. 9:253-259; Jefferis et al., 1995, Immunol. Letts. 44:111-117). The oligosaccharide moiety attached at Asn 297 of the IgG CH2 domain is of the complex biantennary type having the identified hexasaccharide core structure and variable outer sugar residues (see Jefferis et al., 1997, supra; Wyss and Wagner, 1996, Current Opinions in Biotech. 7:409-416). The core structure (GlcNAc2Man3GlcNAc) is typical of biantennary oligosaccharides and can be represented schematically as:

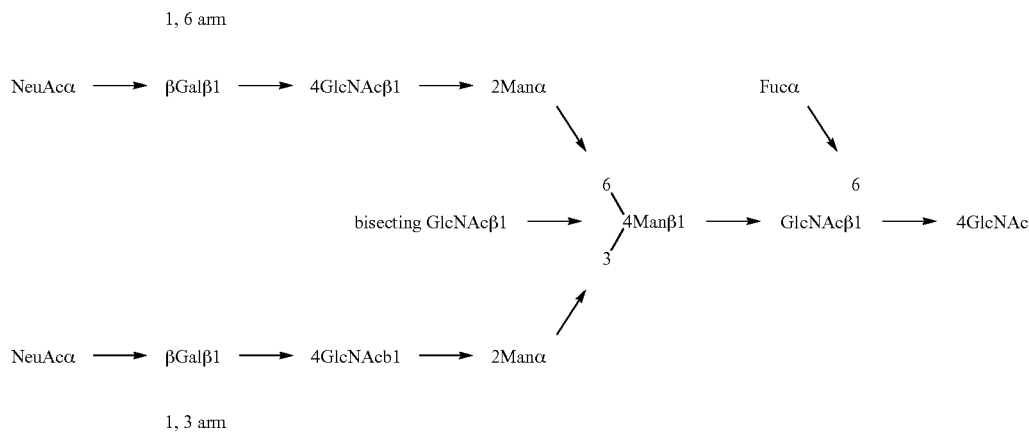

Since each core structure may have a bisecting N-acetyl-glucoseamine, core fucose and either galactose or sialic acid outer saccharides, there are a total of 36 structurally unique oligosaccharides which may occupy the Asn 297 site (Jefferis and Lund, supra). It will also be recognized that within a particular CH2 domain, glycosylation at Asn 297 may be asymmetric owing to different oligosaccharide chains attached at either Asn 297 residue within the two chain Fc domain. For example, while the heavy chain synthesized within a single antibody-secreting cell may be homogeneous in its amino acid sequence, it is generally differentially glycosylated resulting in a large number of structurally unique Ig glycoforms.

The major types of complex oligosaccharide structures found in the CH2 domain of the IgG are depicted in International Patent Publication No. WO 99/22764 at page 7.

According to the present invention G0 refers to a biantennary structure wherein no terminal sialic acids (NeuAcs) or Gals are present, G1 refers to a biantennary structure having one Gal and no NeuAcs and G2 refers to a biantennary structure with two terminal Gals and no NeuAcs. See, e.g., FIG. 12 depicting exemplary structures of G0, G1, G-1 and G2.

"Glycoform" refers to a complex oligosaccharide structure comprising linkages of various carbohydrate units. Such structures are described in, e.g., *Essentials of Glycobiology* Varki et al., eds., Cold Spring Harbor Laboratory Press, Cold Spring Harbor, N.Y. (1999), which also provides a review of standard glycobiology nomenclature. Such glycoforms include, but are not limited to, G2, G1, G0, G−1, and G−2 (see, e.g., International Patent Publication Nos. WO98/58964 and WO 99/22764).

The term "glycan site occupancy" or "glycan occupancy" encompasses where a potential N-link or O-link glycosylation site in a protein can comprise a covalently linked carbohydrate moiety (i.e., the glycan site is occupied) or not (i.e., the glycan site is unoccupied). Where there are at least two potential glycosylation sites on a polypeptide, either none (0-glycan site occupancy), one (1-glycan site occupancy) or both (2-glycan site occupancy) can be occupied by a carbohydrate moiety.

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

It is likely that proteins, including antibodies, expressed by different cell lines or in transgenic animals will have different glycan site occupancies, glycoforms and/or glycosylation patterns compared with each other. However, all glycoproteins, including antibodies, encoded by the nucleic acid molecules provided herein, or comprising the amino acid sequences provided herein are part of the instant invention, regardless of the glycosylation, glycan occupancy or glycoform pattern of the glycoproteins.

"Glycosylation inhibitor" or "glycosylation-inhibiting compound," as the terms are used herein refers to a substance or compound where a polypeptide or protein produced in the presence of the substance or compound comprises either at least one unglycosylated site or comprises at least one carbohydrate moiety less at the same site than an otherwise identical polypeptide or protein which is produced by an otherwise identical cell under otherwise identical conditions but in the absence of the substance or compound. Glycosylation inhibitors include, but are not limited to, tunicamycin, tunicaymycin homologs, streptovirudin, mycospocidin, amphomycin, tsushimycin, antibiotic 24010, antibiotic MM 19290, bacitracin, corynetoxin, showdomycin, duimycin, 1-deoxymannonojirimycin, deoxynojirimycin, N-methyl-1-dexoymannojirimycin, brefeldin A, glucose and mannose analogs, 2-deoxy-D-glucose, 2-deoxyglucose, D-(+)-mannose, D-(+) galactose, 2-deoxy-2-fluoro-D-glucose, 1,4-dideoxy-1,4-imino-D-mannitol (DIM), fluoroglucose, fluoromannose, UDP-2-deoxyglucose, GDP-2-deoxyglucose, hydroxymethylglutaryl-CoA reductase inhibitors, 25-hydroxycholesterol, hydroxycholesterol, swainsonine, cycloheximide, puromycin, actinomycin D, monensin, m-Chlorocarbonyl-cyanide phenylhydrazone (CCCP), compactin, dolichyl-phosphoryl-2-deoxyglucose, N-Acetyl-D-Glucosamine, hygoxanthine, thymidine, cholesterol, glucosamine, mannosamine, castanospermine, glutamine, bromoconduritol, conduritol epoxide and conduritol derivatives, glycosylmethyl-p-nitrophenyltriazenes, β-Hydroxynorvaline, threo-β-fluoroasparagine, D-(+)-Gluconic acid δ-lactone, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl] trimethyl ammonium iodide, iodoacetate, and/or fluoroacetate One of ordinary skill in the art will readily recognize or will be able to determine glycosylation-inhibiting substances that may be used in accordance with methods and compositions of the present invention without undue experimentation.

By the term "glycosylation inhibiting amount" as the term is used herein is meant the amount of a substance or compound where a polypeptide or protein produced in the presence of the substance compound comprises a detectable decrease in glycosylation compared with an otherwise identical polypeptide or protein produced in the absence of the substance or compound. That is, either the polypeptide or protein comprises at least one more unglycosylated site (unoccupied glycan site) or comprises at least one carbohydrate moiety less at the same potential glycosylation site than an otherwise identical polypeptide or protein which is produced by a cell under otherwise identical conditions but in the absence of the substance or compound.

"Decreased glycosylation," "less glycosylation", or "inhibited glycosylation" as used interchangeably herein, encompass where a polypeptide or protein comprises at least one more unglycosylated (i.e., aglycosylated) site, that is, a completely unoccupied glycan site with no carbohydrate moiety attached thereto, or comprises at least one carbohydrate moiety less at the same potential glycosylation site than an otherwise identical polypeptide or protein which is produced by a cell under otherwise identical conditions but in the absence of a glycosylation inhibiting substance or compound.

By the term "effective amount", as used herein, is meant an amount that when administered to a cell, mediates a detectable decrease in the glycosylation of a polypeptide or protein of interest produced by the cell compared with the glycosylation of an otherwise identical polypeptide or protein produced by an otherwise identical cell under otherwise identical conditions in the absence of the substance or compound. The glycosylation of a polypeptide or protein can be assessed by numerous methods well-known in the art including, e.g., such methods as disclosed herein.

The skilled artisan would understand that the effective amount of the compound or composition administered herein varies and can be readily determined based on a number of factors such as the cell type, the number of potential glycosylation sites in the polypeptide or protein, the cell culture conditions used, and the like.

By the term "compete", as used herein with regard to an antibody or a ligand:receptor binding pair, is meant that a first antibody, or an antigen-binding portion thereof, or receptor protein competes for binding with a second antibody, or an antigen-binding portion thereof, or cognate ligand of the receptor protein, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). For instance, cross-competing antibodies can bind to the epitope, or potion of the epitope, to which the antibodies of the invention bind. Both competing and cross-competing antibodies are encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

"Instructional material," as that term is used herein, includes a publication, a recording, a diagram, or any other medium of expression which can be used to communicate the usefulness of the method, compound, combination, and/or composition of the invention in the kit for affecting, alleviating or treating the various diseases or disorders recited herein or for using the novel methods disclosed herein. Optionally, or alternately, the instructional material can describe one or more methods of producing a therapeutic protein and/or alleviating the diseases or disorders in a cell, a tissue, or a mammal, including as disclosed elsewhere herein using the protein of the invention.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

Except when noted, the terms "patient" or "subject" are used interchangeably and refer to mammals such as human patients and non-human primates, as well as veterinary subjects such as rabbits, rats, and mice, and other animals. Preferably, patient refers to a human.

Conventional notation is used herein to portray polypeptide sequences: the left-hand end of a polypeptide sequence is the amino-terminus; the right-hand end of a polypeptide sequence is the carboxyl-terminus.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide receptor which recognizes and binds a cognate ligand or binding partner (e.g., an anti-IgE antibody that binds with its cognate antigen, IgE, or a receptor for advanced glycation end-products [RAGE] and one of its ligands, such as, amyloid beta peptide or S100) in a sample, but does not substantially recognize or bind other molecules in the sample. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample. A variety of assay formats may be used to select an antibody or peptide that specifically binds a molecule of interest. For example, solid-phase ELISA immunoassay, immunoprecipitation, BIAcore™ (GE Healthcare, Piscataway, N.J.), FACS, Octet™ (FortéBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant $(K_D)$ is ≤1 µM, preferably ≤100 nM and most preferably ≤10 nM.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, to "treat" means reducing the frequency with which symptoms of a disease (i.e., tumor growth and/or metastasis, or other effect mediated by the numbers and/or activity of immune cells, and the like) are experienced by a patient. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Combination therapy" embraces the administration of a first therapeutic agent and another therapeutic agent as part of a specific treatment regimen optionally including a maintenance phase, intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention.

"Combination therapy" embraces administration of these therapeutic agents in a sequential manner, that is, wherein each therapeutic agent is administered at a different time, as well as administration of these therapeutic agents, or at least two of the therapeutic agents, in a substantially simultaneous manner. Sequential or substantially simultaneous administration of each therapeutic agent can be effected by any appropriate route including, but not limited to, oral routes, intravenous routes, intramuscular, subcutaneous routes, and direct absorption through mucous membrane tissues. The therapeutic agents can be administered by the same route or by different routes. For example, a first therapeutic agent (e.g., a chemotherapeutic agent) can be administered orally, and a second agent (e.g., an antibody or other glycoprotein) can be administered intravenously. Further, a first therapeutic agent of the combination selected may be administered by intravenous injection while the other therapeutic agents of the combination may be administered orally. Alternatively, for example, both the therapeutic agents may be administered by intravenous or subcutaneous injection.

In the present specification the term "sequential" means, unless otherwise specified, characterized by a regular sequence or order, e.g., if a dosage regimen includes the administration of a therapeutic protein (e.g., an antibody, a glycoprotein, and the like) and a chemotherapeutic agent, a sequential dosage regimen could include administration of the therapeutic protein before, simultaneously, substantially simultaneously, or after administration of the chemotherapeutic agent, but both agents will be administered in a regular sequence or order. The term "separate" means, unless otherwise specified, to keep apart one from the other. The term "simultaneously" means, unless otherwise specified, happening or done at the same time, i.e., the compounds of the invention are administered at the same time. The term "substantially simultaneously" means that the compounds are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the therapeutic protein and the chemotherapeutic agent.

"Combination therapy" also can embrace the administration of the therapeutic agents as described above in further combination with other biologically active ingredients (such as, but not limited to, a second and different therapeutic protein, a vaccine, and the like) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

"Batch culture" as the term is used herein refers to a method of culturing cells in which all the components that will ultimately be used in culturing the cells, including the medium, as well as the cells themselves, are provided at the beginning of the culturing process. A batch culture is typically stopped at some point and the cells and/or components in the medium are harvested and optionally purified.

"Bioreactor" encompasses any vessel useful for the growth of a cell culture. A bioreactor can be of any size so long as it is useful for the culturing of cells. Typically, the bioreactor will be at least 1 liter and may be 10, 100, 250, 500, 1,000, 2,500, 5,000, 8,000, 10,000, 12,000 liters or more, or any volume in between. The internal conditions of the bioreactor, including, but not limited to pH and temperature, are optionally controlled during the culturing period. A bioreactor can be composed of any material that is suitable for holding cell cultures suspended in media under the culture conditions of the present invention, including glass, plastic or metal. The term "production bioreactor" as used herein refers to the final bioreactor used in the production of the polypeptide or protein of interest. The volume of the production bioreactor is typically at least 500 liters and may be 1,000, 2,500, 5,000, 8,000, 10,000, 12,000 liters or more, or any volume in between. One of ordinary skill in the art will be aware of and will be able to choose suitable bioreactors for use in practicing the present invention.

By the term "cell density" as used herein is meant that number of cells present in a given volume of medium.

"Cell viability", as used herein refers to the ability of cells in culture to survive under a given set of culture conditions or experimental variations. The term as used herein also refers to that portion of cells which are alive at a particular time in relation to the total number of cells, living and dead, in the culture at that time.

The terms "medium", "cell culture medium", and "culture medium" as these terms are used herein, refer to a solution containing nutrients that nourish growing cells. In certain embodiments, the culture medium is useful for growing mammalian cells. Typically, a culture medium provides essential and non-essential amino acids, vitamins, energy sources, lipids, and trace elements required by the cell for minimal growth and/or survival. A culture medium may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, a medium is advantageously formulated to a pH and salt concentration optimal for cell survival and proliferation. In certain embodiments, the medium is a feed medium that is added after the beginning of the cell culture. In certain embodiments, the cell culture medium is a mixture of a starting nutrient solution and any feed medium that is added after the beginning of the cell culture.

The term "complex medium", as the term is used herein, refers to a medium that contains at least one component whose identity or quantity is either unknown or uncontrolled.

The terms "culture" and "cell culture" as used herein refer to a cell population that is suspended in a medium (defined elsewhere herein) under conditions suitable to survival and/or growth of the cell population. As will be clear to those of ordinary skill in the art, these terms as used herein also refer to the combination comprising the cell population and the medium in which the population is suspended. In certain embodiments, the cell culture is a mammalian cell culture.

"Defined medium" as that term is used herein refers to a medium in which the composition of the medium is both known and controlled.

By the term "fed-batch culture" as used herein is meant to encompass a method of culturing cells in which additional components are provided to the culture at a time or times subsequent to the beginning of the culture process. The provided components typically comprise nutritional supplements for the cells which have been depleted during the culturing process. Additionally or alternatively, the additional components may include supplementary components (defined elsewhere herein). In certain embodiments, the additional components may be provided in a feed medium. A fed-batch culture is typically stopped at some point and the cells and/or components in the medium are harvested and optionally purified.

By the term "modified fed-batch" or mixed-mode culture process" as used herein is meant to encompass a method of culturing cells which uses a combination of perfusion and/or batch and/or fed-batch processes during the inoculum stage and/or final bioreactor production stages. An exemplary modified fed-batch process is discussed, but is not limited to, a process in U.S. Patent Application Publication No. US 2009/0042253 (published Feb. 12, 2009), which is incorporated by reference as if set forth in its entirety herein.

"Feed medium" as used herein refers to a solution containing nutrients which nourish growing mammalian cells that is added after the beginning of the cell culture. A feed medium may contain components identical to those provided in the initial cell culture medium. Alternatively, a feed medium may contain one or more additional components beyond those provided in the initial cell culture medium. Additionally or alternatively, a feed medium may lack one or more components that were provided in the initial cell culture medium. In certain embodiments, one or more components of a feed medium are provided at concentrations or levels identical or similar to the concentrations or levels at which those components were provided in the initial cell culture medium. In certain embodiments, one or more components of a feed medium are provided at concentrations or levels different than the concentrations or levels at which those components were provided in the initial cell culture medium. In certain embodiments, a feed medium contains supplementary components.

By the term "supplementary components" as the term is used herein, is encompassed components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, supplementary components are added to the initial cell culture. In certain embodiments, supplementary components are added after the beginning of the cell culture.

By the term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. Alternatively or additionally, the term as used herein also refers to any portion of a given polypeptide that includes at least an established sequence element found in the full-length polypeptide. In some embodiments, the sequence element spans at least about 4-5, 10, 15, 20, 25, 30, 35, 40, 45, 50 or more amino acids of the full-length polypeptide.

The term "gene" as used herein refers to any nucleotide sequence, DNA or RNA, at least some portion of which encodes a discrete final product, typically, but not limited to, a polypeptide. Optionally, the term refers not only to the coding sequence that encodes the polypeptide or other discrete final product, but may also encompass regions preceding and/or following the coding sequence that modulate the basal level of expression (see definition of "Genetic control element" below), as well as intervening sequences ("introns") between individual coding segments ("exons").

By the term "genetic control element" as used herein refers to any sequence element that modulates the expression of a product of a gene to which it is operably linked. Genetic control elements may function by either increasing or decreasing the expression levels of a gene product and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

The term "host cell" as used herein refers to a cell that is grown in culture according to the present invention to produce a protein or polypeptide of interest. In certain embodiments, the host cell is a mammalian cell.

By the term "hybridoma" as the term is used herein, is meant to encompass a cell or progeny of a cell resulting from fusion of an immortalized cell and an antibody-producing cell. The resulting hybridoma is an immortalized cell that produces antibodies. The individual cells used to create the hybridoma can be from any mammalian source, including, but not limited to, rat, pig, rabbit, sheep, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., 1983, Nature 537:3053).

The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. For example, a polypeptide may be glycosylated. A polypeptide to be expressed according to the present invention can be a therapeutic polypeptide. A therapeutic polypeptide is a polypeptide that has a biological effect on a region in the body on which it acts or on a region of the body on which it remotely acts via intermediates. Examples of therapeutic polypeptides are discussed in more detail below.

"Protein," as the term is used herein, refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of multiple polypeptides that physically associate with one another, the term "protein" as used herein refers to the multiple polypeptides that are physically coupled and function together as the discrete unit. A protein to be expressed according to the present invention can be a protein therapeutic. A protein therapeutic is a protein that has a biological effect on a region in the body on which it acts or on a region of the body on which it remotely acts via intermediates. Examples of protein therapeutics are discussed in more detail below.

"Recombinantly expressed polypeptide" and "recombinant polypeptide" as used herein refer to a polypeptide expressed from a host cell that has been manipulated to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

By the term "titer" as the term is used herein is meant the total amount of recombinantly expressed polypeptide or protein produced by a cell culture in a given amount of medium volume. Titer is typically expressed in units of milligrams or micrograms of polypeptide or protein per milliliter of medium.

Process for Control of Glycosylation

The present invention provides improved methods and media formulations for the production of glycosylated proteins and/or glycosylated polypeptides by cell culture wherein the proteins or polypeptides comprise decreased glycosylation. In certain embodiments, the invention provides methods that reduce glycosylation of proteins in a cell culture.

Previous work has demonstrated that lactate, a metabolic waste product, is detrimental to cell growth, viability, and/or protein production or quality. Previous work has also demonstrated that lactate levels in cell culture may be kept low by maintaining low glucose levels throughout the duration of the culture to reduce glycolysis (Cruz et al., 1999, Biotechnology and Bioengineering 66:104-113). However, because continuous monitoring and adjustment of glucose levels is not practical for large-scale production of proteins or polypeptides, previous work has demonstrated that addition of a glycolysis-inhibiting substance to cell culture medium can reduce glycolysis to improve protein production (International Patent Application No. PCT/US2007/083473, published as WO 2008/055260 May 8, 2008). More specifically, it has been shown that addition of 2-deoxy-D-glucose, a glycolysis inhibitor, decreased the level of lactate in cell culture medium and, in certain concentrations, it also increased production of a protein of interest by the cells.

The present invention provides improved methods and media formulations for the production of glycoproteins and/or polypeptides comprising decreased glycosylation by cell culture that obviate the need to continuously monitor and adjust glucose levels of the culture. The present invention provides improved methods and media formulations for the production of glycoproteins or polypeptides comprising decreased glycosylation wherein the glycoprotein or polypeptide comprises a potential glycosylation site in a ligand binding site or antigen binding site. In certain embodiments, the glycoprotein or polypeptide comprising decreased glycosylation demonstrates improved biological characteristics, including, but not limited to, improved binding (e.g., increased specificity and/or avidity) with a cognate ligand or binding partner. In certain embodiments, the cell culture is a batch or fed-batch culture.

Certain compositions of the present invention include a cell culture medium comprising a glycosylation-inhibiting substance. In certain embodiments, such glycosylation-inhibiting substance comprises tunicamycin, tunicaymycin homologs, streptovirudin, mycospocidin, amphomycin, tsushimycin, antibiotic 24010, antibiotic MM 19290, bacitracin, corynetoxin, showdomycin, duimycin, 1-deoxymannonojirimycin, deoxynojirimycin, N-methyl-1-dexoymannojirimycin, brefeldin A, glucose and mannose analogs, 2-deoxy-D-glucose, 2-deoxyglucose, D-(+)-mannose, D-(+) galactose, 2-deoxy-2-fluoro-D-glucose, 1,4-dideoxy-1,4-imino-D-mannitol (DIM), fluoroglucose, fluoromannose, UDP-2-deoxyglucose, GDP-2-deoxyglucose, hydroxymethylglutaryl-CoA reductase inhibitors, 25-hydroxycholesterol, hydroxycholesterol, swainsonine, cycloheximide, puromycin, actinomycin D, monensin, m-Chlorocarbonyl-cyanide phenylhydrazone (CCCP), compactin, dolichyl-phosphoryl-2-deoxyglucose, N-Acetyl-D-Glucosamine, hygoxanthine, thymidine, cholesterol, glucosamine, mannosamine, castanospermine, glutamine, bromoconduritol, conduritol epoxide and conduritol derivatives, glycosylmethyl-p-nitrophenyltriazenes, β-Hydroxynorvaline, threo-β-fluoroasparagine, D-(+)-Gluconic acid δ-lactone, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl]trimethyl ammonium iodide, iodoacetate, and/or fluoroacetate. The skilled artisan, armed with the teachings provided herein, would appreciate that numerous useful potential glycosylation inhibitors, which inhibit either N-linked, O-linked, or both, glycosylation are known in the art and may be assayed for their use in the novel methods of the invention. See, e.g., Elbein, 1985, Methods in Enzymol. 98:135-154; Elbein, 1987, Ann. Rev. Biochem. 56:497-534.

According to some embodiments, levels of glycosylation (e.g., number of glycan sites that are occupied on a protein or peptide, the size and/or complexity of glycoform at the site, and the like) of a recombinant protein produced by cell culture are lower than levels of glycosylation of the protein produced under otherwise identical conditions in an otherwise identical medium that lacks such a glycolysis-inhibiting substance. According to some embodiments, glycosylation levels of the culture are lower than glycosylation levels produced under otherwise identical conditions in an otherwise identical medium that lacks such a glycosylation-inhibiting substance.

Other embodiments of the invention are discussed in detail below. Those of ordinary skill in the art will understand, however, that various modifications to these embodiments are within the scope of the appended claims. It is the claims and equivalents thereof that define the scope of the present invention, which is not and should not be limited to or by this description of certain embodiments.

Cells

Any host cell susceptible to cell culture, and to expression of protein or polypeptides, may be utilized in accordance with the present invention. In certain embodiments, the host cell is mammalian. Mammalian cell lines available as hosts for expression are well known in the art and include many immortalized cell lines available from the American Type Culture Collection (ATCC), including but not limited to Chinese hamster ovary (CHO) cells, HEK, human cervical carcinoma cells (HeLa, ATCC CCL 2), baby hamster kidney (BHK) cells, monkey kidney cells (COS), and human hepatocellular carcinoma cells (e.g., Hep G2). Other non-limiting examples of mammalian cells that may be used in accordance with the present invention include human retinoblasts (PER.C6 (CruCell, Leiden, The Netherlands)); monkey kidney CV1 line transformed by SV40 (COS-7, ATCC CRL 1651); human embryonic kidney line 293 or 293 cells subcloned for growth in suspension culture (Graham et al., 1977, J. Gen Virol. 36:59); baby hamster kidney cells (BHK, ATCC CCL 10); mouse sertoli cells (TM4, Mather, 1980, Biol. Reprod. 23:243-251); monkey kidney cells (CV1 ATCC CCL 70); African green monkey kidney cells (VERO-76, ATCC CRL-1 587); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., 1982, Annals N.Y. Acad. Sci. 383:44-68); MRC 5 cells; FS4 cells; a human hepatoma line (Hep G2); and numerous myeloma cell lines, including, but not limited to, BALB/c mouse myeloma line (NS0/1, ECACC No: 85110503), NS0 cells and Sp2/0 cells.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

The invention includes any eukaryotic expression system known in the art or disclosed herein for production of proteins of interest, such as expression in an insect cell system, a yeast expression system, or a mammalian cell system, such as, but not limited to, CHO cells. That is, any cell culture system wherein the protein produced is otherwise glycosylated and where decreased glycosylation (N-linked and/or O-linked) is desired, can be used in the novel methods of in the invention.

In some embodiments, a yeast expression system is used and control of glycosylation using a glycosylation inhibitor decreases or eliminates N-linked, O-linked, or both types of glycosylation. This is particularly useful because yeast systems may mediate unwanted N-linked, and more especially, O-linked glycosylation. Thus, the novel methods disclosed herein provide useful methods for producing proteins in yeast with decreased level of N- and/or O-linked glycosylation. The less glycosylated or aglycosylated proteins produced thereby may exhibit useful characteristics such as, but not limited to, less heterogeneity, more standardized profiles for improved batch/lot results, improved binding characteristics, and the like.

Other cell lines that may be used are insect cell lines, such as Sf9 cells. Plant host cells include, e.g., *Nicotiana*, *Arabidopsis*, duckweed, corn, wheat, potato, etc. Bacterial host cells include *E. coli* and *Streptomyces* species. Yeast host cells include *Schizosaccharomyces pombe*, *Saccharomyces cerevisiae* and *Pichia pastoris*.

Nucleic acid molecules encoding the protein of interest expression vectors comprising these nucleic acid molecules may be used for transfection of a suitable mammalian, plant, bacterial or yeast host cell. Transformation may be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

An expression vector may also be delivered to an expression system using DNA biolistics, wherein the plasmid is precipitated onto microscopic particles, preferably gold, and the particles are propelled into a target cell or expression system. DNA biolistics techniques are well-known the art and devices, e.g., a "gene gun", are commercially available for delivery of the microparticles in to a cell (e.g., Helios Gene Gun, Bio-Rad Labs., Hercules, Calif.) and into the skin (PMED Device, PowderMed. Ltd., Oxford, UK).

Expression of proteins from production cell lines may be enhanced using a number of known techniques. For example, the glutamine synthetase gene expression system (the GS system) and the plasma-encoded neomycin resistance system are common approaches for enhancing expression under certain conditions.

As noted above, in many instances the cells will be selected or engineered to produce high levels of a protein or polypeptide of interest. Often, cells are manipulated to produce high levels of protein, for example by introduction of a gene encoding the protein or polypeptide of interest and/or by introduction of control elements that regulate expression of the gene (whether endogenous or introduced) encoding the polypeptide or protein of interest.

Certain polypeptides may have detrimental effects on cell growth, cell viability or some other characteristic of the cells that ultimately limits production of the polypeptide or protein of interest in some way. Even amongst a population of cells of one particular type engineered to express a specific polypeptide, variability within the cellular population may exist such that certain individual cells will grow better and/or produce more polypeptide of interest. In certain embodiments, the cell line is empirically selected by the practitioner for robust growth under the particular conditions chosen for culturing the cells. In certain embodiments, individual cells engineered to express a particular polypeptide are chosen for large-scale production based on cell growth, final cell density, percent cell viability, titer of the expressed polypeptide or any combination of these or any other conditions deemed important by the practitioner.

Culturing the Cells

The present invention may be used with any cell culture method or system that is amenable to the expression of polypeptides. For example, the cells may be grown in batch or fed-batch cultures, where the culture is terminated after sufficient expression of the polypeptide, after which the expressed polypeptide is harvested and optionally purified. Alternatively, the cells may be grown in perfusion cultures, where the culture is not terminated and new nutrients and other components are periodically or continuously added to the culture, during which the expressed polypeptide is periodically or continuously harvested. In other embodiments, the cells are grown in a modified fed-batch process such as that described in U.S. Patent Application Publication No. US 2009/0042253.

The cells may be grown in any convenient volume chosen by the practitioner. For example, the cells may be grown in small scale reaction vessels ranging in volume from a few milliliters to several liters. Alternatively, the cells may be grown in large scale commercial Bioreactors ranging in volume from approximately least 1 liter to 10, 100, 250, 500, 1,000, 2,500, 5,000, 8,000, 10,000, 12,000 liters or more, or any volume in between.

The temperature of the cell culture will be selected based primarily on the range of temperatures at which the cell culture remains viable, at which a high level of polypeptide is produced, the temperature at which production or accumulation of metabolic waste products is minimized, and/or any combination of these or other factors deemed important by the practitioner. As one non-limiting example, CHO cells grow well and produce high levels or protein or polypeptide at approximately 37° C. In general, most mammalian cells grow well and/or can produce high levels or protein or polypeptide within a range of about 25° C. to 42° C., although methods taught by the present disclosure are not limited to these temperatures. Certain mammalian cells grow well and/or can produce high levels or protein or polypeptide within the range of about 35° C. to 40° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times during the cell culture process. Those of ordinary skill in the art will be able to select appropriate temperature or temperatures in which to grow cells, depending on the needs of the cells and the production requirements of the practitioner.

Furthermore, the culture may be subjected to one or more temperature shifts during the course of the culture. When shifting the temperature of the culture, the temperature shift may be relatively gradual. For example, it may take several hours or days to complete the temperature change. Alternatively, the temperature shift may be relatively abrupt. The temperature may be steadily increased or decreased during the culture process. Alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple discrete temperature shifts are encompassed in these embodiments. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

As with the initial temperature or temperature range, the temperature or temperature range of the cell culture after the temperature shift(s) will be selected based primarily on the temperature(s) at which the cell culture remains viable, the range in which a high level of polypeptide or protein is produced, the range in which production or accumulation of metabolic waste products is minimized, and/or any combination of these or other factors deemed important by the practitioner. In general, most mammalian cells remain viable and produce high levels or protein or polypeptide within a range of about 25° C. to 42° C., although methods taught by the present disclosure are not limited to these temperatures. In certain embodiments, mammalian cells remain viable and produce high levels or protein or polypeptide within a range of about 25° C. to 35° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times after the temperature shift(s). Those of ordinary skill in the art will be able to select appropriate temperature(s) or temperature range(s) in which to grow cells after the temperature shift(s), depending on the particular needs of the cells and the particular production requirements of the practitioner. The cells may be grown for any amount of time, depending on the needs of the practitioner and the requirement of the cells themselves. One of ordinary skill in the art will be able to select the exact time point at which the culture is shifted to the lower temperature based on the character of the cell line used, the character of the protein or polypeptide to be produced, the presence or absence of other components in the medium or any other factor that is desirable to his or her experimental and/or other needs.

In certain embodiments, the cell culture is grown at a temperature ranging from about 32° C. to about 42° C. and the temperature is shifted to about 25° C. to about 31° C., more preferably, the cell culture is grown at a temperature ranging from about 33° C. to about 37° C. and the temperature is shifted to about 28° C. to about 31° C., yet more preferably, the cell culture is grown at a temperature ranging from about 34° C. to 37° C. and the temperature is shifted to about 29° C. to about 31° C., more preferably, the cell culture is grown at a temperature of about 34° C. and the temperature is shifted to about 31° C.

In certain embodiments, batch and fed-batch reactions are terminated once the expressed polypeptide reaches a sufficiently high titer, as determined by the needs of the practitioner. As non-limiting examples, cell cultures may be terminated when the polypeptide titer is 100, 200, 300, 400, 500, 600, 700, 800, 900, 1000, 1100, 1200, 1300, 1400, 1500, 2000 mg/L or higher. One of ordinary skill in the art will be able to select one or more appropriate titers at which a batch and/or fed-batch culture may be harvested. Additionally or alternatively, batch and fed-batch reactions are terminated once the cells reach a sufficiently high density, as determined by the needs of the practitioner. For example, the culture may be terminated once the cells reach 1, 5, 10, 15, 20, 25, 30, 35, 40, 45, 50, 55, 60, 65, 70, 75, 80, 85, 90, 95 or 99 percent of maximal viable cell density.

In certain embodiments, batch and/or fed-batch cell cultures are terminated to prevent the undesirable production or accumulation of metabolic waste products such as lactate and ammonium. In certain embodiments, a cell culture is terminated before lactate accumulates in the culture to an undesirable level. As non-limiting examples, a cell culture may be terminated before lactate reaches 8, 7, 6, 5, 4, 3, 2, or 1 g/L.

In certain embodiments, batch and fed-batch reactions are terminated once the cell density reaches a sufficiently high level, as determined by the needs of the practitioner. For example, a cell culture may be terminated once the cell density reaches 1, 2, 3, 4, 5, 6, 7, 8, 9, 10, 11, or 12 million cells per mL, or more. In certain embodiments, batch and fed-batch reactions are terminated before the cell density reaches 1 million cells per mL.

In certain cases, it may be beneficial or necessary to supplement the cell culture during the subsequent production phase with nutrients or other medium components that have been depleted or metabolized by the cells. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. These supplementary components may all be added to the cell culture at one time, or they may be provided to the cell culture in a series of additions.

One of ordinary skill in the art will be able to tailor specific cell culture conditions in order to optimize certain characteristics of the cell culture including but not limited to extent of glycosylation of a protein of interest, cell growth rate, cell viability, final cell density of the cell culture, final concentration of detrimental metabolic byproducts such as lactate and ammonium, final titer of the expressed polypeptide or any combination of these or other conditions deemed important by the practitioner.

Media Compositions

Any of a wide variety of growth media may be used in accordance with the present invention. In certain embodiments, the cells are grown in any of a variety of chemically defined media, wherein the components of the media are both known and controlled. In certain embodiments, the cells are grown in any of a variety of complex media, in which not all components of the medium are known and/or controlled.

Chemically defined growth media for cell culture have been extensively developed and published over the last several decades, including chemically defined growth media for mammalian cell culture. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive cell cultures that produce recombinant proteins and/or polypeptides.

Defined media typically consist of roughly fifty chemical entities at known concentrations in water. Most defined media also contain one or more well-characterized proteins such as insulin, IGF-1, transferrin or BSA, but others require no protein components and so are referred to as protein-free defined media. The chemical components of defined media generally fall into five broad categories: amino acids, vitamins, inorganic salts, trace elements, and a miscellaneous category that defies neat categorization.

All media, defined or complex, include an energy source for the growing cells. Often, the energy source is glucose, a simple monosaccharide sugar that has the chemical formula $C_6H_{12}O_6$. Traditional media formulations, including commercially available media such as Ham's F10 (Sigma), Minimal Essential Medium ([MEM], Sigma), RPMI-1640 (Sigma), and Dulbecco's Modified Eagle's Medium ([DMEM], Sigma), have contained relatively high levels of glucose. Glucose has traditionally been thought to be required in abundance since it is the primary metabolic energy sources for the cells. However, rapid consumption of glucose leads to increased glycosylation. Because as demonstrated herein, decreased glycosylation may provide improved biological functions and characteristics for glycoproteins, decreasing and/or controlling the level of glucose in cell culture may be desired. Accordingly, the present invention encompasses decreasing and/or controlling the amount of glucose in cell culture medium. In one embodiment, glucose concentration is maintained in a range from about 100 µg/L to about 10 g/L, more preferably, from about 500 µg/L to about 10 g/L, yet more preferably, from about 500 µg/L to about 5 g/L, even more preferably, from about 500 µg/L to about 3 g/L, even more preferably, from about 1 g/L to about 3 g/L, more preferably, from about 1 g/L to about 2 g/L, and yet more preferably, about 0.05 g/L to 0.5 g/L. Most preferably, the glucose concentration is maintained at about 1.5 g/L.

The present invention encompasses the discovery that certain cell culture methods and medium formulations minimize and even completely inhibit glycosylation of glycoproteins. Tunicamycin is an antibiotic that is a glycosylation inhibitor that inhibits the glycosyltransferase that transfers phospho-N-acetylglucosamine (P-GlcNAc) from uridine diphosphate (UDP)-GlcNAc to form dolichol phosphate (Dol-P)-GlcNAc. 2-deoxy-D-glucose is a structural analog of glucose in which the hydroxyl group at the 2' position of the sugar is replaced with a hydrogen moiety. Thus, without wishing to be bound by any particular theory, it appears that the mechanism of glycosylation inhibition is not crucial in that reduced glycosylation of a protein using either inhibitor resulted in a glycoprotein having a lower glycosylation level. More surprisingly, decreasing glycosylation of a protein comprising a glycosylation site located within a ligand binding site mediated improved binding by the protein of a cognate ligand regardless of the glycosylation inhibitor used to inhibit glycosylation in cell culture.

This disclosure demonstrates that media formulations that contain glycosylation-inhibiting substances, including but not limited to, 2-deoxy-D-glucose and tunicamycin, result in a decrease in the glycosylation of glycoproteins when used to grow cells in cell culture. Moreover, the disclosure provided herein surprisingly demonstrates that where the glycosylation site is located within a ligand binding site of the glycoprotein, or an antigen binding site of an antibody, reducing the glycosylation at that site mediated improved biological function (e.g., improved ligand or antigen binding) by the glycoprotein compared with the identical glycoprotein comprising a greater level of glycosylation and produced under otherwise identical cell culture conditions in the absence of a glycosylation inhibiting substance. Without wishing to be bound by any particular theory, it is possible that by providing such a glycosylation-inhibiting substance in the cell culture media, glycosylation is reduced thereby affecting the ability of the binding site to bind its cognate ligand, thus increasing the binding affinity or specificity of the protein.

Further, the disclosure provided herein surprisingly demonstrates that where the glycosylation site is located within an antigen binding site of an antibody, the novel processes disclosed herein can reduce the level of glycosylation of the antibody at both the glycosylation site located within the antigen binding site and the glycosylation site located in the constant region of the heavy chain of the antibody. Further, reducing the glycosylation at that site mediated may improve biological function (e.g., improved antigen binding) by the antibody compared with the identical antibody comprising a greater level of glycosylation and produced under otherwise identical cell culture conditions in the absence of a glycosylation inhibiting substance.

Thus, the present invention provides novel methods for affecting the glycosylation level and/or the binding characteristics of a glycoprotein, including an antibody, without altering the amino acid sequence of the glycoprotein.

In certain embodiments, a glycosylation-inhibiting substance to be used in accordance with the present invention comprises 2-deoxy-D-glucose. In certain embodiments, 2-deoxy-D-glucose is provided at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 25, 30, 35, 40, 45, 50 or more grams per liter. In certain embodiments, the ratio of 2-deoxy-D-glucose to glucose in the cell culture is 1/50, 1/45, 1/40, 1/39, 1/38, 1/37, 1/36, 1/35, 1/34, 1/33, 1/32, 1/31, 1/30, 1/29, 1/28, 1/27, 1/26, 1/25, 1/24, 1/23, 1/22, 1/21, 1/20, 1/19, 1/18, 1/17, 1/16, 1/15, 1/14, 1/13, 1/12, 1/11, 1/10, 1/9, 1/8, 1/7, 1/6, 1/5, 1/4, 1/3, 1/2, 1/1 or any ratio higher or lower than these. One of ordinary skill in the art will understand that the foregoing concentrations and ratios of 2-deoxy-D-glucose in a cell culture medium may be achieved using a batch culture, a fed-batch culture, a perfusion culture, and/or a modified fed-batch culture.

The present invention also encompasses medium formulations in which the concentration of glucose is limited. In certain embodiments, the concentration of glucose is maintained in a range from about 100 μg/L to about 10 g/L, more preferably, more preferably, from about 100 μg/L to about 5 g/L, even more preferably, from about 100 μg/L to about 3 g/L, yet more preferably, from about 100 ug/L to about 1.5 g/L, more preferably, from about 100 ug/L to 1 g/L and most preferably, about 50 ug/L to 0.5 g/L.

The present disclosure teaches that several factors may be important in decreasing the glycosylation of a protein of interest and, thereby, providing improved biological characteristics to the protein, including improved binding to a cognate ligand. Such factors include, but are not limited to, addition of a glycosylation-inhibitor to the cell culture, the level of glucose in the culture, the temperature of the culture, including, but not limited to, subjecting the cell culture to a temperature shift, and the medium used to culture the cells.

Particular cell lines may produce different levels of glycosylation and/or the glycoform(s) present at the glycosylation site. Regardless, utilization of the inventive methods and media compositions described herein will result in a lower overall glycosylation of glycoproteins in any given cell culture compared with the level of glycosylation of the protein produced under otherwise identical conditions in the absence of a glycosylation inhibitor.

Inventive media formulations disclosed herein may optionally be supplemented as necessary or desirable with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, protein hydrolysates, or glucose or other energy source. In certain embodiments of the present invention, it may be beneficial to supplement the media with chemical inductants such as hexamethylene-bis(acetamide) ("HMBA") and/or sodium butyrate ("NaB"). These optional supplements may be added at the beginning of the culture or may be added at a later point in order to replenish depleted nutrients or for another reason. One of ordinary skill in the art will be aware of any desirable or necessary supplements that may be included in media formulations of the present invention and will be able to select which particular supplements to add based on his or her experimental and/or other needs.

Polypeptides

Any polypeptide comprising a potential glycosylation site that is expressible in a host cell may be produced in accordance with the methods and compositions disclosed herein. Even more preferably, the polypeptide comprises a potential glycosylation site in the ligand binding site of the polypeptide, such as, but not limited to, the antigen binding site of an antibody, the ligand binding site of a receptor, and the like.

The polypeptide may be expressed from a gene that is endogenous to the host cell, or from a heterologous gene that is introduced into the host cell. The polypeptide may be one that occurs in nature, or may alternatively have a sequence that has been engineered or selected. A polypeptide to be produced may be assembled from polypeptide fragments that individually occur in nature. Additionally or alternatively, the engineered polypeptide may include one or more fragments that are not naturally occurring.

Exemplary glycoproteins that can be produced according to the novel methods provided herein are well-known in the art, and include, but are not limited to, the extensive list provided in Int. Pat. Pub. No. PCT/US2004/011494 filed Apr. 9, 2004, published as WO 2004/099231 on Nov. 18, 2004 (see, e.g., FIG. 28A through 28CC).

Practitioners of the present invention will selected their polypeptide of interest, and will know its precise amino acid sequence. Any given protein that is to be expressed in accordance with the present invention will have its own particular characteristics and may influence the glycosylation level by the cultured cells, and may be expressed at lower levels than another polypeptide or protein grown under identical culture conditions. One of ordinary skill in the art will be able to appropriately modify inventive media and methods described herein in order to control the level of glycosylation of any given expressed polypeptide or protein.

In certain embodiments, the polypeptide comprises a potential glycosylation site. That is, the skilled artisan would understand that the polypeptide comprises characteristics, including certain amino acid sequences, indicating that the protein may be glycosylated by a cell. In some embodiments, the potential glycosylation site is an O-linked glycosylation site comprising either serine or threonine. See Peter-Katalinic, 2005, Methods in Enzymol. 405:139-171 In further embodiments, the polypeptide comprises at least one N-linked glycosylation site. See Medzihradszky, 2005, Methods in Enzymol. 405:116-138. One skilled in the art would appreciate that certain amino acid sequences are recognized by the cell as a glycosylation signal such that a glycan is attached at certain asparagine residues. In some embodiments, the N-linked glycosylation site comprises the amino acid sequence asparagine-X-serine (N-X-S) or asparagine-X-threonine, where X can be any amino acid except for proline. In some embodiments, the N-linked glycosylation site comprises an amino acid sequence including, but not limited to, asparagine-isoleucine-threonine (NIT), asparagine-glycine-serine (NGS), asparagine-serine-threonine (NST), and asparagine-threonine-serine (NTS). Methods for identification of potential and actual protein glycosylation sites are known in the art and include, but are not limited to, post-translational modification prediction software that is freely available at the Expert Protein Analysis System proteomics server of the Swiss Institute of Bioinformatics at URL http://www.expasy.ch/tools/. These various programs include, but are not limited to, DictyOGlyc (prediction of GlcNAc O-glycosylation sites in Dictyostelium; freely available at http://www.cbs.dtu.dk/services/DictyOGlyc/); NetCGlyc (prediction of C-mannosylation sites in mammalian proteins; freely available at http://www.cbs.dtu.dk/services/NetCGlyc/); NetOGlyc (prediction of O-GalNAc, mucin-type glycosylation sites in mammalian proteins; freely available at http://www.cbs.dtu.dk/services/NetOGlyc/); NetGlycate (prediction of glycation of epsilon amino groups of lysines in human proteins; freely available at http://www.cbs.dtu.dk/services/NetNGlyc/); OGPET (prediction of O-GalNAc, mucin-type glycosylation sites in eukaryotic (non-protozoan) proteins; freely available at http://ogpet.utep.edu/OGPET/); and YinOYang (prediction of O-beta-GlcNAc attachment sites in eukaryotic protein sequences; freely available at http://www.cbs.dtu.dk/services/YinOYang/). In certain embodiments, a protein may comprise both O- and N-linked glycosylation sites and such proteins are well-known in the art or may be readily identified by the skilled artisan.

Polypeptides that may desirably be expressed in accordance with the present invention will often be selected on the basis of an interesting or useful biological or chemical activity. In certain embodiments, methods and/or compositions of the present invention are employed to express a protein therapeutic or polypeptide therapeutic. For example, the present invention may be employed to express any pharmaceutically or commercially relevant receptor, antibody, enzyme, hormone, regulatory factor, antigen, binding agent etc. The following list of polypeptides and proteins that can be produced according to the present invention is merely exemplary in nature, and is not intended to be a limiting recitation. One of ordinary skill in the art will understand that any polypeptide or protein may be expressed in accordance with the present invention and will be able to select the particular polypeptide to be produced based on his or her particular needs.

Receptors

A class of polypeptides that have been shown to be effective as pharmaceutical and/or commercial agents and that can desirably be produced according to the teachings of the present invention includes receptors. Given the biological importance of receptors and their importance as potential therapeutic agents, production of these molecules in accordance with methods and compositions of the present invention is of particular interest. Receptors are typically transmembrane glycoproteins that function by recognizing an extra-cellular signaling ligand. Receptors often have a protein kinase domain in addition to the ligand recognizing domain. This protein kinase domain initiates a signaling pathway by phosphorylating target intracellular molecules upon binding the ligand, leading to developmental or metabolic changes within the cell.

In certain embodiments, a receptor for advanced glycation endproducts (RAGE), is expressed in accordance with systems and methods of the present invention. Exemplary RAGE proteins that may be expressed are provided in, among others, International Patent Application Nos. PCT/US2005/027694 filed on Aug. 3, 2005, now published as WO 2006/017643 on Feb. 16, 2006; PCT/US2005/027705 filed on Aug. 3, 2005, now published as WO 2006/017647 on Feb. 16, 2006; PCT/US2007/001686 filed on Jan. 23, 2007, now published as WO 2007/094926 on Aug. 23, 2007; PCT/US2007/010125 filed on Apr. 25, 2007, now published as WO 2007/130302 on Nov. 15, 2007; and PCT/US2008/001786 filed on Feb. 11, 2008, now published as WO 2008/100670 on Aug. 21, 2008 (each of which is incorporated herein by reference in its entirety). In one embodiment, the RAGE ligand binding site comprises from about amino acid 24 (Gln24; Q24) to amino acid residue number 52 (Lys52; K52) with respect to the amino acid sequence of full-length human RAGE (SEQ ID NO:3), including the signal sequence. In other embodiments, the ligand binding site comprises the RAGE V-domain, from about amino acid 24 (Gln24; Q24) to amino acid residue number 116 (Arg116; R116) with respect to the amino acid sequence of full-length human RAGE (SEQ ID NO:3), including the signal sequence. The full-length amino acid sequence of human RAGE is set forth below with the signal sequence in lowercase letters and the two potential N-linked glycosylation sites underlined:

```
Full-length HUMAN RAGE              (SEQ ID NO: 3)
maagtavgaw vlvlslwgav vgAQNITARI GEPLVLKCKG

APKKPPQRLE WKLNTGRTEA WKVLSPQGGG PWDSVARVLP

NGSLFLPAVG IQDEGIFRCQ AMNRNGKETK SNYRVRVYQI

PGKPEIVDSA SELTAGVPNK VGTCVSEGSY PAGTLSWHLD

GKPLVPNEKG VSVKEQTRRH PETGLFTLQS ELMVTPARGG

DPRPTFSCSF SPGLPRHRAL RTAPIQPRVW EPVPLEEVQL

VVEPEGGAVA PGGTVTLTCE VPAQPSPQIH WMKDGVPLPL

PPSPVLILPE IGPQDQGTYS CVATHSSHGP QESRAVSISI

IEPGEEGPTA GSVGGSGLGT LALALGILGG LGTAALLIGV

ILWQRRQRRG EERKAPENQE EEEERAELNQ SEEPEAGESS

TGGP
```

A nucleic acid sequence encoding amino acids 1-251 of human RAGE (SEQ ID NO:4) is as follows:

```
ATGGCAGCCG GAACAGCAGT TGGAGCCTGG GTGCTGGTCC TCAGTCTGTG GGGGGCAGTA GTAGGTGCTC

AAAACATCAC AGCCCGGATT GGCGAGCCAC TGGTGCTGAA GTGTAAGGGG GCCCCCAAGA AACCACCCCA

GCGGCTGGAA TGGAAACTGA ACACAGGCCG GACAGAAGCT TGGAAGGTCC TGTCTCCCCA GGGAGGAGGC

CCCTGGGACA GTGTGGCTCG TGTCCTTCCC AACGGCTCCC TCTTCCTTCC GGCTGTCGGG ATCCAGGATG

AGGGGATTTT CCGGTGCCAG GCAATGAACA GGAATGGAAA GGAGACCAAG TCCAACTACC GAGTCCGTGT

CTACCAGATT CCTGGGAAGC CAGAAATTGT AGATTCTGCC TCTGAACTCA CGGCTGGTGT TCCCAATAAG

GTGGGGACAT GTGTGTCAGA GGGGAGCTAC CCTGCAGGGA CTCTTAGCTG GCACTTGGAT GGGAAGCCCC

TGGTGCCTAA TGAGAAGGGA GTATCTGTGA AGGAACAGAC CAGGAGACAC CCTGAGACAG GGCTCTTCAC

ACTGCAGTCG GAGCTAATGG TGACCCCAGC CCGGGGAGGA GATCCCCGTC CCACCTTCTC CTGTAGCTTC

AGCCCAGGCC TTCCCCGACA CCGGGCCTTG CGCACAGCCC CCATCCAGCC CCGTGTCTGG GAGCCTGTGC

CTCTGGAGGA GGTCCAATTG GTGGTGGAGC CAGAAGGTGG AGCAGTAGCT CCT
```

Typically, the first 22 or 23 amino acids (shown in lower-case letters) comprise the signal sequence and are not present in the mature RAGE expressed in mammalian cells. Further, where the first 23 amino acids comprise the signal sequence and the mature RAGE comprises a glutamine amino acid residue (Q) at position 1, the glutamine (Q) typically cyclizes to pyroglutamic acid (indicated as "pE"), such that the ligand binding site of human RAGE comprises the following sequences:

```
                                             (SEQ ID NO: 13)
AQNITARI GEPLVLKCKG APKKPPQRLE WK (SEQ ID NO: 14)
QNITARI GEPLVLKCKG APKKPPQRLE WK (SEQ ID NO: 15)
pENITARI GEPLVLKCKG APKKPPQRLE WK
```

In some embodiments, the RAGE polypeptide comprises the V-like domain of RAGE comprising the following amino acid sequences:

```
                                                                   (SEQ ID NO: 16)
AQNITARI GEPLVLKCKG APKKPPQRLE WKLNTGRTEA WKVLSPQGGG PWDSVARVLP NGSLFLPAVG

IQDEGIFRCQ AMNRNGKETK SNYRVR (SEQ ID NO: 17)
QNITARI GEPLVLKCKG APKKPPQRLE WKLNTGRTEA WKVLSPQGGG PWDSVARVLP NGSLFLPAVG

IQDEGIFRCQ AMNRNGKETK SNYRVR (SEQ ID NO: 18)
pENITARI GEPLVLKCKG APKKPPQRLE WKLNTGRTEA WKVLSPQGGG PWDSVARVLP NGSLFLPAVG

IQDEGIFRCQ AMNRNGKETK SNYRVR
```

One skilled in the art would understand, armed with the disclosure provided herein, that the ligand binding site of human RAGE can comprise any length of amino acids ranging from the sequence of SEQ ID NO:14 to the amino acid sequence of SEQ ID NO:16. In each instance, the ligand binding site of RAGE comprises at least one N-linked glycosylation site located at Asn3 and at 59 of the sequence of SEQ ID Nos:13 and 16 (where the signal sequence is 22 amino acids in length) or at Asn2 and/or Asn58 of SEQ ID NOS: 14, 15, 17 and 18 (where the signal sequence is 23 amino acids in length).

According to some embodiments, a receptor for advanced glycation endproducts comprises a soluble RAGE (sRAGE). That is, sRAGE does not comprise the transmembrane and cytoplasmic domains of RAGE. See Neeper et al., 1992, J. Biol. Chem. 267:14998-15004; Park et al., 1998, Nature Med. 4:1025-1031. In certain embodiments, a RAGE comprises a soluble RAGE-Ig fusion protein, e.g., RAGE-Fc, which comprises a portion of RAGE comprising the ligand binding site covalently linked with a portion of an immunoglobulin ("Ig"). In certain embodiments, the sRAGE fusion protein comprises the Fc of the immunoglobulin (where the Fc typically comprises the hinge region, $C_H2$ domain and $C_H3$ domain of, for example, an IgG). In certain embodiments, the sRAGE-Ig comprises the hinge portion of human Ig, wherein the hinge domain spans the amino acid sequence from the end of the first heavy chain constant domain ($C_H1$) through the beginning of the second heavy chain constant domain ($C_H2$). See, e.g., U.S. Pat. No. 6,165,476, to Strom & Zhen (setting out the amino acid sequences for the hinge domains of human and mouse immunoglobulins at the table bridging from the end of column 4 to the top of column 5). In certain embodiments, the human sRAGE-Ig fusion protein comprising the hinge region encompasses the human sRAGE-Fc described in International Patent Application No. PCT/US2003/025996 filed Aug. 18, 2003, now published as WO 2004/016229 on Feb. 26, 2004, as shown in FIG. 3A. In further embodiments, the sRAGE-Ig fusion protein comprises the human RAGE extracellular domain (amino acid residue numbers 1 through 344 of SEQ ID NO:3) fused with a human IgG constant domain (amino acids Pro100 through Lys330 of human $IgG_1$) via a six amino acid linker (i.e., IEGRMD). See Catalog No. 1145-RG, R&D Systems, Minneapolis, Minn. Further, the sRAGE-Fc fusion comprising a hinge region encompasses the murine sRAGE-Fc as described in WO 2004/016229 at FIG. 1B, as well as mouse and rat sRAGE-Fc fusion proteins as described in Catalog Nos. 1179-RG, 1616-RG, respectively, commercially available from R&D Systems (Minneapolis, Minn.). In other embodiments, the RAGE fusion protein comprises the soluble domain of mouse RAGE fused with a human Ig domain In additional embodiments, the RAGE fusion protein comprises a sRAGE portion of human RAGE fused with a constant heavy chain domain from a human IgG4 immunoglobulin. See, e.g., International Patent Publication No. PCT/US2008/066956 filed (setting forth the amino acid sequence of a human sRAGE-Fc fusion protein comprising the Fc region of human IgG4 as shown at Table 2, paragraph 055, at page 12; a sRAGE-Fc IgG4 fusion protein comprising a seven amino acid linker sequence, GSGSGSG, linking the sRAGE portion with the human IgG4 Fc portion as shown at Table 4, paragraph 0059, page 13, a sRAGE-Fc fusion protein comprising the amino acid sequence of a human sRAGE linked to the Fc region of human IgG4 as shown at Table 6, paragraph 0063, at page 15, further comprising two point mutations at or near the putative furin cleavage site of human RAGE; and a sRAGE-Fc IgG4 fusion protein comprising a seven amino acid linker sequence, GSGSGSG, linking the sRAGE portion with the human IgG4 Fc portion further comprising two point mutations at or near the putative furin cleavage site of human RAGE as shown at Table 8, paragraph 0067, page 17).

In some embodiments, the sRAGE-Ig comprises an immunoglobulin portion lacking the hinge portion wherein the first amino acids of the $C_H2$ are not present and where the hinge region is replaced with a RAGE intradomain linker sequence, or a sequence that is at least 70, 75, 80, 85, 90, 95, 97, 98, or 99 percent identical thereto.

Figure 4:
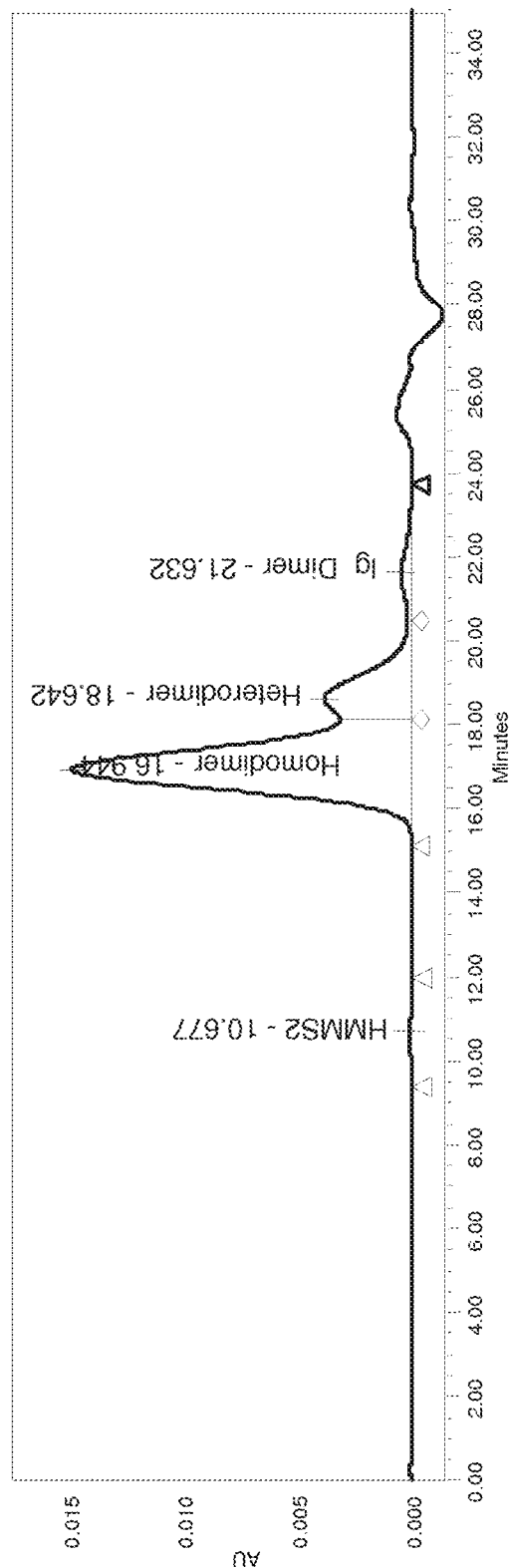
FIG. 4 shows results of an analysis of sRAGE-Ig fusion protein by size exclusion chromatography (SEC). Purified sRAGE-Ig fusion protein was diluted to 3 mg/mL in mobile phase (350 mM citrate, pH 6.0) and analyzed by Size Exclusion Chromatography (SEC) utilizing a Superdex™ 200

In certain embodiments, the RAGE-Ig fusion protein comprises an extracellular portion of RAGE fused with a portion of an Ig lacking a hinge region. In one embodiment, the extracellular portion of human RAGE, comprising a V-domain of RAGE, is fused with a portion of human IgG1 comprising a portion of the $C_H2$ domain and the entire $C_H3$ domain of human IgG1 and lacking a hinge region. See, e.g., WO 2006/017643 and WO 2006/017647 (incorporated by reference herein in its entirety and providing a sRAGE-Ig fusion protein comprising three domains, e.g., as shown in FIG. 4). In another embodiment, the RAGE-Ig fusion protein comprises four domains, the RAGE V-domain, the RAGE C1 domain, a portion of the human IgG1 $C_H2$ domain and the entire $C_H3$ domain of human IgG1, and a hinge region. See, e.g., WO 2006/017643 and WO 2006/017647 at FIG. 5; and WO 2008/100470 (providing a three domain sRAGE-Fc fusion protein at FIGS. 4B and 4D and providing a four domain sRAGE-Ig fusion protein as shown in FIGS. 4A and 4C) (each of which is incorporated by reference as if set forth in its entirety herein) all lacking a hinge region. Further, in certain embodiments, the sRAGE fusion protein comprises a fusion protein comprising the extracellular, i.e., soluble, domain of canine RAGE fused with a six-histidine tag at the carboxyl terminus (Catalog No. 4750-RG, R&D Systems, Minneapolis, Minn.).

Certain RAGE fusion proteins are exemplified herein. However, the present invention is in no way limited to these or any other RAGE polypeptides, but encompasses any RAGE protein, or fragment thereof, comprising a ligand binding site, or a sequence that is at least 70, 75, 80, 85, 90, 95, 97, 98, or 99 percent identical thereto, where, preferably, the ligand binding site comprises a potential glycosylation site.

In certain embodiments, the RAGE-fusion protein comprises the ligand binding site of RAGE starting at either alanine23 (22 amino acid signal sequence not in mature peptide) or glutamine (Q) or pyroglutamic acid (pE) at residue 24 (23 amino acid signal sequence not in mature peptide and glutamine cyclized to pE) and ending at amino acid residue Lys30 or Lys29 of SEQ ID NO:3, respectively. In other embodiments, the RAGE portion of the fusion protein comprises the V-domain of RAGE from about amino acid alanine23 (22 amino acid signal sequence not in mature peptide) or glutamine (Q) or pyroglutamic at residue 24 (23 amino acid signal sequence not in mature peptide and glutamine cyclized to pE) and ending at amino acid residue Arg116 of SEQ ID NO:3 (including the leader peptide). See WO 2007/094926, e.g., at FIG. 1D.

In other embodiments, where the RAGE-Ig fusion protein comprises a C-terminal lysine (K) amino acid residue, one skilled in the art would understand that the lysine residue may be clipped resulting in a fusion protein lacking the C-terminal lysine residue.

In another aspect, the present invention provides a composition comprising an amount of a protein as described in any one of the embodiments herein, wherein at least 0.5% of the protein is aglycosylated. The percentage of the amount of protein relates to, inter alia, the number of protein molecules in a sample, and takes into account, where appropriate, the effect of glycosylation on the molecular weight of the protein. In another embodiment, the percentage of protein in the fully glycosylated form is less than 67%, or less than 65%, or less than 60%, or less than 55%, or less than 50%, or less than 45% of the total amount of the protein. In another embodiment, the percentage of the amount protein in the fully glycosylated form is less than the percentage of the amount of the protein in all of the non-fully glycosylated forms combined. For example, in the case of a protein having 2 potential sites of glycosylation, the percentage of the amount of the sRAGE-Ig fusion protein in the fully glycosylated form (i.e., double glycosylation) is less than the percent of the amount of the protein present in the mono and aglycosylated forms combined. In a further embodiment, the present invention provides a composition comprising an amount of an sRAGE-Ig fusion protein as described in any one of the embodiments herein, wherein at least 0.5% of the sRAGE-Ig fusion protein is aglycosylated. In a further embodiment of any of the embodiments of this paragraph, a site may be considered aglycosylated wherein the number of carbohydrate residues attached to a site is 3 or less, or 2 or less, or 1 or less.

When used within the context of a composition comprising an amount of a sRAGE-Ig fusion protein, the "amount of a sRAGE-Ig fusion protein" is an amount that is detectable by typical analytical detection methods for proteins. In an embodiment, the amount of the sRAGE-Ig fusion protein is greater than 0.01 mg. In another embodiment, the amount of the sRAGE-Ig fusion protein is greater than 0.1 mg. In another embodiment, the amount of the sRAGE-Ig fusion protein is greater than 1.0 mg.

In another embodiment, the percentage of the amount of the sRAGE-Ig fusion protein in the aglycosylated form is at least 1%, or at least 2%, or at least 3%, or at least 4%, or at least 5%, or at least 6%, or at least 7%, at least 8%, or at least 9%, or at least 10%, or at least 12%, or at least 14%, or at least 16%, or at least 18%, or at least 20%, or at least 22%, or at least 24%, or at least 26%, or at least 28%, or at least 30% of the total amount of the sRAGE-Ig fusion protein. In a further embodiment of any of the embodiments of this paragraph, a site may be considered aglycosylated wherein the number of carbohydrate residues attached to a site is 3 or less, or 2 or less, or 1 or less.

In another embodiment, the percentage of sRAGE-Ig fusion protein in the fully glycosylated form is less than 67%, or less than 65%, or less than 60%, or less than 55%, or less than 50%, or less than 45% of the total amount of the sRAGE-Ig fusion protein. In another embodiment, the percentage of the amount of the sRAGE-Ig fusion protein in the fully glycosylated form is less than the percentage of the amount of the sRAGE-Ig fusion protein in all of the non-fully glycosylated forms combined. For example, in the case of a sRAGE-Ig fusion protein having three potential sites of glycosylation, the percentage of the amount of the sRAGE-Ig fusion protein in the fully glycosylated form (i.e., triple glycosylation) is less than the percent of the amount of the sRAGE-Ig fusion protein present in the double, mono, and aglycosylated forms combined. Thus, where the number of potential glycosylation sites is n and n is an integer greater than or equal to 1, the amount of sRAGE-Ig fusion protein comprising n glycosylated sites is less than the total amount of the sRAGE-Ig fusion protein present in all of the forms having less than or equal to n–1 glycosylated sites. In a further embodiment of any of the embodiments of this paragraph, a site may be considered aglycosylated wherein the number of carbohydrate residues attached to a site is 3 or less, or 2 or less, or 1 or less.

In another aspect, the present invention provides a composition comprising an amount of a fusion protein, wherein the fusion protein comprises a RAGE polypeptide linked to an immunoglobulin polypeptide,
a) wherein the RAGE polypeptide comprises a fragment of human RAGE (SEQ ID NO:3) wherein the fragment of human RAGE comprises a ligand binding site and at least one amino acid residue that may be glycosylated,
b) wherein the immunoglobulin polypeptide comprises a $C_H2$ domain or a portion of a $C_H2$ domain of an immunoglobulin and a $C_H3$ domain of an immunoglobulin, and
c) wherein the N-terminal residue of the immunoglobulin polypeptide is linked to the C-terminal residue of the RAGE polypeptide; and
wherein at least 0.5% of the amount of the fusion protein is aglycosylated. In an embodiment, the fusion protein does not include a signal sequence of the RAGE polypeptide. The signal sequence may be amino acid residues 1-18, 1-22, or 1-23 of SEQ ID NO:4. In another embodiment, the RAGE polypeptide comprises a sequence selected from the group consisting of SEQ ID NO:13, SEQ ID NO:14, and SEQ ID NO:15. In another embodiment, the RAGE polypeptide comprises a sequence selected from the group consisting of SEQ ID NO:16, SEQ ID NO:17, and SEQ ID NO:18. In another embodiment, the N-terminal sequence of the fusion protein is selected from the group consisting of SEQ ID NO:13, SEQ ID NO:14, and SEQ ID NO:15. In another embodiment, the RAGE polypeptide comprises amino acid residues 23-116, 23-118, 23-136, 23-230, 23-256, 23-305, 23-321, 23-330, or 23-344 of SEQ ID NO:3.

When used within the context of a composition comprising an amount of a fusion protein comprising a RAGE polypeptide linked to an immunoglobulin polypeptide, the "amount of a fusion protein" is an amount that is detectable by typical analytical detection methods for proteins. In an embodiment, the amount of the fusion protein is greater than 0.01 mg. In another embodiment, the amount of the fusion protein is greater than 0.1 mg. In another embodiment, the amount of the fusion protein is greater than 1.0 mg.

In another embodiment, the percentage of the amount of the fusion protein in the aglycosylated form is at least 1%, or at least 2%, or at least 3%, or at least 4%, or at least 5%, or at least 6%, or at least 7%, at least 8%, or at least 9%, or at least 10%, or at least 12%, or at least 14%, or at least 16%, or at least 18%, or at least 20%, or at least 22%, or at least 24%, or at least 26%, or at least 28%, or at least 30% of the total amount of the sRAGE-Ig fusion protein. In a further embodiment of any of the embodiments of this paragraph, a site may be considered aglycosylated wherein the number of carbohydrate residues attached to a site is 3 or less, or 2 or less, or 1 or less.

In another embodiment, the percentage of the amount of the fusion protein in the fully glycosylated form is less than 67%, or less than 65%, or less than 60%, or less than 55%, or less than 50%, or less than 45% of the total amount of the sRAGE-Ig fusion protein. In another embodiment, the percentage of the amount of the fusion protein in the fully glycosylated form is less than the percentage of the amount of the fusion protein in all of the non-fully glycosylated forms. For example, in the case of a fusion protein having three potential sites of glycosylation, the percentage of the amount of the fusion protein in the fully glycosylated form (i.e., triple glycosylation) is less than the percent of the amount of fusion protein in the double, mono, and aglycosylated forms combined. In a further embodiment of any of the embodiments of this paragraph, a site may be considered aglycosylated wherein the number of carbohydrate residues attached to a site is 3 or less, or 2 or less, or 1 or less.

In another embodiment, the fusion protein comprises at least two amino acid residues that may be glycosylated. In another embodiment, the fusion protein comprises at least three amino acid residues that may be glycosylated. In another embodiment, number of potential sites of glycosylation in the fusion protein is two. In another embodiment, number of potential sites of glycosylation in the fusion protein is three. In another embodiment, the RAGE ligand binding site comprises an amino acid residue that may be glycosylated. In another embodiment, wherein the fusion protein comprises at least two amino acid residues that may be glycosylated, a first potential site of glycosylation is an amino acid residue of the RAGE ligand binding site and a second potential site of glycosylation is an amino acid residue of the immunoglobulin polypeptide. In another embodiment, wherein the fusion protein comprises at least three amino acid residues that may be glycosylated, a first potential site of glycosylation is an amino acid residue of the RAGE ligand binding site, a second potential site of glycosylation is an amino acid residue of the RAGE polypeptide, and a third potential site of glycosylation is an amino acid residue of the immunoglobulin polypeptide. In a further embodiment of any of the embodiments of this paragraph, a site may be considered aglycosylated wherein the number of carbohydrate residues attached to a site is 3 or less, or 2 or less, or 1 or less.

When used within the context of a composition comprising an amount of a fusion protein comprising a RAGE polypeptide linked to an immunoglobulin polypeptide, "immunoglobulin polypeptide" includes a preserved FcRn scavenger receptor binding site at the junction of the $C_H2$ and $C_H3$ domains of the immunoglobulin. The immunoglobulin polypeptide may be a fragment of or the entire heavy chain from any one of the known heavy chain isotypes: IgG (γ), IgM (μ), IgD (δ), IgE (ε), or IgA (α). In addition, the heavy chain (or portion thereof) may be derived from any one of the known heavy chain subtypes: IgG1 (γ1), IgG2 (γ2), IgG3 (γ3), IgG4 (γ4), IgA1 (α1), IgA2 (α2), or mutations of these isotypes or subtypes that alter the biological activity. In an embodiment, the immunoglobulin polypeptide may contain portions or domains of different immunoglobulin isotypes and/or heavy chain subtypes. In an embodiment, the immunoglobulin polypeptide is of the IgG1 subtype. In another embodiment, the immunoglobulin polypeptide is of the IgG2 subtype. In yet another embodiment, the immunoglobulin polypeptide is of the IgG3 subtype. In another embodiment, the immunoglobulin polypeptide is of the IgG4 subtype. In another embodiment, the immunoglobulin polypeptide comprises a fragment of one of the heavy chain fragments of an Fc fragment of an immunoglobulin. In another embodiment, the immunoglobulin polypeptide comprises a heavy chain of an immunoglobulin. In another embodiment, the immunoglobulin polypeptide and the fusion protein does not include the hinge region of the immunoglobulin.

In certain embodiments, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991, each of which is incorporated herein by reference in its entirety) are expressed in accordance with systems and methods of the present invention (for review, see Naismith and Sprang, 1995-96, J. Inflamm. 47:1-7, incorporated herein by reference in its entirety). According to some embodiments, a tumor necrosis factor inhibitor comprises a soluble TNF receptor. In certain embodiments, a tumor necrosis factor inhibitor comprises a soluble TNFR-Ig. In certain embodiments, TNF inhibitors of the present invention are soluble forms of TNFRI and TNFRII. In further embodiments, the TNF inhibitor comprises a murine soluble TNFRII-Fc fusion protein. See, e.g., WO 2004/016229 at FIG. 2B). In certain embodiments, TNF inhibitors of the present invention are soluble TNF binding proteins. In certain embodiments, TNF inhibitors of the present invention are TNFR-Ig fusion proteins, e.g., TNFR-Fc or etanercept. As used herein, "etanercept," refers to TNFR-Fc, which is a dimer of two molecules of the extracellular portion of the p75 TNF-α receptor, each molecule consisting of a 235 amino acid Fc portion of human IgG1.

In certain embodiments, receptors to be produced in accordance with the present invention are receptor tyrosine kinases (RTKs). The RTK family includes receptors that are crucial for a variety of functions numerous cell types (see, e.g., Yarden and Ullrich, 1988, Ann. Rev. Biochem. 57:433-478; Ullrich and Schlessinger, 1990, Cell 61:243-254, incorporated herein by reference). Non-limiting examples of RTKs include tumor necrosis factor alpha and beta receptors (TNFR-1; EP 417,563 published Mar. 20, 1991; and TNFR-2, EP 417,014 published Mar. 20, 1991; for review, see Naismith and Sprang, supra, incorporated herein by reference), members of the fibroblast growth factor (FGF) receptor family, members of the epidermal growth factor receptor (EGF) family, platelet derived growth factor (PDGF) receptor, tyrosine kinase with immunoglobulin and EGF homology domains-I (TIE-1) and TIE-2 receptors (Sato et al., 1995, Nature 376:70-74, incorporated herein be reference) and c-Met receptor, some of which have been suggested to promote angiogenesis, directly or indirectly (Mustonen and Alitalo, 1995, J. Cell Biol. 129:895-898). Other non-limiting examples of RTK's include fetal liver kinase 1 (FLK-1) (sometimes referred to as kinase insert domain-containing receptor (KDR) (Terman et al., 1991, Oncogene 6:1677-83) or vascular endothelial cell growth factor receptor 2 (VEGFR-2)), fms-like tyrosine kinase-1 (Flt-1) (DeVries et al. 1992, Science 255; 989-991; Shibuya et al., 1990, Oncogene 5:519-524,), sometimes referred to as vascular endothelial cell growth factor receptor 1 (VEGFR-1), neuropilin-1, endoglin, endosialin, and Ax1. Those of ordinary skill in the art will be aware of other receptors that can be expressed in accordance with certain methods and compositions of the present invention.

In certain embodiments, the receptor to be produced in accordance with the present invention is a G-protein coupled receptor (GPCR). GPCRs are a major target for drug action and development, and have led to more than half of the currently known drugs (Drews, 1996, Nature Biotechnology, 14:1516) and GPCRs represent the most important target for therapeutic intervention with 30% of clinically prescribed drugs either antagonizing or agonizing a GPCR (Milligan, G. and Rees, S., TIPS, 20:118-124, 1999). Since these receptors have an established, proven history as therapeutic targets, production of GPCRs in accordance with the present invention is also of particular interest.

Glutamate receptors form a group of GPCRs that are important in neurotransmission. Glutamate is the major neurotransmitter in the CNS and is believed to have important roles in neuronal plasticity, cognition, memory, learning and some neurological disorders such as epilepsy, stroke, and neurodegeneration (Watson, S, and S. Arkinstall, In: The G-Protein Linked Receptor Facts Book, Academic Press, San Diego Calif., pp. 130-132, 1994). The vasoactive intestinal polypeptide (VIP) family is a group of related polypeptides whose actions are also mediated by GPCRs. Key members of this family are VIP itself, secretin, and growth hormone releasing factor (GRF). VIP has a wide profile of physiological actions including relaxation of smooth muscles, stimulation or inhibition of secretion in various tissues, modulation of various immune cell activities, and various excitatory and inhibitory activities in the CNS. Secretin stimulates secretion of enzymes and ions in the pancreas and intestine and is also present in small amounts in the brain.

Antibodies

Antibodies are proteins that have the ability to specifically bind a particular antigen. Given the large number of antibodies currently in use or under investigation as pharmaceutical or other commercial agents, production of antibodies in accordance with methods and compositions of the present invention is of particular interest.

Any antibody that can be expressed in a host cell may be used in accordance with the present invention. More preferably, the antibody comprises a potential glycosylation site in or near the antigen binding site of the antibody. In one embodiment, the antibody comprises a glycosylation site in the variable domain. In a further embodiment, the glycosylation site may be located in a CDR or a FR, even more preferably, the site occupancy of the glycosylation site affects binding of the antibody to its antigen.

In certain embodiments, an antibody to be expressed is a monoclonal antibody. In certain embodiments, the monoclonal antibody is a chimeric antibody. As is known in the art, a chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., 1985, Proc. Natl. Acad. Sci. U.S.A. 81:6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B, each of which is incorporated herein by reference in its entirety.

In certain embodiments, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the hypervariable region are replaced with residues from a non-human species that confer a desired antigen specificity or affinity. In certain embodiments, a humanized antibody has an amino acid sequence that is at least 80, 85, 90, 91, 92, 93, 94, 95, 96, 97, 98, 99 percent identical or higher to a human antibody. In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., 1983, Proc. Natl. Acad. Sci. U.S.A. 80: 7308-7312; Kozbor et al., 1983, Immunology Today 4: 7279; Olsson et al., 1982, Meth. Enzymol. 92: 3-16), and may be made according to the teachings of PCT Publication WO92/06193 or EP 0239400, each of which is incorporated herein by reference in its entirety).

In some cases, the antibodies of the disclosure are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex™, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al., 1994, Nature 368: 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg et al., 1994, supra; reviewed in Lonberg, 1994, Handbook of Experimental Pharmacology 113:49-101; Lonberg and Huszar, 1995, Intern. Rev. Immunol. 13: 65-93, Harding and Lonberg, 1995, Ann. N.Y. Acad. Sci. 764:536-546). See further, Taylor et al., 1992, Nucleic Acids Research 20:6287-6295; Chen et al., 1993, International Immunol. 5: 647-656; Tuaillon et al., 1993, Proc. Natl. Acad. Sci. USA 90:3720-3724; Choi et al., 1993, Nature Genetics 4:117-123; Chen et al., 1993, EMBO J. 12: 821-830; Tuaillon et al., 1994, J. Immunol. 152:2912-2920; Taylor et al., 1994, International Immunology 6: 579-591; and Fishwild et al., 1996, Nature Biotechnology 14: 845-851; U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another case, human antibodies of the disclosure can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise antibodies of the disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al., 2000, Proc. Natl. Acad. Sci. USA 97:722-727. Furthermore, cows carrying human heavy and light chain transchromosomes have been described in the art (Kuroiwa et al., 2002, Nature Biotechnology 20:889-894) and can be used to raise antibodies of the disclosure.

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Human monoclonal antibodies of the disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

In some embodiments, the antibody of the invention comprises at least one potential glycosylation site in the variable domain of the antibody. In certain embodiments, the glycosylation site is located in a CDR, and in other embodiments, the glycosylation site is located in a FR, or in both. In other embodiments, the antibody comprises at least one glycosylation site in a constant domain. Preferably, the antibody comprises a glycosylation site in the heavy chain constant domain.

In another aspect, the present invention provides a composition comprising an amount of a protein as described in any one of the embodiments herein, wherein at least 0.5% of the protein is aglycosylated. The percentage of the amount of protein relates to, inter alia, the number of protein molecules in a sample, and takes into account, where appropriate, the effect of glycosylation on the molecular weight of the protein. In another embodiment, the percentage of protein in the fully glycosylated form is less than 98%, or less than 97%, or less than 96%, or less than 95%, or less than 94%, or less than 93%, or less than 92%, or less than 91%, or less than 90%, or less than 87%, or less than 85%, or less than 80%, or less than 75%, or less than 70%, or less than 67%, or less than 65%, or less than 60%, or less than 55%, or less than 50%, or less than 45% of the total amount of the protein. In another embodiment, the percentage of the amount protein in the fully glycosylated form is less than the percentage of the amount of the protein in all of the non-fully glycosylated forms combined. For example, in the case of a protein having 2 potential sites of glycosylation, the percentage of the amount of the protein in the fully glycosylated form (i.e., both sites fully glycosylated with the full glycoform present) is less than the percent of the amount of the protein present in the mono (one site is aglycosylated) and fully aglycosylated (both sites are aglycosylated) forms combined wherein "aglycosylated" encompasses where the glycoform present at a site comprises at least one, at least two, at least three less carbohydrate moieties than the full glycoform present at the site when the protein is fully glycosylated. In a further embodiment, the present invention provides a composition comprising an amount of a protein as described in any one of the embodiments herein, wherein at least 0.5% of the protein is aglycosylated. In a further embodiment of any of the embodiments of this paragraph, a site may be considered aglycosylated wherein the number of carbohydrate residues attached to a site is 3 or less, or 2 or less, or 1 or less.

When used within the context of a composition comprising an amount of a protein, the "amount of a protein" is an amount that is detectable by typical analytical detection methods for proteins. In an embodiment, the amount of the protein is greater than 0.01 mg. In another embodiment, the amount of the protein is greater than 0.1 mg. In another embodiment, the amount of the protein is greater than 1.0 mg.

In another embodiment, the percentage of the amount of the protein in the aglycosylated form is at least 1%, or at least 2%, or at least 3%, or at least 4%, or at least 5%, or at least 6%, or at least 7%, at least 8%, or at least 9%, or at least 10%, or at least 12%, or at least 14%, or at least 16%, or at least 18%, or at least 20%, or at least 22%, or at least 24%, or at least 26%, or at least 28%, or at least 30% of the total amount of the protein. In a further embodiment of any of the embodiments of this paragraph, a site may be considered aglycosylated wherein the number of carbohydrate residues attached to a site is 3 or less, or 2 or less, or 1 or less.

In another embodiment, the percentage of protein in the fully glycosylated form is less than 95%, less than 90%, less than 85%, less than 80%, less than 75%, less than 70%, and less than 67%, or less than 65%, or less than 60%, or less than 55%, or less than 50%, or less than 45% of the total amount of the protein. In another embodiment, the percentage of the amount of the protein in the fully glycosylated form is less than the percentage of the amount of the protein in all of the non-fully glycosylated forms combined. For example, in the case of a protein having three potential sites of glycosylation, the percentage of the amount of the protein in the fully glycosylated form (i.e., three sites fully glycosylated) is less than the percent of the amount of the protein present in the double (two sites fully glycosylated), mono (one site fully glycosylated), and aglycosylated (all three sites aglycosylated) forms combined. Thus, where the number of potential glycosylation sites is n and n is an integer greater than or equal to 1, the amount of protein comprising n glycosylated sites is less than the total amount of the protein present in all of the forms having less than or equal to n−1 glycosylated sites. In a further embodiment of any of the embodiments of this paragraph, a site may be considered aglycosylated wherein the number of carbohydrate residues attached to a site is 3 or less, or 2 or less, or 1 or less.

In another aspect, the invention encompasses a composition comprising a protein where the protein is an antibody comprising a polypeptide chain comprising two potential glycosylation sites, where the amount of antibody in the fully glycosylated form (i.e., both sites are occupied and full glycoforms are present at each site) is less than amount of all of the non-fully glycosylated forms of the antibody combined. As would be understood by the skilled artisan, a canonical antibody typically comprises two heavy and two light chains. Where the heavy chain comprises two glycosylation sites (as diagrammatically depicted in FIG. 14 for an antibody comprising a glycosylation site in the variable domain and a glycosylation site in the constant domain) or where both heavy and light chains each comprise one glycosylation site, or where each light chain comprises two glycosylation site, a fully glycosylated antibody can comprise four glycosylation sites. Thus, in the case of a canonical antibody, the antibody can comprise four potential sites of glycosylation, two on each heavy chain, or one on each the heavy and the light chain, or two on the light chain, and the invention encompasses a composition where the percentage of the amount of the antibody in the fully glycosylated form (i.e., four sites fully glycosylated) is less than the percent of the amount of the antibody present in the mono aglycosylated (one site in one chain and two on the other chain are fully glycosylated), double aglycosylated (two sites in one chain, or one site on each chain, is fully glycosylated), triple (only one site in one chain is fully glycosylated) and fully aglycosylated (all four sites are aglycosylated) forms combined. In a further embodiment of any of the embodiments of this paragraph, a site may be considered aglycosylated or not fully glycosylated wherein the number of carbohydrate residues attached to a site is 3 or less, or 2 or less, or 1 or less.

In another aspect, the invention provides a composition comprising an amount of a protein, including an antibody, wherein at least 0.5% of the amount of the protein is aglycosylated.

When used within the context of an amount of a protein, including an antibody, the "amount of a protein" is an amount that is detectable by typical analytical detection methods for proteins. In an embodiment, the amount of the protein is greater than 0.01 mg. In another embodiment, the amount of the protein is greater than 0.1 mg. In another embodiment, the amount of the protein is greater than 1.0 mg.

In another embodiment, the percentage of the amount of the protein in the aglycosylated form is at least 1%, or at least 2%, or at least 3%, or at least 4%, or at least 5%, or at least 6%, or at least 7%, at least 8%, or at least 9%, or at least 10%, or at least 12%, or at least 14%, or at least 16%, or at least 18%, or at least 20%, or at least 22%, or at least 24%, or at least 26%, or at least 28%, or at least 30% of the total amount of the protein. In a further embodiment of any of the embodiments of this paragraph, a site may be considered aglycosylated wherein the number of carbohydrate residues attached to a site is 3 or less, or 2 or less, or 1 or less.

In another embodiment, the percentage of the amount of the protein in the fully glycosylated form is less than 97%, less than 96%, less than 95%, less than 94%, less than 93%, less than 92%, less than 91%, less than 90%, less than 85%, less than 80%, less than 75%, less than 70%, less than 67%, or less than 65%, or less than 60%, or less than 55%, or less than 50%, or less than 45% of the total amount of the protein in a composition. In another embodiment, the percentage of the amount of the protein in the fully glycosylated form is less than the percentage of the amount of the protein in all of the non-fully glycosylated forms in a sample. For example, in the case of a protein having three potential sites of glycosylation, the percentage of the amount of the protein in the fully glycosylated form (i.e., triple glycosylation) is less than the percent of the amount of protein in the double, mono, and aglycosylated forms combined in a sample. In a further embodiment of any of the embodiments of this paragraph, a site may be considered aglycosylated wherein the number of carbohydrate residues attached to a site is 3 or less, or 2 or less, or 1 or less.

In another embodiment, the protein comprises at least two amino acid residues that may be glycosylated. In another embodiment, the protein comprises at least three amino acid residues that may be glycosylated. In another embodiment, number of potential sites of glycosylation in the protein is two. In another embodiment, number of potential sites of glycosylation in the protein is three. In another embodiment, the protein comprises a ligand binding site comprising an amino acid residue that may be glycosylated. In another embodiment, wherein the protein comprises at least two amino acid residues that may be glycosylated, a first potential site of glycosylation is an amino acid residue of a ligand binding site and a second potential site of glycosylation is an amino acid residue in a non-ligand binding site of the protein. In another embodiment, wherein the protein comprises at least three amino acid residues that may be glycosylated, a first potential site of glycosylation is an amino acid residue in the ligand binding site, a second potential site of glycosylation is an amino acid residue also in the ligand binding site of the protein, and a third potential site of glycosylation is an amino acid residue not in the ligand binding site of the protein. In a further embodiment of any of the embodiments of this paragraph, a site may be considered aglycosylated wherein the number of carbohydrate residues attached to a site is 3 or less, or 2 or less, or 1 or less. In yet a further embodiment of any of the embodiments of this paragraph, protein encompasses a polypeptide chain of an antibody and a ligand binding site comprises an antigen binding site of an antibody.

As but one non-limiting example, an antibody that may be produced according to the present teachings is an anti-human IgE antibody. Anti-IgE antibodies are a particularly promising potential avenue of therapy in the treatment of asthma and other IgE-mediated diseases such as, but not limited to, allergic rhinitis and food allergies.

Anti-IgE antibodies are a potentially promising route of treatment of asthma since they may prevent binding of IgE to the FcεR1 and thereby prevent cross-linking of the FcεR1 receptors once the IgE antibodies bind an antigen. Prevention of cross-linking of IgE antibodies bound to FcεR1 receptors inhibits trigger of histamine release in a potentially anaphylactic reaction. Thus, anti-IgE antibodies useful to treat, e.g., asthma, ideally bind IgE and inhibit its interaction with the FcεR1 receptor but do not bind IgE bound to the receptor thereby ensuring that the antibodies cannot crosslink the receptors and trigger an anaphylactic reaction (termed "non-anaphylactic antibodies").

Examples of antibodies employable in the present invention, and methods of producing them, are described in Int. Appl. No. PCT/US2008/004286 filed Apr. 1, 2008, published as WO 2008/123999 on Oct. 16, 2008, which is incorporated by reference herein. While information on the amino acid sequences relating to this antibody is provided herein, further information can be found in WO 2008/123999; the sequences set forth in those applications are hereby incorporated herein by reference.

Certain uses for these antibodies to treat various IgE-mediated diseases, including, but not limited to asthma, allergic rhinitis and food allergies, were discussed in WO 2008/123999, which is incorporated by reference as if set forth in its entirety herein.

In some embodiments, the anti-IgE antibody, or antigen binding portion thereof, comprises a potential glycosylation site. The glycosylation site may be in a CDR, in a FR, or both, of the antibody, or antigen binding portion thereof.

In certain embodiments, the anti-IgE antibody or portion thereof directed against human IgE has an IC50 of 0.5 μg/mL or less as measured by its ability to reduce IgE binding in a cell binding assay using an RBL-2H3 cell line transfected with the human FcεR1.

In a further embodiment, the anti-IgE antibody or portion thereof has an IC50 of 0.5 μg/mL or less as measured by its ability to inhibit IgE-mediated degranulation of a RBL-2H3 cell line transfected with the human FcεR1, in which RBL-2H3 (FcεR1) cells were cultured with the anti-IgE antibody and human IgE for 48 hours, were washed to remove anti-IgE:IgE complexes, leaving IgE bound to FcεR1, then stimulated with a polyclonal anti-IgE antibody which crosslinks bound IgE, resulting in IgE-mediated degranulation. In a further embodiment, said $IC_{50}$ is less than 0.2 μg/mL, less than 0.1 μg/mL, less than 0.08 μg/mL or less than 0.02 μg/mL.

In another embodiment, the antibody or antigen-binding portion thereof directed against human IgE does not crosslink receptor-bound IgE and does not stimulate IgE-dependent degranulation of RBL-2H3 (FcεR1) cells cultured with human IgE for 48 hours then washed to remove unbound IgE. The antibody or antigen-binding portion thereof directed against human IgE of the invention does not have agonist activity with isolated RBL-2H3 (FcεR1).

In some embodiments, the antibody or antigen-binding portion thereof directed against human IgE does not crosslink receptor-bound IgE and does not stimulate IgE-dependent degranulation of human blood basophils cultured overnight with human IgE. The antibody or antigen-binding portion thereof directed against human IgE of the invention does not have agonist activity with isolated human blood basophils.

In other embodiments, the antibody or antigen-binding portion thereof directed against human IgE is highly selective for IgE over human IgA, IgG1 and IgG3.

In certain embodiments, the antibody or antigen-binding portion thereof binds to the full length of human IgE with an Affinity Constant, $K_D$, of 15 nM or less as measured by surface plasmon resonance (BIAcore).

In certain embodiments, the non-anaphylactic anti-IgE antibody is mAb 5.948.1 as disclosed in WO 2008/123999. The 5.948.1 antibody comprises a potential N-linked glycosylation site at amino acid residue number 73 of the heavy chain variable domain. More specifically, the glycosylation site is located in the third framework region (FR3) of the variable domain.

In some embodiments, the anti-IgE antibody or portion thereof, comprises a potential glycosylation site in the antigen binding domain. In certain embodiments, the antibody comprises a potential glycosylation site in a variable domain CDR or a FR.

In another embodiment, the anti-IgE antibody or portion thereof binds to the same epitope of human IgE as antibody 5.948.1.

In certain embodiments, the antibody, or antigen binding portion thereof, comprises a heavy chain variable domain amino acid sequence having at least 90%, preferably, at least 95%, more preferably, at least 97%, even more preferably, at least 98%, yet more preferably, at least 99%, sequence identity to SEQ ID NO:8, and a light chain variable domain amino acid sequence having at least 90%, preferably, at least 95%, more preferably, at least 97%, even more preferably, at least 98%, yet more preferably, at least 99%, sequence identity to SEQ ID NO:10. In another embodiment, the antibody, or antigen binding portion thereof, comprises a heavy chain variable domain amino acid sequence identical to SEQ ID NO:8 and a light chain variable domain amino acid sequence identical to SEQ ID NO:10.

In some embodiments, the antibody, or antigen binding portion thereof, comprises a heavy chain variable domain comprising the CDRs of SEQ ID NO:8 and further comprises a light chain variable domain comprising the CDRs of SEQ ID NO:10.

In certain embodiments, the antibody, or antigen binding portion thereof, comprises anti-CD33 antibody M195 as disclosed in U.S. Pat. Nos. 5,714,350 and 6,350,861, both to Co et al. (each of which is incorporated by reference herein as if set forth in its entirety). M195 comprises a glycosylation site within the antigen binding portion of the antibody; more specifically, M195 comprises an N-linked glycosylation site within the third framework region of the heavy chain variable domain. That is, during the process of humanization of the murine parent antibody, a glycosylation site was introduced into the heavy chain variable domain at FR3. Removal of the glycosylation site by mutagenesis increased binding of the antibody to CD33. Although it was known that approximately 20% of antibodies comprise a glycosylation site within the variable domain, it was believed that glycosylation in the antigen binding fragment of an antibody had no effect on antigen binding. See Sox & Hood, 1970, Proc. Natl. Acad. Sci. USA 66:975. Indeed, it had been reported that glycosylation at CDR2 actually increased binding of an antibody to its antigen, α-(1,6)-dextran (Wallick et al., 1988, J. Exp. Med. 168:1099; Wright et al., 1991, EMBO J. 10:2717). Thus, the skilled artisan would appreciate, once armed with the disclosure provided herein, that an antibody of interest should be assessed for the presence of a potential glycosylation site. This assessment can be performed using a variety of methods well-known in the art, including, but not limited to, those provided herein, such as, amino acid sequence analysis and/or chromatographic techniques that can identify the presence of glycosylation in a protein.

Once an antibody has been determined to comprise a potential glycosylation site in the variable domain or antigen binding portion, one skilled in the art would understand that the invention encompasses reducing the level of glycosylation of the antibody according to the novel methods provided herein which do not require alteration of the amino acid sequence of the antibody. The skilled artisan armed with the teachings provided herein would further understand that the novel methods provided herein permit the reduction in the level of glycosylation of an antibody without altering the amino acid sequence of the variable region. Further, one skilled in the art would understand that altering even a single amino acid in an antibody variable domain may have a dramatic deleterious effect on antigen binding. Therefore, the novel methods provided herein enable the reduction of glycosylation of an antibody, which may improve the binding characteristics of the antibody, without altering the amino acid sequence of the variable domain.

In certain embodiments, decreasing or abolishing the glycosylation of a protein, increases the binding of the protein to at least one ligand or antigen of a receptor or antibody, respectively, compared with the binding of an otherwise identical but fully glycosylated protein to the identical ligand or antigen.

In other embodiments, even where there may be no effect on the biological activity of the less glycosylated protein compared with an otherwise identical but more or fully glycosylated protein, the skilled artisan would appreciate that production of aglycosylated protein may provide a substantial manufacturing advantage. That is, especially, but not limited to, the production of proteins comprising at least two glycans and/or where the level of glycan occupancy and/or the glycoform present at each site may be difficult to control, the novel methods provide useful methods for producing a controlled glycan to either meet a specification (e.g., no glycosylation) and/or to decrease lot and/or batch failures. Thus, the skilled artisan would appreciate, once armed with the teachings provided herein, that the present invention provides novel methods to improve robustness of cell culture manufacturing processes for glycoproteins even where no detectable difference in biological activity for the decreased glycosylation/aglycosylated protein is achieved.

In another embodiment, the protein of the invention, which comprises a lower level of glycosylation, may be useful for x-ray crystallography studies and tryptic digest studies (see, e.g., Chaplin et al., 1991, GBH Monographs 15 (Protein): 279-282).

Alternatively or additionally, where a protein of the invention comprises an immunoglobulin domain, e.g., the protein is an antibody or a fusion protein comprising a portion of an Ig (e.g., an Fc portion), it may be useful to combine amino acid modifications with one or more further amino acid modifications that alter the biological characteristics of the protein.

In addition or alternative to modifications made within the framework or CDR regions, glycoproteins of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these aspects is described in further detail below. The numbering of residues in the Fc region is that of the EU index of Kabat.

In one case, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another case, the Fc hinge region of an antibody is mutated to decrease the biological half life of the antibody. More specifically, one or more amino acid mutations are introduced into the $C_H2$-$C_H3$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another case, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the $C_H1$ or CL region to contain a salvage receptor binding epitope taken from two loops of a $C_H2$ domain of an Fc region of an IgG, as described in U.S. Pat. Nos. 5,869,046 and 6,121,022 by Presta et al.

In yet other cases, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another case, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields et al., 2001 J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A. For example, the 22B5/DLE antibody described herein uses the IgG1 subclass of the IgG isotype, but has incorporated the following mutations (as compared to the wild-type IgG1 subclass) through site-directed mutagenesis: S247D; A338L; and I340E. Similarly, as described in more detail below, such S247D, A338L, and I340E mutations have been introduced into the 24C7, 1D9 and 2D2 monoclonal antibodies. As described further in the Examples, such mutations can increase the antibody's affinity to Fcγ receptors and thus increase its effector function. Thus, the invention encompasses an antibody comprising at least one mutation in the Fc region and having detectably greater ADCC response than an otherwise identical antibody not comprising the mutation.

In certain embodiments, the monoclonal, chimeric, single-chain or humanized antibodies described above may contain amino acid residues that do not naturally occur in any antibody in any species in nature. These foreign residues can be utilized, for example, to confer novel or modified specificity, affinity or effector function on the monoclonal, chimeric, single-chain or humanized antibody.

Clotting Factors

Clotting factors have been shown to be effective as pharmaceutical and/or commercial agents. Given the importance of recombinant clotting factors in the treatment of diseases such as Hemophilia, optimizing the expression of recombinantly produced clotting factors in accordance with methods and compositions of the present invention is of particular interest. One non-limiting example of a clotting factor that can be produced in accordance with the present invention is Coagulation Factor IX (Factor IX, or "FIX"). FIX is a single-chain glycoprotein whose deficiency results in Hemophilia B, a disorder in which the blood of the sufferer is unable to clot. Thus, any small wound that results in bleeding is potentially a life-threatening event.

FIX has multiple glycosylation sites including both N-linked and O-linked carbohydrates. FIX produced by Chinese Hamster Ovary ("CHO") cells in cell culture exhibits some variability in the Serine 61 oligosaccharide chain. These different glycoforms, and other potential glycoforms, may have different abilities to induce clotting when administered to humans or animals and/or may have different stabilities in the blood, resulting in less effective clotting.

Hemophilia A, which is clinically indistinguishable from Hemophilia B, is caused by a defect in human clotting factor VIII, another glycoprotein that is synthesized as a single chain zymogen and then processed into a two-chain active form. The present invention may also be employed to control or alter the glycosylation pattern of clotting factor VIII in order to modulate its clotting activity. Other glycoprotein clotting factors that can be produced and whose glycosylation pattern can be controlled or altered in accordance with the present invention include for example, but are not limited to, tissue factor and von Willebrands factor.

Enzymes

Another class of polypeptides that have been shown to be effective as pharmaceutical and/or commercial agents and that can desirably be produced according to the teachings of the present invention includes enzymes. Given the importance of recombinant enzymes in the treatment of diseases and other commercial and pharmaceutical uses, production of enzymes in accordance with the present invention is of particular interest.

As but one non-limiting example, a deficiency in glucocerebrosidase (GCR) results in a condition known as Gaucher's disease, which is caused by an accumulation of glucocerebrosidase in lysosomes of certain cells. Subjects with Gaucher's disease exhibit a range of symptoms including splenomegaly, hepatomegaly, skeletal disorder, thrombocytopenia and anemia. Friedman and Hayes showed that recombinant GCR (rGCR) containing a single substitution in the primary amino acid sequence exhibited an altered glycosylation pattern, specifically an increase in fucose and N-acetyl glucosamine residues compared to naturally occurring GCR (see U.S. Pat. No. 5,549,892, incorporated herein by reference in its entirety). Thus, production of GCR in accordance with methods of the present invention is contemplated. Those of ordinary skill in the art will be aware of other desirable enzymes that may be produced in accordance with methods of the present invention.

Growth Factors and Other Signaling Molecules

Another class of polypeptides that have been shown to be effective as pharmaceutical and/or commercial agents and that can desirably be produced according to the teachings of the present invention includes growth factors and other signaling molecules. Given the biological importance of growth factors and other signaling molecules and their importance as potential therapeutic agents, production of these molecules in accordance with methods and compositions of the present invention is of particular interest. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; bone morphogenetic proteins (BMP); interferons such as interferon-alpha, -beta, and -gamma; colony stimulating factors (CSFs), e.g., M-CSF, GM-CSF, and G-CSF; interleukins (ILs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; plasminogen activators, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with the present invention.

Introduction of Nucleic acids for the Expression of Polypeptide into Host Cells

In certain embodiments, a nucleic acid molecule introduced into the cell encodes the polypeptide desired to be expressed according to the present invention. In certain embodiments, a nucleic acid molecule may encode a gene product that induces the expression of the desired polypeptide by the cell. For example, the introduced genetic material may encode a transcription factor that activates transcription of an endogenous or heterologous polypeptide. Alternatively or additionally, the introduced nucleic acid molecule may increase the translation or stability of a polypeptide expressed by the cell.

The nucleic acid may be any nucleic acid encoding a protein comprising at least one potential glycosylation site, N- or O-linked. In other embodiments, the nucleic acid encodes a protein comprising at least one N-linked and one O-linked potential glycosylation site. The presence of a potential glycosylation site may be known for the particular protein or it may be predicted based on factors well-known in the art, including, but not limited to, the presence of a canonical glycosylation site in the amino acid sequence of the protein, numerous freely available computer software programs for predicting glycosylation sites, and the like. In other embodiments, the protein is known to be glycosylated, such proteins include, but are not limited to, antibodies and a wide plethora of glycoproteins, e.g., as those set forth in WO 2004/099231. Preferably, the glycosylation site is known to be within a portion of the protein associated with or involved in the biological function of the protein, such as, but not limited to, the site mediates the interaction of the protein with another protein. Even more preferably, the glycosylation of the protein is known to affect the biological function of the protein. However, any protein comprising a potential glycosylation site may be produced using the novel methods provided herein and any effect on a function of interest, e.g., interacting with another protein, may be assessed. That is, a function of interest of the protein produced according to the methods of the invention in the presence of a glycosylation inhibitor may be compared with the function of an otherwise identical protein produced under otherwise identical conditions but in the absence of a glycosylation inhibitor, thereby assessing whether glycosylation affects the function of interest. Where glycosylation affects a function of interest of a protein, the protein is a candidate to be produced according to the methods of the present invention. Thus, any therapeutic protein of interest where glycosylation affects, mediates, or is associated with a therapeutic function of the protein, may be produced by the novel methods of the invention.

The nucleic acid sequence encoding a protein of interest may be obtained by methods well known in the art and many are readily available from a number of databases. In certain embodiments, the sequence is known in the art. See, e.g., human RAGE sequence is available from GenBank (Accession no. NM_001136) and the sequences of various RAGE-Ig fusion proteins are available in the art, as are the sequences many other proteins, including antibodies, of interest. In other embodiments, where the nucleic acid sequence encoding a protein of interest is not known, the sequence may be obtained using standard methods well known in the art. In some embodiments, the nucleic acid sequence may, but need not be codon optimized to increase expression of the protein in the host cell used in the methods of the invention. Techniques for codon optimization to increase host cell expression of a nucleic acid of interest are well known in the art, and include, but are not limited to, those described in Angov et al. (2008, PloS ONE 3:e2189 [available at www.plosone.org]), and Hatfield & Roth (2007, Biotechnol. Ann. Rev. 13:27-42) and protein expression optimization services are also commercially available from, e.g., CODA Genomics, Inc. (Laguna Hills, Calif.) and GENEART AG (Regensburg, Germany).

Once obtained, the nucleic acid encoding the therapeutic protein of the invention is then introduced into a host cell. Methods suitable for introducing nucleic acids sufficient to achieve expression of a polypeptide of interest into host cells are known in the art. See, for example, Gething et al., 1981, Nature 293:620-625; Mantei et al., 1979, Nature, 281:40-46; Levinson et al. EP 117,060; and EP 117,058, each of which is incorporated herein by reference. For mammalian cells, common methods of introducing genetic material into the cell include the calcium phosphate precipitation method of Graham and van der Erb, 1978, Virology 52:456-457 or the Lipofectamine™ (Gibco BRL) Method of Hawley-Nelson, 1993, Focus 15:73. General aspects of mammalian cell host system transformations have been described by Axel in U.S. Pat. No. 4,399,216. For various techniques for introducing genetic material into mammalian cells, see Keown et al., 1990, Methods in Enzymology 185:527-537; Mansour et al., 1988, Nature, 336:348-352; Sambrook and Russell, 2001, In: Molecular Cloning, A Laboratory Approach, Cold Spring Harbor Press, Cold Spring Harbor, N.Y.; and Ausubel et al., 2002, In: Current Protocols in Molecular Biology, John Wiley & Sons, NY.

In certain embodiments, the nucleic acid to be introduced is in the form of a naked nucleic acid molecule. In some aspects of these embodiments, the nucleic acid molecule introduced into a cell consists only of the nucleic acid encoding the polypeptide and the necessary genetic control elements. In some aspects of these embodiments, the nucleic acid encoding the polypeptide (including the necessary regulatory elements) is contained within a plasmid vector. Non-limiting representative examples of suitable vectors for expression of polypeptide in mammalian cells include pcDNA1; pCD, see Okayama, et al., 1985, Mol. Cell Biol. 5:1136-1142; pMClneo Poly-A, see Thomas, et al., 1987, Cell 51:503-512; a baculovirus vector such as pAC 373 or pAC 610; CDM8 (Seed, 1987, Nature 329:840) and pMT2PC (Kaufman et al., 1987, EMBO J. 6:187-195). In certain embodiments, the nucleic acid molecule to be introduced into a cell is contained within a viral vector. For example, the nucleic acid encoding the polypeptide may be inserted into the viral genome (or a partial viral genome). The regulatory elements directing the expression of the polypeptide can be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Additionally or alternatively, naked DNA can also be introduced into cells by forming a mixture of the DNA and DEAEdextran and incubating the mixture with the cells or by incubating the cells and the DNA together in an appropriate buffer and subjecting the cells to a high-voltage electric pulse (i.e., by electroporation). In some embodiments, naked DNA is introduced into cells by mixing the DNA with a liposome suspension containing cationic lipids. The DNA/liposome complex is then incubated with cells. Naked DNA can also be directly injected into cells by, for example, microinjection.

Additionally or alternatively, naked DNA can be introduced into cells by complexing the DNA to a cation, such as polylysine, which is coupled to a ligand for a cell-surface receptor (see for example Wu and Wu, 1988, J. Biol. Chem. 263:14621; Wilson et al., 1992, J. Biol. Chem. 267:963-967; and U.S. Pat. No. 5,166,320). Binding of the DNA-ligand complex to the receptor facilitates uptake of the DNA by receptor-mediated endocytosis.

Use of viral vectors containing particular nucleic acid sequences, e.g., a cDNA encoding a polypeptide, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid.

Defective retroviruses are well characterized for use in gene transfer for gene therapy purposes (for a review see Miller, A. D., Blood 76:271, 1990). A recombinant retrovirus can be constructed having a nucleic acid encoding a polypeptide of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques.

The genome of an adenovirus can be manipulated such that it encodes and expresses a polypeptide of interest but is inactivated in terms of its ability to replicate in a normal lytic viral life cycle. See, for example, Berkner et al., BioTechniques 6:616, 1988; Rosenfeld et al., Science 252:431-434, 1991; and Rosenfeld et al., Cell 68:143-155, 1992. Suitable adenoviral vectors derived from the adenovirus strain Ad type 5 d1324 or other strains of adenovirus (e.g., Ad2, Ad3, Ad7 etc.) are known in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., Proc. Natl. Acad. Sci. USA 89:6482-6486, 1992), hepatocytes (Herz and Gerard, Proc. Natl. Acad. Sci. USA 90:2812-2816, 1993) and muscle cells (Quantin et al., Proc. Natl. Acad. Sci. USA 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra; Haj-Ahmand and Graham, J. Virol 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129, 1992). It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol. 63:3822-3828, 1989; and McLaughlin et al., J. Virol. 62:1963-1973, 1989). Vectors containing as little as 300 base pairs of AAV can be packaged and can integrate. Space for exogenous DNA is limited to about 4.5 kb. An AAV vector such as that described in Tratschin et al., (Mol. Cell. Biol. 5:3251-3260, 1985) can be used to introduce DNA into cells. A variety of nucleic acids have been introduced into different cell types using AAV vectors (see for example Hermonat et al., Proc. Natl. Acad. Sci. USA 81:6466-6470, 1984; Tratschin et al., Mol. Cell. Biol. 4:2072-2081, 1985; Wondisford et al., Mol. Endocrinol. 2:32-39, 1988; Tratschin et al, J. Virol. 51:611-619, 1984; and Flotte et al., J. Biol. Chem. 268:3781-3790, 1993).

In some embodiments, the invention encompasses use of mammalian artificial chromosomes using, e.g., Artificial Chromosomal Expression (ACE) technology to introduce the DNA or gene of interest into a host cell to produce cell lines expressing recombinant proteins. Compared to traditional techniques, these mammalian artificial chromosomes offer advantages for cellular protein production on account of their high carrying capacity and ability to self-replicate without relying on the integration into the host genome. Previously, it has been demonstrated that large satellite DNA-based artificial chromosomes, termed ACEs (Artificial Chromosome Expression), can readily be generated de novo in a variety of host cell backgrounds (Csonka et al., 2000, J. Cell Sci. 113:3207-3216; Hadlaczky, 2001, Curr. Opin. Mol. Ther. 3:125-132; Lindenbaum et al., 2004, Nucleic Acids Research 32:21; Perez et al., 2004, Bioprocessing J. July/August 2004:61-68; Stewart et al., 2002, Gene Ther. 9:719-723; Vanderbyl et al., 2005, Exp. Hematol. 33:1470-14765).

When the method used to introduce nucleic acid molecules into a population of cells results in modification of a large proportion of the cells and efficient expression of the polypeptide by the cells, the modified population of cells may be used without further isolation or subcloning of individual cells within the population. That is, there may be sufficient production of the polypeptide by the population of cells such that no further cell isolation is needed and the population can be immediately be used to seed a cell culture for the production of the polypeptide. In some embodiments, it may be desirable to isolate and expand a homogenous population of cells from a single cell that efficiently produces the polypeptide.

Alternative to introducing a nucleic acid molecule into a cell that encodes a polypeptide of interest, an introduced nucleic acid may encode another polypeptide, protein or regulatory element that induces or increases the level of expression of the protein or polypeptide produced endogenously by a cell. For example, a cell may be capable of expressing a particular polypeptide but may fail to do so without additional treatment of the cell. Similarly, the cell may express insufficient amounts of the polypeptide for the desired purpose. Thus, an agent that stimulates expression of the polypeptide of interest can be used to induce or increase expression of that polypeptide by the cell. For example, an introduced nucleic acid molecule may encode a transcription factor that activates or upregulates transcription of the polypeptide of interest. Expression of such a transcription factor in turn leads to expression, or more robust expression, of the polypeptide of interest. Similarly, the introduced nucleic acid molecule may contain one or more regulatory elements that titrate away one or more transcriptional repressors from a regulatory region of the polypeptide of interest.

In certain embodiments, a nucleic acid that directs expression of the polypeptide is stably introduced into the host cell. In certain embodiments, a nucleic acid that directs expression of the polypeptide is transiently introduced into the host cell. One of ordinary skill in the art will be able to choose whether to stably or transiently introduce the nucleic acid into the cell based on his or her experimental needs.

A gene encoding the polypeptide of interest may optionally be linked to one or more regulatory genetic control elements. In some embodiments, a genetic control element directs constitutive expression of the polypeptide. In some embodiments, a genetic control element that provides inducible expression of a gene encoding the polypeptide of interest can be used. Use of an inducible genetic control element (e.g., an inducible promoter) allows for modulation of the production of the polypeptide in the cell. Non-limiting examples of potentially useful inducible genetic control elements for use in eukaryotic cells include hormone-regulated elements (see e.g., Mader, S, and White, J. H., Proc. Natl. Acad. Sci. USA 90:5603-5607, 1993), synthetic ligand-regulated elements (see, e.g. Spencer, D. M. et al., Science 262:1019-1024, 1993) and ionizing radiation-regulated elements (see e.g., Manome, Y. et al., Biochemistry 32:10607-10613, 1993; Datta, R. et al., Proc. Natl. Acad. Sci. USA 89:10149-10153, 1992). Additional cell-specific or other regulatory systems known in the art may be used in accordance with methods and compositions described herein.

In certain embodiments, the nucleic acid sequence encoding the polypeptide is codon optimized to increase the level of expression in any particular cell. Methods for codon optimization are well known in the art, and including those describe in, e.g., Angov et al. (2008, PloS ONE 3:e2189 [available at www.plosone.org]), and Hatfield & Roth (2007, Biotechnol. Ann. Rev. 13:27-42). Further, codon optimization services are commercially available from, e.g., CODA Genomics, Inc. (Laguna Hills, Calif.) and GENEART AG (Regensburg, Germany).

In other embodiments, where the polypeptide comprises a signal sequence, the endogenous signal sequence naturally associated with the polypeptide may be replaced with a signal sequence not normally associated with the polypeptide to improve the level of expression of the polypeptide in cultured cells. That is, the polypeptide of the invention may be expressed as a fusion protein polypeptide fused with a heterologous peptide, which is preferably a signal sequence or other polypeptide having a specific cleavage site at the N-terminus of the mature protein or polypeptide (e.g., at Ala22 or Glu23 of human RAGE). The heterologous sequence selected is preferably one that is recognized and processed (i.e., cleaved by signal peptidase) by the host cell. For prokaryotic host cells that do not recognize and process the native signal sequence, the signal sequence may be substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α-factor leader (including *Saccharomyces* and *Kluyveromyces* α-factor leaders), or acid phosphatase leader, the *C. albicans* glucoamylase leader, or a signal described in, e.g., WO 1990/13646. In mammalian cell expression, mammalian signal sequences as well as viral secretory leaders, for example, the human interleukin-3 signal sequence (amino acid sequence MSRLPVLLLLQLLVRPAMA [SEQ ID NO:19]; encoded by the nucleic acid sequence ATGAGCCGCCTGCCCGTCCTGCTCCTGCTCCAACTCCTGGTCCGCCCCGCCATGGCT [SEQ ID NO:20]), the herpes simplex gD signal, are available. The nucleic acid for such precursor region is ligated in reading frame to the nucleic acid encoding the protein of interest.

In some embodiments, where the protein comprises an endogenous signal sequence, the nucleic acid sequence encoding the signal sequence may be codon optimized to increase the level of expression of the protein in a host cell.

One of ordinary skill in the art will be able to choose and, optionally, to appropriately modify the method of introducing genes that cause the cell to express the polypeptide of interest in accordance with the teachings of the present invention.

Isolation of Expressed Polypeptide

In certain embodiments, it is desirable to isolate and/or purify proteins or polypeptides expressed according to the present invention. In certain embodiments, an expressed polypeptide or protein is secreted into the medium and thus cells and other solids may be removed, as by centrifugation or filtering for example, as a first step in the purification process.

When using recombinant techniques, the protein can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter et al., 1992, Bio/Technology 10:163-167, describe a procedure for isolating antibodies which are secreted to the periplasmic space of *E. coli*. Briefly, cell paste is thawed in the presence of sodium acetate (pH 3.5), EBTA, and phenylmethylsulfonylfluoride (PMSF) over about 30 minutes. Cell debris can be removed by centrifugation.

Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide or protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, In: Protein Purification Principles and Practice, 2nd Edition, Springer-Verlag, New York, 1987; Higgins & Hames (eds.), In: Protein Expression: A Practical Approach, Oxford Univ Press, 1999; and Deutscher et al. (eds.), In: Guide to Protein Purification Methods in Enzymology, Methods in Enzymology Series, Vol 182, Academic Press, 1997, each of which is incorporated herein by reference in its entirety).

For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. One of ordinary skill in the art will be aware of other know affinity tags useful for isolating the expressed polypeptide. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Use of protease inhibitors are often advantageous when cells must be lysed in order to isolate and purify the expressed polypeptide or protein.

For antibodies, or proteins comprising an immunoglobulin Fc domain, the protein composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody or Fc fusion protein. Protein A can be used to purify antibodies that are based on human IgG1, IgG2 or IgG4 heavy chains (Lindmark et al., 1983, J. Immunol. Meth. 62:1-13). Protein G is recommended for all mouse isotypes and for human IgG3 (Guss et al., 1986, EMBO J. 5:1567-1575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody variant comprises a CH3 domain, the Bakerbond ABXTM resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody variant to be recovered.

Following any preliminary purification step(s), the mixture comprising the protein or antibody of interest and contaminants may be subjected to low pH hydrophobic interaction chromatography using an elution buffer at a pH between about 2.5-4.5, preferably performed at low salt concentrations (e.g., from about 0-0.25M salt).

One of ordinary skill in the art will appreciate that the exact purification technique may vary depending on the character of the polypeptide or protein to be purified, the character of the cells from which the polypeptide or protein is expressed, and the composition of the medium in which the cells were grown.

Pharmaceutical Compositions

The invention encompasses the preparation and use of pharmaceutical compositions comprising a polypeptide or protein of the invention as an active ingredient. The invention further encompasses s the preparation and use of pharmaceutical compositions comprising a polypeptide or protein of the invention as an active ingredient in combination with a second therapeutic agent, e.g., a chemotherapeutic agent, another antibody or protein, an immunostimulatory agent, and the like. Such a pharmaceutical compositions may consist of each active ingredient alone, as a combination of at least one active ingredient (e.g., an effective dose of a therapeutic protein, an effective dose of a therapeutic agent) in a form suitable for administration to a subject, or the pharmaceutical composition may comprise the active ingredient and one or more pharmaceutically acceptable carriers, one or more additional (active and/or inactive) ingredients, or some combination of these.

In one embodiment, the protein is administered parenterally (e.g., intravenously) in an aqueous solution while the second therapeutic agent (e.g., a chemotherapeutic agent, a second therapeutic protein, a second antibody, and the like) is administered orally in pill/capsule form. However, the skilled artisan would understand, based upon the disclosure provided herein, that the invention is not limited to these, or any other, formulations, doses, routes of administration, and the like. Rather, the invention encompasses any formulation or method of administering a protein in combination with a second therapeutic agent, including, but not limited to, administering each agent separately in a different formulation via a different route of administration, and administering the protein and the therapeutic agent in a single composition (e.g. where the second therapeutic agent is a protein, such as, another antibody, a second therapeutic protein, and the like), in an aqueous composition administered, inter alia, intravenously), among many others. Thus, the following discussion describes various formulations for practicing the methods of the invention comprising administration of any therapeutic protein in combination with any other therapeutic protein or compound, but the invention is not limited to these formulations, but comprises any formulation as can be readily determined by one skilled in the art once armed with the teachings provided herein for use in the methods of the invention.

The therapeutic protein used in the methods of the invention can be incorporated into pharmaceutical compositions suitable for administration to a subject. Typically, the pharmaceutical composition comprises the protein and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the protein or portion thereof.

The therapeutic protein used in the present invention may be in a variety of forms. These include, for example, liquid, semi solid and solid dosage forms, such as liquid solutions (e.g., injectable and infusible solutions), dispersions or suspensions, tablets, pills, powders, liposomes and suppositories. The preferred form depends on the therapeutic agent, the intended mode of administration and the therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the protein is administered by intravenous infusion or injection. In another preferred embodiment, the protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Advantageously, certain pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain cases, it will be useful to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

The therapeutic proteins can be administered by a variety of methods known in the art, including, without limitation, oral, parenteral, mucosal, by-inhalation, topical, buccal, nasal, and rectal. For many therapeutic applications, the preferred route/mode of administration is subcutaneous, intramuscular, intravenous or infusion. Non-needle injection may be employed, if desired. As will be appreciated by the skilled artisan, the route and/or mode of administration will vary depending upon the desired results.

In certain embodiments, the protein may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, ed., In: Sustained and Controlled Release Drug Delivery Systems, Marcel Dekker, Inc., New York (1978).

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the protein and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In one embodiment, the protein is administered in an intravenous formulation as a sterile aqueous solution containing about 1 mg/ml, preferably, about 5 mg/ml, or more preferably, about 10 mg/ml, or yet more preferably, about 15 mg/ml, or even more preferably, about 20 mg/ml of protein, with sodium acetate, polysorbate 80, and sodium chloride at a pH ranging from about 5 to 6. Preferably, the intravenous formulation is a sterile aqueous solution containing 5 or 10 mg/ml of protein, with 20 mM sodium acetate, 0.2 mg/ml polysorbate 80, and 140 mM sodium chloride at pH 5.5. Further, a solution comprising a protein can comprise, among many other compounds, histidine, mannitol, sucrose, trehalose, glycine, poly (ethylene)glycol, EDTA, methionine, and any combination thereof, and many other compounds known in the relevant art.

In one embodiment, part of the dose is administered by an intravenous bolus and the rest by infusion of the protein formulation. For example, a 0.01 mg/kg intravenous injection of the protein may be given as a bolus, and the rest of a predetermined protein dose may be administered by intravenous injection. A predetermined dose of the protein may be administered, for example, over a period of an hour and a half to two hours to five hours.

With regard to a second therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active therapeutic agents. Particularly contemplated additional agents include anti-emetics, anti-diarrheals, chemotherapeutic agents, cytokines, and the like.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Robinson, ed., Sustained and Controlled Release Drug Delivery Systems, Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in *Remington's Pharmaceutical Sciences*, Genaro, ed., Mack Publishing Co., Easton, Pa. (1985), which is incorporated herein by reference.

In one embodiment of the invention, the composition comprising a therapeutic protein comprises a sterile solution comprising 20 mM histidine buffer, pH 5.5, 84 mg/ml trehalose dehydrate, 0.2 mg/ml polysorbate 80, and 0.1 mg/ml disodium EDTA hydrate. In one aspect, the protein is packaged in clear glass vials with a rubber stopper and an aluminum seal. In another aspect, the vial contains about 20 mg/ml of the protein with a nominal fill of about 400 mg per vial.

The therapeutic protein composition of the invention can be administered to an animal, preferably a human. Where the composition comprises a combination of the therapeutic protein and a second therapeutic agent, the precise dosage administered of each active ingredient will vary depending upon any number of factors, including but not limited to, the type of animal and type of disease state being treated, the age of the animal and the route of administration.

The therapeutic protein may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The therapeutic protein may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The therapeutic protein and the second therapeutic agent (e.g., a second protein) can be co-administered in that they can be administered separately, on different dates or at different times of the day, as well as simultaneously or on the same date. Co-administration thus encompasses any temporal combination of administration of the protein and the second therapeutic agent such that administration of the two agents mediates a therapeutic benefit to the patient that is detectably greater than administration of either agent in the absence of the other.

A therapeutic protein and a second therapeutic agent combination of the invention may be co-administered with numerous other compounds (other antihormonal therapy agents, cytokines, chemotherapeutic and/or antiviral drugs, among many others). Alternatively, the compound(s) may be administered an hour, a day, a week, a month, or even more, in advance of the protein-therapeutic agent combination, or any permutation thereof. Further, the compound(s) may be administered an hour, a day, a week, or even more, after administration of radiation, stem cell transplant, or administration of any therapeutic agent (e.g., cytokine, chemotherapeutic compound, and the like), or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds, and the like.

Dosage Regimens

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the therapeutic protein and the particular therapeutic or prophylactic effect to be achieved, and (b) the limitations inherent in the art of compounding such an active compound for the treatment of sensitivity in individuals.

An exemplary, non limiting range for a therapeutically effective amount of therapeutic protein administered according to the invention is at least about 1 mg/kg, at least about 5 mg/kg, at least about 10 mg/kg, more than about 10 mg/kg, or at least about 15 mg/kg, for example about 1-30 mg/kg, or for example about 1-25 mg/kg, or for example about 1-20 mg/kg, or for example about 5-20 mg/kg, or for example about 10-20 mg/kg, or for example about 15-20 mg/kg, or for example, about 15 mg/kg. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Determining appropriate dosages and regiments for administration of the therapeutic protein are well-known in the relevant art and would be understood to be encompassed by the skilled artisan once provided the teachings disclosed herein.

In one embodiment, an anti-IgE antibody, or antigen binding portion thereof, of the invention is administered in an intravenous formulation as a sterile aqueous solution containing about 5 to 20 mg/ml of antibody, in an appropriate buffer system.

In one embodiment, for administration of low doses, part of the dose is administered by an intravenous bolus and the rest by infusion of the antibody formulation. For example, a 0.01 mg/kg intravenous injection of the antibody may be given as a bolus, and the rest of a predetermined antibody dose may be administered by intravenous injection. In another embodiment, the entire low dose is administered as a single bolus injection. For higher doses, e.g., 3 mg/kg, the antibody is not administered as a bolus, but the entire amount is administered by infusion. A predetermined dose of the antibody may be administered, for example, over a period of about an hour and a half to about five hours.

In one embodiment of the present invention, the therapeutic protein (e.g., sRAGE-Fc fusion protein, an antibody such as an anti-IgE antibody, and the like) is administered approximately every three weeks, more preferably, for about four cycles followed by every three months thereafter. In one aspect of this embodiment, the protein is administered at about 10 mg/kg.

The skilled artisan would appreciate that the combination of therapeutic protein of the invention and a second therapeutic protein or agent can be administered simultaneously or the protein of the invention and the second therapeutic protein or agent can be administered at different times. For instance, in one embodiment, the therapeutic protein is administered as a single injection and/or infusion and the second therapeutic agent (e.g., a non-protein compound) is administered once per day commencing before, during, or after administration of the protein. However, the present invention is not limited to any particular dosage or administration regimen for a therapeutic agent. Rather, the optimal dose, route and regimen for administration of the antibody and the therapeutic agent can be readily determined by one of ordinary skill in the relevant art using well-known methods.

For instance, a single dose or multiples doses of the therapeutic protein may be administered. Alternatively, at least one dose, or at least three, six or 12 doses may be administered. The doses may be administered, for example, every two weeks, every three weeks, monthly, every twenty days, every 25 days, every 28 days, every 30 days, every 40 days, every 6 weeks, every 50 days, every two months, every 70 days, every 80 days, every three months, every six months or yearly. In one aspect, the therapeutic protein is administered once every three weeks, preferably for four cycles, and then every three months thereafter. In addition, the second therapeutic agent or protein can be administered daily, several times or once per day, weekly, every other week, every third week, every fourth week, monthly, every three months, every six months, once per year, or any other period that provides a therapeutic benefit to the patient as determined by the skilled practitioner.

Uses for the Protein

The therapeutic proteins of the invention may be used as affinity purification agents. In this process, the proteins are immobilized on a solid phase such as SEPHADEX™ resin or filter paper, using methods well known in the art. The immobilized protein is contacted with a sample containing the binding partner to be purified, and thereafter the support is washed with a suitable solvent that will remove substantially all the material in the sample except the binding partner to be purified, which is bound to the immobilized protein. Finally, the support is washed with another suitable solvent, such as glycine buffer, that will release the binding partner from the immobilized protein.

The proteins may also be useful in diagnostic assays, e.g., for detecting expression of a binding partner of interest in specific cells, tissues, or serum. For diagnostic applications, the protein of the invention typically will be labeled with a detectable moiety. Numerous labels are available, including techniques for quantifying a change in fluorescence where the protein is labeled with a fluorophore. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to proteins, including antibodies or fragments thereof, are described in O'Sullivan et al., Methods for the Preparation of Enzyme-Antibody Conjugates for Use in Enzyme Immunoassay, in: Methods in Enzym. (Ed. J. Langone & H. Van Vunakis), Academic press, New York, 73: 147-166 (1981).

Sometimes, the label is indirectly conjugated with the protein. The skilled artisan will be aware of various techniques for achieving this. For example, the protein, e.g., an antibody or antigen-binding portion thereof, can be conjugated with biotin and any of the three broad categories of labels mentioned above can be conjugated with avidin, or vice versa. Biotin binds selectively to avidin and thus, the label can be conjugated with the protein in this indirect manner. Alternatively, to achieve indirect conjugation of the label with the protein, the protein is conjugated with a small hapten (e.g., digloxin) and one of the different types of labels mentioned above is conjugated with an anti-hapten antibody (e.g., anti-digloxin antibody). Thus, indirect conjugation of the label with the protein can be achieved.

In another embodiment of the invention, the protein need not be labeled, and the presence thereof can be detected using a labeled antibody which binds to the protein.

The proteins, including antibodies, of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample for binding with a limited amount of protein. The amount of target in the test sample is inversely proportional to the amount of standard that becomes bound to the protein. To facilitate determining the amount of standard that becomes bound, the proteins generally are insolubilized before or after the competition. As a result, the standard and test sample that are bound to the proteins may conveniently be separated from the standard and test sample which remain unbound.

Sandwich assays involve the use of two binding proteins, each capable of binding to a different binding domain, or epitope in the case of antibodies, of the protein to be detected. In a sandwich assay, the test sample to be analyzed is bound by a first antibody which is immobilized on a solid support, and thereafter a second binding protein, including a second antibody, binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, a biological sample may be fresh or frozen or may be embedded in paraffin and fixed with a preservative such as formalin, for example.

The proteins may also be used for in vivo diagnostic assays. Generally, the protein is labeled with a radionucleotide (such as $^{111}$In, $^{99}$Tc, $^{14}$C, $^{131}$I, $^{3}$H, $^{32}$P or $^{35}$S) so that the tissue where the protein binds with a binding partner, or in the case of an antibody, where the antibody binds with its antigen, can be localized using immunoscintiography. For example, an anti-IgE antibody of the present invention may be used to detect the amount of IgE present in, e.g., the lungs of an asthmatic patient. Or the RAGE fusion protein of the present invention may be used to detect the amount of a ligand present in a patient.

The protein of the present invention can be provided in a kit, i.e., packaged combination of reagents in predetermined amounts with instructions for performing the diagnostic assay. Where the protein is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In Vivo Uses for the Antibody

It is contemplated that the proteins of the present invention may be used to treat a mammal. In one embodiment, the protein is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the protein or may be used to study toxicity or pharmacokinetics of the protein of interest. In each of these embodiments, dose escalation studies may be performed on the mammal.

The protein is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the protein is suitably administered by pulse infusion, particularly with declining doses of the protein. Preferably the dosing is given by injections, most preferably intravenous or subcutaneous injections, depending in part on whether the administration is brief or chronic.

For the prevention or treatment of disease, the appropriate dosage of the antibody or protein will depend on the type of disease to be treated, the severity and course of the disease, whether the antibody variant is administered for preventive or therapeutic purposes, previous therapy, the patient's clinical history and response to the antibody variant, and the discretion of the attending physician. In certain embodiments, the anti-human IgE antibodies of the invention may be suitably administered to the patient at one time or over a series of treatments. Similarly, in other embodiments, the sRAGE-Ig fusion protein of the invention is administered to a patient at one time or over a series of treatments.

Depending on the type and severity of the disease, about 0.1 mg/kg to 150 mg/kg (e.g., 0.1-20 mg/kg) of protein is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen for an anti-LFA-1 or anti-ICAM-1 antibody is disclosed in WO 94/04188.

Uses for the sRAGE-Ig fusion protein of the invention to treat various diseases or disorders, are disclosed in, e.g., WO 2004/016229; WO 2006/017643; WO 2006/017647; WO 2007/094926; WO 2007/130302; and WO 2008/100670.

The protein composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the protein to be administered will be governed by such considerations, and is the minimum amount necessary to prevent, ameliorate, or treat a disease or disorder. The protein need not be, but is optionally formulated with one or more agents currently used to prevent or treat the disorder in question. The effective amount of such other agents depends on the amount of protein present in the formulation, the type of disorder or treatment, and other factors discussed above. These are generally used in the same dosages and with administration routes as used hereinbefore or about from 1 to 99% of the heretofore employed dosages.

The anti-IgE antibodies of the present invention which recognize IgE as their target may be used to treat "IgE-mediated disorders". These include diseases such as asthma, allergic rhinitis & conjunctivitis (hay fever), eczema, urticaria, atopic dermatitis, and food allergies. The serious physiological condition of anaphylactic shock caused by, e.g., bee stings, snake bites, food or medication, is also encompassed under the scope of this invention.

The sRAGE-Ig fusion proteins of the present invention which recognize advanced glycation end protucts (AGEs), amyloid beta (Aβ), serum amyloid A (SAA), S100, carboxymethyl lysine (CML), amphoterin and CD11b/CD18 as their target may be used to treat any disease, condition or disorder mediated by or associated with binding or RAGE to its ligand, i.e., "RAGE-mediated disorders". RAGE has been implicated in a variety of disease states and such RAGE-mediated disorders include, but are not limited to, a symptom of diabetes or a symptom of diabetic late complications, e.g., diabetic nephropathy, diabetic retinopathy, a diabetic foot ulcer, a cardiovascular complication, or diabetic neuropathy; amyloidosis, Alzheimer's disease, cancer, kidney failure, or inflammation associated with autoimmunity, inflammatory bowel disease, rheumatoid arthritis, psoriasis, multiple sclerosis, hypoxia, stroke, heart attack, hemorrhagic shock, sepsis, organ transplantation, or impaired wound healing; osteoporosis, kidney failure, transplant rejection, inflammation and/or rejection associated with transplantation, among others.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Control of Glycosylation: Decreased Glycan Site Occupancy Using Tunicamycin Glycosylation Inhibitor Affects RAGE Ligand Binding The Receptor for Advanced Glycation End products (RAGE) has been implicated in the pathology of a number of chronic disorders and as a consequence is being actively pursued as a target for therapeutic intervention. Recent studies have demonstrated that RAGE is a glycoprotein whose glycosylation state can affect binding to its ligands. In this study we have expressed a recombinant human sRAGE-Ig fusion protein and examined its glycosylation state and proteolytic processing. The sRAGE-Ig fusion protein has three N-linked glycosylation sites, two in the sRAGE domain and one in the Fc region which when expressed in CHO cells are approximately 70% fully occupied.

Tunicamycin treated cell culture was used to express site occupancy variants of this protein. Site occupancy variants were isolated and the impact of glycan occupancy on binding to the RAGE ligand S100b was assessed. The aglycosylated variant showed a ten fold increase in binding to S100b compared to the fully occupied version, whereas the doubly occupied variant showed an intermediate binding between the two.

In addition we found that approximately 20% of the CHO expressed sRAGE-Ig fusion protein is cleaved by the subtilisin-like protease furin, resulting in the loss of the RAGE domain. These studies provide insight into the post translational requirements of a recombinant RAGE molecule for optimum ligand binding activity and have highlighted potential challenges associated with expression of the full length protein in CHO cells.

The Receptor for Advanced Glycation End-products (RAGE) is a member of the immunoglobulin superfamily whose expression is up regulated in a number of human diseases including diabetes, chronic inflammation and Alzheimer's disease (Ramasamy et al., 2005, Glycobiology 15:16R-28R). The ligands for RAGE include advanced glycation endproducts (AGEs), which are heterogeneous structures resulting from exposure of lipids and proteins to reducing sugars with subsequent irreversible complex molecular rearragengements (Brownlee et al., 1988, New Eng. J. Med. 318:1315-1320; Schmidt et al., 1994, Arterioscler. Thromb. 14:1521-1528. In addition to AGEs, RAGE binds to multiple functionally and structurally diverse ligands including amyloid beta (Aβ), serum amyloid A (SAA), S100 (a proinflammatory member of the Calgranulin family), carboxymethyl lysine (CML), amphoterin and CD11b/CD18 (Bucciarelli et al., 2002, Cell Mol. Life Sci. 59:1117-128; Chavakis et al., 2004, Microbes Infect. 6:1219-1225; Kokkola et al., 2005, Scand. J. Immunol. 61:1-9; Schmidt et al., 2001, J. Clin. Invest. 108:949-955; Rocken et al., 2003, Am. J. Pathol. 162: 1213-1220).

Activation of RAGE by binding to its ligands in different tissues has been implicated in a variety of conditions (Hofmann et al., 1999, Cell 97:889-901; Wautier et al., 1995, J. Clin. Invest. 97:238-243; Teillet et al., 2000, J. Am. Soc. Nephrol. 11:1488-1497; Vlassara et. al., 1996, Finnish Med. Soc. DUODECIM, Ann. Med. 28:419-426; Hammes et al., 1999, Diabetologia 42:603-607), including Alzheimer's disease (Yan et al., 1996, Nature 382:685-691), and tumor invasion and metastasis (Taguchi et al., 2000, Nature 405:354-357).

The binding of ligands to the RAGE receptor is responsible for its up regulation (Schmidt et al., 2000, Biochim. Biophys. Acta 1498:99-111). Increased expression of the receptor results in cellular signaling and activation that leads to the pathology of chronic disease (Schmidt et al., 1999, Circ. Res. 84:489-497). One way to down regulate RAGE and interrupt the cycle of ligand engagement is to generate a "decoy" or soluble RAGE (sRAGE) lacking the transmembrane domain. Treatment with exogenous sRAGE has been shown to suppress the acceleration of diabetic atherosclerosis in a diabetic mouse model (Park et al., 1998, Nature Medicine 4:1025-1031) providing support for the idea that RAGE may be a useful target for therapeutic intervention (Hudson & Schmidt, 2004, Pharm Res 21:1079-1086, Schmidt & Stern, 2000, Trends Endocrinol. Metab. 11:368-375, Hudson et al., 2003, Arch. Biochem. Biophys. 419:80-88).

The sRAGE-Ig fusion protein described in this study is a recombinant molecule designed as a potential therapeutic decoy. The protein contains the ligand binding V-like domain and the constant-type-like C1 domain of human RAGE linked to the $C_H2$ and $C_H3$ domains of a human IgG1 heavy chain molecule (FIG. 1). Although sRAGE has been isolated from mice as a monomer (Hanford et al., 2004, J. Biol. Chem. 279:50019-50024) and has also been expressed in E. coli (Wilton et al., 2006, Protein Expression Purif. 47:25-35) and yeast (Ostendorp et al., 2006, Biochem. Biophys. Res. Commun. 347:4-11) as a monomer, here we report the expression of a human sRAGE-Ig fusion protein as a dimer. We describe the proteolytic cleavage and the glycosylation pattern of the sRAGE-Ig fusion protein when expressed in Chinese hamster ovary (CHO) cells. To assess the functional role of N-linked glycosylation of human RAGE on binding to its ligands, we used tunicamycin to produce N-linked site occupancy variants of the sRAGE-Ig fusion protein, and measured binding of the glycosylation variants to the RAGE ligand S100b.

Experimental Procedures

Production of a host cell line expressing the sRAGE-Ig fusion protein: CHO cell lines expressing the sRAGE-Ig fusion protein were produced by transfection via electroporation with a linearized expression plasmid containing the sRAGE-Ig cDNA encoding the amino acid sequence shown in FIG. 2 (SEQ ID NO:1). The nucleic acid encoding the sRAGE-Ig fusion protein comprised a sequence encoding the human RAGE signal sequence (the first 23 amino acids of SEQ ID NO:1). After transfection, cells were selected in methyl sulphoximine (MSX) and the conditioned medium ("CM") from surviving pools was screened by ELISA for protein production. Cells producing the fusion protein were transferred from static to suspension cultures and scaled up as non-clonal pools. Pools that had acceptable growth rates and titers in shake flask assays were capillary cloned. Clones were scaled up to suspension cultures and were progressed based on their growth and expression level in a shake flask assay. Conditioned medium was collected from both non-clonal pools and clonal candidates growing in shake flasks and purified by a small MabSelect column (GE Healthcare, Piscataway, N.J.) for product quality analysis. The clonal CHO cell line expressing the sRAGE-Ig fusion protein used for this study was chosen based on growth, titer and product quality characteristics and is representative of the total number of cell lines evaluated.

Tunicamycin treatment: The clonal CHO cell line expressing the sRAGE-Ig fusion protein was cultured to mid log phase in 50 mL of medium in a shake flask. Cells were treated with 5 µg/mL of tunicamycin (Sigma-Aldrich) dissolved in DMSO and incubated for 3 days at 37° C. in a shaking incubator. At the end of three days conditioned medium was collected, filtered and purified. Purified protein was analyzed via RP-HPLC for glycan site occupancy and peak fractions were collected for the S100b binding assay.

Purification of sRAGE-Ig protein from conditioned medium: Laboratory scale purification of protein was performed on a 5 mL HiTrap MabSelect column from GE Healthcare (Piscataway, N.J.) using an AKTA FPLC chromatography skid from GE Healthcare. The column was equilibrated with 5 column volumes (CV) of 50 mM phosphate, 1M NaCl, pH 7.0. The clarified CM was then applied to the column and washed with 10 CV of 50 mM phosphate, 1M NaCl, pH 7.0, followed by a wash with 5 CV of 25 mM acetate, pH 5.5. The protein was then eluted from the column using 25 mM acetate, pH 3.5 and the elution pool was collected as a single fraction based on 280 nm absorbance. The column was run at 5 mL/min throughout the operation. The purified protein pool was then dialyzed into a stabilizing buffer using 10 K dialysis cassettes from Pierce (Rockford, Ill.). The concentration of purified protein was determined using 280 nm absorbance on a spectrophotometer.

SDS-PAGE analysis of sRAGE-Ig, PNGaseF and furin digestion: Purified sRAGE-Ig fusion protein (178 µg) was digested with 7.5 mU of peptide-N-glycosidase F (PNGase F) (Cat. No. GKE-5006, Prozyme, San Leandro, Calif.) in a total volume of 250 µL of buffer for 30 hours at 37° C. 32 µg of purified sRAGE-Ig fusion protein was digested with 24 U of furin protease (Cat No. P8077S, New England Biolabs, Ipswich, Mass.) in a total volume of 100 µL of buffer for 15 hours at 37° C. Undigested and digested fusion protein samples were prepared in reducing SDS-PAGE sample buffer and 2.7 ug of total protein were loaded per lane and run on a 4-12% gradient NuPage bis-tris gel (Cat. No. NP0322, Invitrogen, Carlsbad, Calif.).

Analysis of sRAGE-Ig by Size Exclusion Chromatography (SEC): Purified sRAGE-Ig was diluted to 3 mg/mL in mobile phase (350 mM citrate, pH 6.0) and analyzed by SEC using an Alliance 2695 liquid chromatograph (Waters, Millford, Mass.). A Superdex 200 10/300 GL column was used for the separation (Cat. No. 17-5175-01, GE Healthcare, Piscataway, N.J.) with a flow rate of 0.75 mL/min for 40 min at ambient temperature. The detection used was absorbance at 280 nm.

Determination of Glycosylation site occupancy by RP-HPLC and Identification of Peaks by liquid chromatography/ mass spectroscopy (LC/MS): Glycosylation site occupancy of the sRAGE-Ig fusion protein was determined under reversed-phase HPLC conditions. An Agilent 1100 liquid chromatograph (Agilent Technologies, Palo Alto, Calif.) with a quaternary pump and UV detector was employed for HPLC separation. Data acquisition and integration were accomplished with Chemstation (Agilent) or Empower (Waters) software packages. Briefly, 20 µL of the protein solutions at 1.0 mg/mL were separated on a Zorbax 300SB-C18 column (Agilent) with a shallow gradient of HPLC grade water and acetonitrile (Sigma Aldrich, St. Louis, Mo.) at a flow rate of 0.3 mL/min. The initial gradient at time zero was set to 67% mobile phase A (water containing 0.1% of trifluoroacetic acid (ACS grade, Pierce, Rockford, Ill.) and 33% mobile phase B (acetonitrile containing 0.085% trifluoroacetic acid). From t=0 to 2 minutes, mobile phase B was increased to 34%, which was further increased to 36% from t=2 to 10 minutes, followed by a 10-minute equilibration at 67% mobile phase A and 33% mobile phase B. The detection was absorbance at 214 nm.

To characterize the mass profile of glycosylation site occupancy variants, the samples were analyzed by LC/MS using an Agilent 1100 liquid chromatograph coupled to a Micromass quadruple time-of-flight (Q-TOF) mass spectrometer (Q-TOF MS) (Waters, Milford, Mass.). The eluent from the reversed-phase separation was directed into the source of the mass spectrometer with 1:1 splitting. Mass spectra were averaged over each chromatographic peak, and were deconvoluted using the MaxEnt algorithm supplied with the Masslynx software.

Analysis of Released Glycans by Normal Phase HPLC (NPLC) with Fluorescent Detection: Samples were diluted to 0.25 mg and desalted using Nanosep (P/N OD010C34, Pall Life Sciences, East Hills, N.Y.) membrane filters with a molecular weight cutoff of 10 kilodaltons (MWCO 10K). N-glycans were released from the glycoprotein by incubation with PNGaseF (Cat. No. GKE-5006, Prozyme, San Leandro, Calif.) at 37° C. overnight. The enzymatic reaction was performed in the presence of β-mercaptoethanol (GKE-5006, Prozyme, San Leandro, Calif.) and SDS (Prozyme, San Leandro, Calif.). After release, protein was removed from released glycans using a Nanosep membrane filter (MWCO 10K). Samples containing the glycan portion were evaporated to dryness prior to the labeling reaction. Glycans were then labeled with 2-amino benzamide (2-AB) (GKK-404, Prozyme, San Leandro, Calif.) at 65° C. for 3-4 hours. Excess labelling reagent was removed using a GlycoClean S cartridge (GKK-4726, Prozyme, San Leandro, Calif.). Finally, the mixture of labeled glycans was analyzed by NPLC on an Agilent 1100 liquid chromatograph (Agilent Technologies, Palo Alto, Calif.) equipped with a fluorescence detector. The excitation (Ex) wavelength was 330 nm and the emission (Em) wavelength was 420 nm. A TSK-GEL Amide-80 column (250 mm×4.6 mm, 5 µm particle size) held at 30° C. was used for the separation (Tosoh Bioscience, South San Francisco, Calif.). A gradient separation was used at a flow rate of 0.4 mL/min, starting with 70% A and 30% B and increasing to 40% B over 90 min. Mobile phase B was then increased to 95% over 50 min, and to 100% over 5 min, and then down to 30% for re-equilibration. The mobile phases used were as follows: mobile phase A was acetonitrile and mobile phase B was 250 mM ammonium formate pH 4.4. An injection volume of 10 µL was used for the analysis.

Charge Profiling by Anion Exchange Chromatography: Samples were diluted to 0.5 mg and prepared as described above for normal-phase liquid chromatography (NPLC). The mixture of released and labeled glycans was analyzed by anion ion exchange high performance liquid chromatography (HPLC) on an Agilent 1100 liquid chromatograph (Agilent Technologies, Palo Alto, Calif.) equipped with a fluorescence detector. The excitation wavelength was 330 nm and the emission wavelength was 420 nm. A GlycoSepC column (100 mm×7.5 mm, 10 µm particle size) (GKI-4721, Prozyme, San Leandro, Calif.) at ambient temperature was used for the separation. A gradient separation was used at a flow rate of 0.5 mL/min, starting with 100% A and 0% B for 5 minutes, and increasing to 50% B over 45 minutes. Mobile phase B was then increased to 100% over 5 minutes and held for 5 minutes, and back to 0% for re-equilibration. The mobile phases used were as follows: mobile phase A was 20% acetonitrile, 80% water (v/v) and mobile phase B was 20% acetonitrile, 80% 250 mM ammonium acetate (v/v) pH 4.5. An injection volume of 100 µL was used for the analysis.

Site-specific Analysis by Tryptic Mapping LC/MS: The fusion protein was diluted to 4 mg/mL in approximately 100 mM Tris pH 7.5 and 25% acetonitrile, to a final volume of 100 µL. The solution was added to 40 µg trypsin (V511A, Promega, Madison, Wis.) and incubated overnight at 37° C. The digest was quenched by 1:10 dilution with 0.1% trifluoroacetic acid (TFA). The digests were analyzed by LC/MS using a linear gradient of acetonitrile:water with 0.1% TFA from 0% to 50% over 50 min on an Agilent 1100 liquid chromatograph coupled to a Q-T of Micromass spectrometer (Waters, Millford, Mass.). A Zorbax 300-SB column (4.6× 150 mm, Agilent, Palo Alto, Calif.) was used for the separation and mass analysis. The flow from the LC was split ~1:2 prior to introduction into the source of the mass spectrometer.

Peak fraction collection for S100b binding assay: sRAGE-Ig fusion protein samples were concentrated to 4.0 mg/mL using a 10K Amicon Ultra filtration column (Millipore, Bedford, Mass.) and then separated under the reversed-phase conditions for glycan site occupancy as described above. Three fractions representing the site occupancy variants of sRAGE-Ig were collected as triply glycosylated (fraction one, F1), doubly glycosylated (fraction two, F2), and aglycosylated (fraction three, F3). The collected samples were concentrated and exchanged into a stabilizing buffer. Protein concentration of the fraction samples was determined by 280 nm absorbance with a DU 650 spectrophotometer (Beckman Coulter, Fullerton, Calif.) before subjecting the protein to the S100b ELISA binding assay.

S100b binding ELISA: An ELISA assay plate was coated with 100 µL/well of 20 µg/mL S100b protein (Cat. No. 559290, Calbiochem, Gibbstown, N.J.) in coating buffer (Tris buffered saline [TBS], pH8.0, with 5 mM $CaCl_2$) overnight at 4° C. The plate was then washed three times with blocking buffer (TBS pH8.0, with 5 mM $CaCl_2$, 0.05% Tween20, and 1% bovine serum albumin [BSA]), and blocked with the blocking buffer for 1-1.5 hr. sRAGE-Ig fusion samples were prepared in a separate dilution plate, the highest concentration was 10 μg/mL in blocking buffer, with 1:4 serial dilution in blocking buffer down to 2.4 ng/mL. After blocking, the assay plate was washed with the blocking buffer and 100 μL of the samples were transferred from the dilution plate to the assay plate. The assay plate was incubated at room temperature for 2.5 hr. The assay plate was then washed three times with the blocking buffer, with 1 min soaking time between the washes. The horseradish peroxidase conjugated goat anti-human IgG (Cat. No. A2290, Sigma, St. Louis, Mo.) was added to the plate with 100 μL/well at 1:2500 dilution in the blocking buffer. The plate was incubated for 1 hr at room temperature. The assay plate was then washed three times with the blocking buffer again, and 100 μL 3,3',5,5'-tetramethylbenzidine (TMB; Cat. No. 34022, Pierce, Rockford, Ill.) was added to each well and the plate was incubated for 8 minutes at room temperature. 100 μL of 1M $H_2SO_4$ was then added to each well, the plate was shaken and read at 450 nm on a microplate reader.

Results

Figure 3:
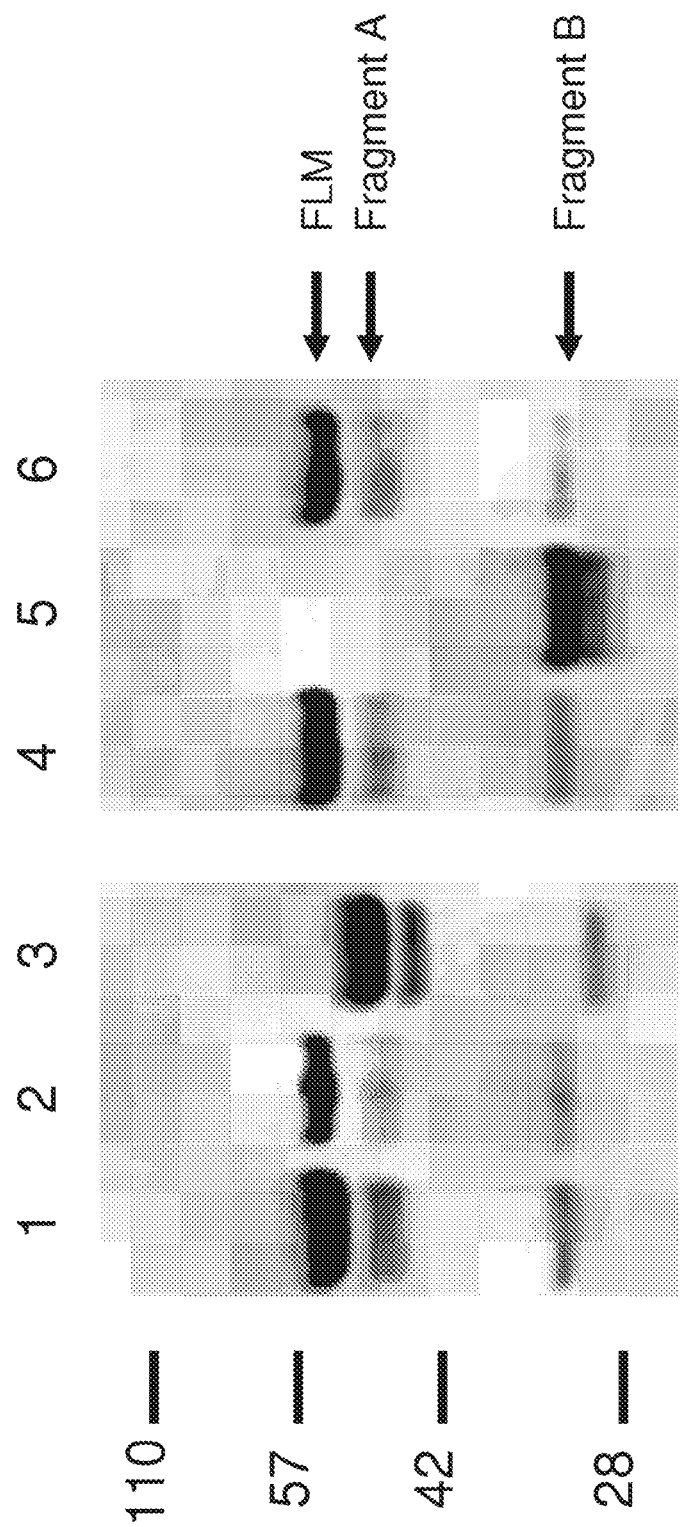
FIG. 3 is an image of a SDS-PAGE analysis of sRAGE-Ig fusion protein demonstrating the effects of digestion with PNGaseF and furin. sRAGE-Ig fusion protein expressed in cells grown in a shake flask culture was purified via mabselect and subjected to digestion with PNGaseF or furin followed by analysis on a reduced 4-12% gradient Bis-Tris gel. Each lane contains 2.7 µg of protein. Molecular weight in Kd is shown on the left. Lanes 1 and 6 contain untreated fusion protein. Lane 2 contains fusion protein incubated with PNGaseF digest buffer alone. Lane 3 contains fusion protein digested with PNGaseF. Lane 4 contains fusion protein incubated with furin digest buffer alone. Lane 5 contains fusion protein digested with furin. FLM=Full Length Monomer.

Expression of sRAGE-Ig fusion protein in host cells: SDS-PAGE analysis of the purified fusion protein from CHO cell conditioned medium in both non-reduced and reduced gels showed the fusion protein migrating as a monomer, which suggests that the dimer is associated via a non-covalent association. It should also be noted that since the purification of the fusion protein employs Protein A, only Fc-containing fragments retaining the portion that binds with protein A are expected to be observed. FIG. 3 depicts a photograph of a reduced SDS-PAGE gel and indicates that the full length monomer (FLM) is the predominant form of the fusion protein which migrates at approximately 55 kDa (lanes 1 and 6). The identities of both fragments A and B (FIG. 3, lanes 1 and 6) were confirmed by mass spectrometry in a separate analysis. Fragment A represents amino acids 55-438 of the FLM (see FIG. 2) migrating at about 46 kDa and Fragment B represents approximately amino acids 199-438 of the FLM migrating at about 30 kDa. Amino acid numbering is based on the sequence shown in FIG. 2 (SEQ ID NO:1). Treatment of the fusion protein with PNGaseF (FIG. 3, lane 3) shows a shift in migration of all three bands, indicating that the FLM plus fragments A and B are N-glycosylated. Complete digestion of the fusion protein with furin (FIG. 3, lane 5) results in the two main bands shown. The upper band in lane 5 co-migrates with the N-glycosylated form of Fragment B seen in lane 6. The lower band in lane 5 co-migrates with the aglycosylated form of Fragment B seen in lane 3. This result, together with the mass spectrometry data which shows that Fragment B contains sequence directly following the furin consensus cleavage site (amino acids 199-438), suggests that Fragment B is produced by furin cleavage of the FLM (or furin cleavage of Fragment A).

Analysis of full length sRAGE-Ig fusion by Size Exclusion Chromatography: The results of SEC analysis of the purified fusion protein from CHO conditioned medium is depicted in FIG. 4 and shows three main peaks: Peak one at 16.94 minutes; peak two at 18.64 minutes; and peak three at 21.63 minutes Using laser light scattering in conjunction with SEC it was determined that the approximate molecular mass associated with peak 1 is about 96 kDa with an error of ±10%. This result is consistent with the assignment of peak 1 as sRAGE-Ig homodimer since the mass that was calculated for the homodimer ranges from about 97-107 kDa depending on glycosylation. Based on this result, it is likely that peak 2 on the SEC profile shown in FIG. 4 represents heterodimer (one full length molecule associated with a furin cleaved Fc fragment) and that peak 3 may represent either an Fc dimer or possibly full length monomer. The component summary for these peaks, which is also shown in FIG. 4, indicates that the sRAGE-Ig fusion protein is predominantly comprised of homodimer (approximately 78%) and heterodimer (approximately 19%) with small amounts of Fc dimer or monomer (approximately 3%) and high molecular mass species (HMMS2)/aggregates (less than 1%).

Glycosylation site occupancy of the sRAGE-Ig fusion protein and fractionation of site occupancy variants: The glycosylation site occupancy profile for FLM of the sRAGE-Ig fusion protein is indicated as sample 1 (S1) in the data depicted in FIG. 5. The profile indicates that sample 1 contains primarily the 3-glycan species (67%) designated sample 1 fraction 1 (S1F1) and 2-glycan species (22%) designated sample 1 fraction 2 (S1F2) with very small amounts of 1-glycan and 0-glycan species (designated sample 1 fraction 3 [S1F3]). The purity of the fractions was confirmed by re-injection using the reversed-phase separation. The identities of both the 3-glycan and 2-glycan peaks for the S1 sample results shown in FIG. 5 were confirmed using LC/MS, described below Analysis of Glycosylation Site Occupancy Variants by LC/MS: Mass spectra for the peaks designated S1F1 and S1F2 as shown in FIG. 5 were generated, and the results are shown in FIG. 6, comprising a top (FIG. 6A) and bottom panel (FIG. 6B). The spectra demonstrate the presence of several species within each sample 1 fraction consistent with glycosylation heterogeneity expected from the three potential N-linked glycan sites present in the molecule. FIG. 6 (top panel, FIG. 6A) shows that the earliest eluting peak, S1F1, is consistent with a species in which all three sites are occupied by an N-linked glycan (52,999-54,105 Da). The predicted molecular weight of the unoccupied (0-glycan site occupancy) species based on the amino acid sequence is 48,594 Da, a difference in mass of about 4000 to 6000 Da. FIG. 6 (bottom panel, FIG. 6B) shows the deconvoluted mass spectra for peak S1F2. The mass spectra show masses consistent with the doubly occupied (2-glycan site occupancy) species (51,785-52,400 Da). In total, the LC/MS analysis indicates a heterogeneous population of species present in S1 with varying amounts of glycosylation. The predominant species, as indicated by the relative UV absorbance, is fully occupied glycoprotein, with lower levels of doubly, and presumably singly, and aglycosylated species. The relative occupancy of the three N-linked sites was assessed using proteolytic mapping, and a more detailed analysis of the types of glycans present at each site was performed as described below.

Size and Charge Profiling analyses of N-glycans released from sRAGE-Ig fusion: A graph depicting the normal phase HPLC chromatogram for the N-linked glycans released from the fusion protein by incubation with PNGaseF is shown in FIG. 7. The peaks were identified by comparison with commercially available glycan standards. The data indicate glycan structures with significant sialylation present, as well as core-fucosylated, biantennary glycans typical of IgG molecules. Also observed are oligomannose structures (Man5, Man6). The relative amounts of each of the glycans are shown in Table 1, with the corresponding proposed structures indicated.

TABLE 1

Relative amount (%) of N-glycans

| Glycan | Structure | Relative % |
|---|---|---|
| G0-GlcNAc-Fuc | 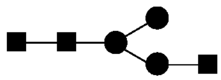 | 1.9 |
| G0-GlcNAc | 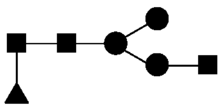 | 2.7 |
| G0-Fuc | 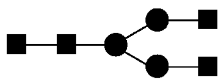 | 1.2 |
| G0 | 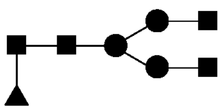 | 34.4 |
| Man5 | 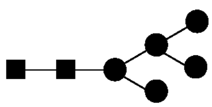 | 9.0 |
| G1-GlcNAc | 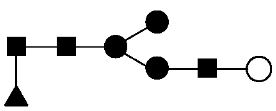 | 0.7 |
| G1 [G1a, G1b] | 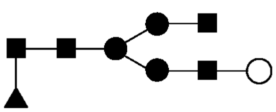 | 16.2 |
| Man6 | 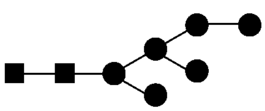 | 2.3 |
| G2 | 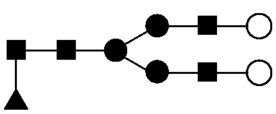 | 8.6 |
| Sialylated | e. g. | 20.2 |
| Total of Unknowns | | 2.6 |

Legend:
■ = N-acetylglucosamine (GlcNAc)
▲ = fucose (Fuc)
● = mannose (Man)
○ = galactose (Gal)
◆ = sialic acid The term "G0" refers to a biantennary structure wherein no terminal sialic acids (NeuAcs) or Gals are present, "G1" refers to a biantennary structure having one Gal and no NeuAcs and "G2" refers to a biantennary structure with two terminal Gals and no NeuAcs.

Analysis of the released glycans by anion exchange chromatography was used to quantify the relative amounts of neutral, singly, and doubly charged species present. The results, summarized in Table 2, agree well with the glycan profiling data, indicating approximately 25% of the species present are sialylated.

TABLE 2

Relative amount of charged glycans

| Neutral Glycans (%) | Mono-sialylated glycans (%) | Di-sialylated glycans (%) |
|---|---|---|
| 74.7 | 20.0 | 5.3 |

The sialylated glycans were not specifically identified in the chromatogram. The peaks labeled "sialylated" in FIG. 7 were identified as such by treatment with sialidase and their corresponding shift in retention time. The type of sialic acid present on the molecule was shown to be N-acetylneuraminic acid using acid hydrolysis, followed by labeling and comparison of retention times on reversed-phase separation to a sialic acids reference panel. Mass spectrometry of the tryptic digest confirmed these assignments.

Tryptic mapping analysis of sRAGE-Ig fusion protein: The UV chromatogram of the tryptic digest of the sRAGE-Ig fusion protein is shown in FIG. 8. The tryptic peptides containing the consensus N-linked sites were identified based on the mass and are labeled in the chromatogram as T1, T10, and T31. The amino acid sequences of these tryptic peptides are: T1 comprises pENITAR (SEQ ID NO:5); T10 comprises VLPNGSFLPAVGIQDEGIFR (SEQ ID NO:6); and T31 comprises EEQYNSTYR (SEQ ID NO:7). T1 contains the first N-linked site in the RAGE domain at Asn2 (N2), T10 contains the second at Asn58 (N58), and T31 contains the Fc domain N-linked glycosylation site which occurs at Asn288 (N288) of the fusion protein (but is otherwise Asn297 of human IgG1). The predicted tryptic peptides containing the glycosylation sites are shown in FIG. 9. The T1 peptide has an N-terminal glutamine (Gln, Q), which undergoes cyclization to form the pyro-glutamic acid (pE) species, indicated as T1pE. The corresponding glcyopeptides for these peptides were detected as well. The inset in FIG. 8 shows an expanded view of the region in which both the T1 and T31 glycopeptides elute. It was not possible to obtain highly accurate quantitative data as to the levels of site occupancy because there were co-eluting peaks. However, an estimate of the levels at each site could be made. That is, the T1 peptide containing the first RAGE glycosylation site at Asn2, is approximately 90% occupied, based on the UV absorbance of the tryptic peptide with and without the glycans present. The glycopeptides of T1 co-elute with glycopeptides from the T31 peptide, making this an estimate. The same is true for the T31 peptide, which contains the IgG glycosylation site at Asn 288. However, very little of the unoccupied peptide was observed, so it can be estimated that this site is at least 95% occupied. Finally, the T10 peptide, which contains the second RAGE glycosylation site at Asn58, is estimated to be about 85% occupied. In total, these measurements agree well with the values obtained by reversed-phase analysis of the intact species as described previously herein.

Mass spectra of the chromatographic peaks of the glycopeptides were generated in order to determine the identity of glycans present at each site. The identities of the glycans were assigned based on the measured masses of the glycopeptides from the mass spectra in combination with the identities determined from the normal phase chromatographic analysis of the released glycans, summarized in Table 1. Together the identities of the glycans present at each of the three glycosylation sites were determined. The data indicate that the majority of the sialylation is present at the Asn2 site, and exists as the G2 glycan with one and two terminal N-acetylneuraminic acids, G2+2NANA and G2+NANA, respectively, along with the G1+NANA glycan. The Asn58 site is comprised mostly of oligomannose structures, with Man5 predominating. There are several minor structures present at this site as well. The Asn288 site shows the presence of mainly G0 and G1 structures, typical of human IgG glycans. A summary of the glycans present at each site, along with an estimate of their relative abundance, is shown in Table 3.

TABLE 3

Identities of the glycans present at each of the three sites in the sRAGE-Ig fusion protein

| Site | Glycan | Relative Abundance |
|---|---|---|
| Asn2 (T1pE) | G2 + 2NANA | ++ |
|  | G2 + NANA | ++ |
|  | G1 + NANA | ++ |
| Asn58 (T10) | Man5 | ++ |
|  | Man6 | + |
|  | Man4 | + |
| Asn288 (T31) | G0 | +++ |
|  | G1 | ++ | peaks for binding analysis. The 0-glycan species is consistent with the theoretical mass of the sRAGE-Ig fusion with pyroglutamic acid (pE) at the N-terminus, and a mixture of variants with or without C-terminal lysine, typical of IgG heavy chain molecules which demonstrate hetergeneous C-termini due to partial proteolytic processing (i.e., lysine clipping) during expression.

Determining the binding of site occupancy variants to S100b. S100b is a known RAGE ligand whose interaction with RAGE has been mapped to the VC1 domain. Extracellular binding of S100b to RAGE stimulates an increase in RAGE levels which results in an increasing cellular response and establishment of chronic inflammation and disease. Mixtures and fractions of site occupancy variants isolated from the sRAGE-Ig fusion protein as described above, were tested therefore for their ability to bind to S100b and the results are shown in Table 4. Results are reported as both IC50 values and relative binding to S100b (%) compared to the S1 control (untreated sRAGE-Ig produced by CHO cells grown without tunicamycin).

TABLE 4

S100b binding ELISA

| Sample | Description | Concentration mg/mL | IC50 (μg/mL) | IC50 (nM) | Relative binding compared to control |
|---|---|---|---|---|---|
| S1 = control (untreated) | 3-Glycan = 67% 2-Glycan = 22% | 0.375 | 0.18 | 1.8 | 100% |
| S1F1 | 3-Glycan only | 0.612 | 0.39 | 3.9 | 46% |
| S1F2 | 2-Glycan only | 0.415 | 0.104 | 1.04 | 173% |
| S2 = TMYCN (treated with tunicamycin) | 3-Glycan = 42% 2-Glycan = 16% 0-Glycan = 31% | 0.357 | 0.061 | 0.61 | 295% |
| S2F1 | 3-Glycan only | 0.366 | 0.89 | 8.9 | 20% |
| S2F2 | 2-Glycan only | 0.182 | 0.1 | 1 | 180% |
| S2F3 | 0-Glycan only | 0.301 | 0.034 | 0.34 | 529% |

Tunicamycin Treatment

The antibiotic tunicamycin is a glycosylation inhibitor that inhibits the glycosyltransferase that transfers phospho-N-acetylglucosamine (P-GlcNAc) from uridine diphosphate (UDP)-GlcNAc to form dolichol phosphate (Dol-P)-GlcNAc. Tunicamycin was used herein to demonstrate that inhibition of glycosylation can reduce glycan site occupancy of a protein and, more preferably, can affect the binding characteristics of the protein in binding with a cognate ligand of the protein.

The site occupancy of tunicamycin treated samples. The glycosylation site occupancy profile for the full length sRAGE-Ig fusion protein expressed from CHO cells treated with tunicamycin is shown as sample 2 (S2) in FIG. 10. The profile indicates the sample contains primarily 3-glycan species (42%), 2-glycan species (16%) and 0-glycan species (31%) with no 1-glycan species detected. The identity of the 3-glycan, 2-glycan and 0-glycan peaks for the S2 sample in FIG. 10 were confirmed using mass spectrometry (FIG. 11) prior to fractionation and collection of the S2 fraction 1 (S2F1) (3-glycan), S2F2 (2-glycan) and S2F3 (0-glycan)

When the sRAGE-Ig fusion protein was expressed in CHO cells treated with tunicamycin (sample S2) the glycan occupancy profile shifts from a mixture of 67% 3-glycan+22% 2-glycan (untreated/control sample S1) to 42% 3-glycan+ 16% 2-glycan+31% 0-glycan (treated with tunicamycin/ sample S2). The relative binding of sample S2 to S100b (295%) is approximately three fold that of sample S1(100%) which suggests that the lower glycan occupancy of the mixture leads to better binding of sRAGE-Ig to S100b. Additional binding studies with isolated glycan fractions confirmed this finding. The 2-glycan fraction (S1F2) isolated from the S1 control showed improved binding to S100b (173%) compared to the 3-glycan fraction (46%) (S1F1) also isolated from the S1 control. The highest binding to S100b was observed with the 0-glycan fraction (S2F3) isolated from the tunicamycin treated sample S2. The aglycosylated variant (S2F3) showed a ten-fold increase (529%) in binding to S100b compared to the fully occupied 3-glycan version (46%) for sample S1F1 and a five-fold increase compared to the unfractionated untreated S1 control (100%).

Discussion

In this study a human sRAGE-Ig fusion protein was expressed and characterized. Further, the impact of glycosylation on binding of this protein to the RAGE ligand S100b was examined. Although fusion proteins have traditionally been generated in order to improve the serum half life of the fusion partner, little is known about how linking a portion of RAGE, or a portion of sRAGE to immunoglobulin domains or how dimerization may impact folding and glycosylation of sRAGE or its ability to engage ligands.

The data disclosed herein suggest that sRAGE-Ig fusion protein expressed in CHO cells exists predominantly as a non-covalent homodimer with the remaining protein existing as a heterodimer formed by furin cleavage of the homodimer with loss of a single RAGE V-like domain. Since there is a furin consensus sequence in the C1 domain of RAGE it is not clear why the homodimer population is not cleaved more efficiently. Without wishing to be bound by any particular theory, the incomplete cleavage of FLM by furin leading to a heterogeneous population of cleaved and uncleaved dimers is likely due to fact that CHO cells, and mammalian cells in general, produce very low amounts of endogenous furin (Ayoubi et al., 1996, Molecular Biology Reports. 23:87-95).

Also intriguing is what is the biological purpose of a furin cleavage site in the RAGE molecule and whether furin cleavage has any functional significance to the biological function of the endogenous RAGE molecule. Cleavage by furin has been shown to release soluble forms of the apolipoprotein E receptor 2 (ApoER2) (Koch et al., 2002, EMBO J. 21:5996-6004) and the low density lipoprotein receptor-related protein (LRP) (Herz et al., 1990, EMBO J. 9:1769-1776), Therefore, and without wishing to be bound by any particular theory, furin may be involved in producing a soluble RAGE receptor fragment in vivo that can be used either to modulate or inhibit ligands interacting with their cellular targets or to control RAGE signaling. Although novel splice variants of human RAGE mRNA have been shown to be one mechanism responsible for producing soluble forms of the RAGE receptor (Yonekura et al., 2003, Biochem. J. 370:1097-1109), less is known about proteolytic processes that could produce endogenous soluble RAGE. Interestingly, in mice, soluble RAGE is produced by carboxy-terminal truncation in contrast to the alternative splicing mechanism reported in humans (Hanaford et al., 2004, J. Biol. Chem. 279:50019-50024). Thus, without wishing to be bound by any particular theory, furin cleavage observed in the sRAGE-Ig fusion protein may be indicative of endogenous cleavage of RAGE and may play a role in the biological function of the molecule in vivo.

Native RAGE is N-glycosylated at two potential sites in the V-like domain at N2 and N58. A number of studies have shown that glycosylation of RAGE can impact its affinity and/or specificity for RAGE ligands and that binding may vary depending on the ligand in question. Wilton et al (2006, Protein Expression Purif. 47:25-35) reported that soluble RAGE expressed in bacteria (monomeric, aglycosylated) binds to several RAGE ligands including advanced glycation end products (AGE)-BSA, immunoglobulin light chain amyloid fibrils and glycosaminoglycans. However, the *E. coli* derived sRAGE, which was not a fusion protein, did not bind the AGE carboxymethyl lysine (CML)-BSA. Dattilo et al. (2007, Biochemistry 46:6957-6970) also demonstrated that bacterially expressed soluble RAGE binds to AGE-BSA in addition to binding S100b and amphoterin. In contrast, Srikrishna et al. (2002, J. Neurochem. 80:998-1008) reported that the native full-length glycosylated RAGE receptor isolated from bovine lung showed a significant reduction in binding to amphoterin when the receptor was deglycosylated. Osawa et al. (2007, Biochimica et Biophysica Acta 1770: 1468-1474) also showed that deglycosylation mutants of soluble RAGE expressed in mammalian cells showed a reduction in binding to AGE compared to the glycosylated wildtype. Thus, it was not clear what the effect of glycosylation, or lack thereof, was on RAGE, or sRAGE, ligand binding. Further, none of the previous studies had examined the effects of glycosylation on sRAGE binding to its ligands where the sRAGE was fused to an Ig domain.

The data disclosed herein demonstrate for the first time that that linking an immunoglobulin region to a sRAGE does not appear to interfere with glycosylation of the V-like domain of RAGE since the expressed fusion protein shows both N-linked sites at Asn2 and Asn58 approximately 90% and 85% occupied, respectively, in the fusion protein. Without wishing to be bound by any particular theory, it may be that since this fusion protein exists as a dimer, dimerization of sRAGE may have an impact on its affinity for ligands. That dimerization plays a role in ligand binding is suggested by the studies of Ostendorp et al. (2007, EMBO J. 26:3868-3878) who have shown that tetrameric S100b binds optimally to dimeric sRAGE. The present studies demonstrate that the sRAGE-Ig fusion protein with N-glycosylation at all three sites (3-glycan species)—two in the V-like domain and one in the Ig region, shows poor binding to S100b compared to the aglycosylated forms (e.g., a form having no more than 2 N-linked glycosylation sites occupied). Binding of the sRAGE-Ig fusion protein to S100b increased when 1 N-linked site in the protein is not occupied (2-glycan species), and shows the highest binding to S100b when all three sites in the protein are unoccupied (0-glycan species). Since it cannot be differentiated between an occupied N-linked site in the RAGE V-like domain and an occupied site in the Ig region, the 2-glycan species could represent both sites occupied in the RAGE V-like domain (N2 and N58) with no glycan at N288 or the 2-glycan species may represent glycan occupancy at N2 and N288 or at N58 and N288. However, since the tryptic mapping data indicates that the N-glycan site in the Ig region (Asn288) is the most highly occupied of the three (95% compared to 90% for Asn2 and 85% for Asn58), the data suggest that at least two thirds of the 2-glycan species will contain an occupied site at Asn288 and therefore two thirds of the 2-glycan species should only have a single N-linked site occupied in the RAGE V-like domain, either Asn2 or Asn58. The data disclosed herein shows increased binding of the 2-glycan species of the sRAGE-Ig fusion protein to S100b compared to the 3-glycan species, therefore, without wishing to be bound by any particular theory, the increased binding may be the result of a loss of glycosylation in the RAGE V-like domain. This trend is confirmed by the data disclosed herein which show the highest binding of the 0-glycan species of the sRAGE-Ig fusion protein to S100b compared to 2-glycan or 3-glycan species. These data further indicate that the increased ligand binding is the result of decreased glycosylation in the RAGE V-like domain, which is most pronounced by the 0-glycan species which completely lacks glycosylation in the RAGE V-like domain.

In summary, the data disclosed herein demonstrate, for the first time, that the aglycosylated variant of the sRAGE-Ig fusion protein provides optimum binding to the RAGE ligand S100b. Since the binding site on RAGE for S100b has been identified as the VC1 domain (Datillo et al., 2007, Biochemistry 46:6957-6970), and without wishing to be bound by any particular theory, these data suggest that N-glycosylation at positions Asn2 and Asn58 in soluble RAGE may physically inhibit S100b binding, or may alter recognition of the ligand binding site. In addition to studying the binding of the RAGE ligand S100b, the binding of the sRAGE-Ig fusion protein and its glycosylation variants to the A-beta peptide was examined and found a similar result was found as demonstrated below.

Example 2

Increased Abeta Binding by RAGE Comprising Decreased Glycan Site Occupancy

As described previously elsewhere herein, sRAGE-Ig was expressed in untreated CHO cells (control; Sample 1=S1) and in tunicamycin (TMYCN) treaded CHO cells (Sample 2=S2). The samples were then fractionated as described previously to obtain fractions comprising fusion protein having the following glycan-site occupancy: Sample 1-Fraction 1 (S1F1) =untreated cells, 3-glycan occupancy; Sample 1-Fraction 2 (S1F2)=untreated cells, 2-glycan occupancy; Sample 2-Fraction 1 (S2F1)=TMYCN treated cells, 3-glycan occupancy; Sample 2-Fraction 2 (S2F2)=TMCYN treated cells, 2-glycan occupancy; Sample 2-Fraction 3 (S2F3)=TMYCN treated cells, 0-glycan occupancy. The binding of each fraction to Abeta was compared to the binding of S1 (control, untreated cells) and the results are summarized in Table 5 below.

Assay for Aβ peptide binding activities: Briefly, two human Aβ peptides were tested: Aβ1-40 (Catalogue# A-1153-2, Rpeptide), and Aβ1-28 (Catalogue#24232, AnaSpec). The plates were coated by 20 μg/mL peptide in 1% $NH_4OH$ overnight at 4° C. The plate was then washed with blocking buffer (TBS pH8.0, 0.05% Tween20, and 1% BSA) and blocked for 1 hr at room temperature. All the other steps were performed essentially as described previously herein for S100b binding assay, supra.

binding to Abeta was observed with the 0-glycan fraction (S2F3) isolated from the tunicamycin treated sample S2. The aglycosylated variant (S2F3) showed a six-fold increase (295%) in binding to Abeta compared to the fully occupied 3-glycan version (49%) for sample S2F1 and a three-fold increase compared to the unfractionated untreated S1 control (100%).

In sum, decreased glycan site occupancy mediated increased binding of sRAGE-Ig fusion protein to Abeta. Therefore, the data disclosed herein demonstrate that control of glycosylation can be used to improve the binding characteristics of a protein to its ligands.

Example 3

Control of Glycosylation Using 2-deoxy-D-glucose: Decreased Glycan Site Occupancy Affects RAGE Ligand Binding The RAGE-Fc fusion protein used in this study contains the ligand binding site of RAGE, comprising the V-like and C-like C1 domains of human RAGE linked to a portion of the $C_H2$ domain and the $C_H3$ domain of a human IgG1 molecule. The fusion protein comprises three N-linked glycosylation sites, two in the RAGE domain, at N2 and N58, and one in the Fc region (at amino acid residue number 288 of the fusion peptide), which when expressed in CHO cells are approximately 70% fully occupied. As disclosed previously elsewhere herein, tunicamycin was used in cell culture to express the fusion protein and produce site occupancy variants. The glycosylation variants were isolated and the impact of glycan

TABLE 5

Effect of glycan-site occupancy on sRAGE-Ig binding to Abeta

| Sample | Description | Concentration mg/mL | IC50 (nM) | Relative binding compared to control |
|---|---|---|---|---|
| S1 = Control (Untreated cells) | 3-glycan ≈ 67% 2-glycan ≈ 22% | 0.375 | 1.24 | 100% |
| S1F1 | 3-glycan | 0.612 | 1.21 | 102% |
| S1F2 | 2-glycan | 0.415 | 0.73 | 170% |
| S2 = TMYCN (Cells treated with tunicamycin) | 3-glycan ≈ 42% 2-glycan ≈ 16% 0-glycan ≈ 31% | 0.357 | 0.82 | 151% |
| S2F1 | 3-glycan | 0.366 | 2.51 | 49% |
| S2F2 | 2-glycan | 0.182 | 0.52 | 238% |
| S2F3 | 0-glycan | 0.301 | 0.42 | 295% |

As disclosed previously herein with respect to fusion protein binding with S100b, when the sRAGE-Ig fusion protein was expressed in CHO cells treated with tunicamycin (sample S2) the glycan occupancy profile shifted from a mixture comprising approximately 67% 3-glycan+22% 2-glycan (untreated/control sample S1) to a mixture comprising about 42% 3-glycan+16% 2-glycan+31% 0-glycan (treated with tunicamycin/sample S2).

The relative binding of sample S2 to Abeta (151%) is approximately one and one-half times greater than that of sample S1(100%), suggesting that the lower glycan occupancy of the S2 mixture leads to better binding of sRAGE-Ig to Abeta compared to the more glycosylated S1 sample. Additional binding studies with isolated glycan fractions confirmed this finding. Similarly to the results disclosed previously with respect to S100b binding, the 2-glycan fraction (S1F2) isolated from the S1 control showed improved binding to S100b (170%) compared to the 3-glycan fraction (102%) (S1F1) also isolated from the S1 control. The highest occupancy on binding to RAGE ligands was determined. As disclosed previously, the aglycosylated 0-glycan site occupancy variant showed a ten fold increase in binding to S100b (529%) compared to the fully occupied 3-glycan version (46%), whereas the doubly occupied 2-glycan variant showed an intermediate binding between the two (180%). Similarly, with regard to binding to Abeta, the aglycosylated 0-glycan variant showed a six-fold increase (295% compared with unfractionated control glycan mixture) in binding to Abeta relative to the fully occupied 3-glycan version (49% compared with unfractionated control mixture) and the 2-glycan site occupancy variant (238% relative to unfractionated mixture) showed an intermediate increase in binding (238% compared with unfractionated control mixture) very similar to that of the 0-glycan variant. In sum, the data disclosed elsewhere herein using tunicamycin as a glycan site occupancy inhibitor demonstrated for the first time that decreased site occupancy increased affinity for RAGE binding to its ligands, more specifically, that RAGE-Ig fusion protein binding affinity could be controlled by inhibiting glycan site occupancy. Thus, these data demonstrate that the glycosylation pattern of recombinant proteins can be manipulated intracellularly to improve binding of the protein to its ligand. These data suggest it would be useful to develop a bioprocess using N-glycan site occupancy inhibitors for the manufacture of a molecule with increased binding activity.

A less costly and non-toxic N-linked glycan site occupancy inhibitor, 2-deoxy-D-glucose, was used to develop such a novel bioprocess. 2-deoxy-D-glucose functions as a glycolysis antagonist by competitively inhibiting hexokinase and glucose phosphoisomerase and competes with mannose by incorporating into dolichol-pyrophosphate linked oligosaccharides during N-linked glycosylation. The effect of using 2-deoxy-D-glucose on cell culture expressing the sRAGE-Fc fusion protein described previously using a controlled fed batch bioreactor process was assessed. The data disclosed herein demonstrate the impact of this inhibitor on N-linked site occupancy and on subsequent binding activity of the fusion protein to the S100b ligand. The results disclosed herein demonstrate increased production of the aglycosylated variant of the fusion protein relative to the more glycosylated variants with the use of the inhibitor. More importantly, the data disclosed herein demonstrate that fusion protein producing using a 2-deoxy-D-glucose containing bioprocess demonstrated an increased affinity for the S100b ligand.

Therefore, the data disclosed herein demonstrate that 2-deoxy-D-glucose can be used effectively in a bioreactor process to control the N-linked glycan site occupancy of recombinant molecules expressed in mammalian cells. As such, this inhibitor can be used during a manufacturing process to manipulate preferred features of a molecule, such as optimum target/ligand/tissue binding activity, solubility, half life/clearance from serum, among others.

Materials and Methods

Cell Line Maintenance and Bioreactor Inoculum Trains

CHO cells expressing RAGE-Fc fusion protein were maintained and expanded as suspension cultures in 125, 250, 500, 1000, or 2000 ml vented shaker flasks (Corning) agitated on a shaker platform incubator (Kuhner, Model No. ISF-1-W) at 140 rpm, 1 inch throw, and 36.5° C.

0.5 L Bioreactor Runs—DASGIP Cell Cultivation System

The DASGIP Cellferm-pro cultivation system (Jülich, Germany), a modular system for the parallel cultivation of mammalian cells with a maximum of eight pH and $O_2$ controlled setups, was used for 0.5 L bioreactor runs according to manufacturer's instructions.

1 L Bioreactor System

For 1 L bioreactor runs, the Applikon cultivation system of 1 L working volume stirred glass vessels (Cat No. V3MB010012, Applikon Inc., Foster City, Calif.) with submerged $O_2$/$CO_2$ gassing and constant air overlay into headspace controlled by the Applikon 1030 ADI controller coupled with Applikon Flow Console and P100 ADI 1032 Stirrer Controller.

For substrate dosing, Watson-Marlow 101U/R pumps (Cat No. 010.4202.00A, Watson-Marlow Bredel Inc., Wilmington, Mass.) were used.

Control Medium

Commercially available production medium, CD CHO medium, is protein free, chemically defined media for CHO growth and monoclonal antibody production (Cat No. 10743.029, Invitrogen, Carlsbad, Calif.). Inoculum train medium was supplemented with 250 μl (25 μM) of 100 mM L-methionine sulfoximine (Cat No. GSS-1015-F Millipore). Production medium was preloaded with additional amino acids 0.77 g/L isoleucine, 1.08 g/L leucine, 0.91 g/L tyrosine 2 Na, 0.38 g/L valine, 0.405 g/L cysteine, and 0.07 gL tryptophan.

Experimental Media

Commercially available CD Opti-CHO medium is a protein free, chemically defined medium (Ref No. 12681-01, Invitrogen). Inoculum train medium was supplemented with 250 μl (25 μM) of 100 mM L-methionine sulfoximine (MSX) (Cat No. GSS-1015-F, Millipore, Bedford, Mass.).

Lipid-free Opti-CHO is a protein free, chemically defined commercially available medium (Invitrogen, Sku. ME080016). Inoculum train medium was supplemented with 250 μl (25 μM) of 100 mM L-methionine sulfoximine (MSX) (Millipore, Cat No. GSS-1015-F).

Ex-Cell 325 medium is protein free commercially available medium (Cat No. 14340C, Sigma). Inoculum train medium was supplemented with 250 μl (25 μM) of 100 mM L-methionine sulfoximine (Millipore, Cat No. GSS-1015-F)

Nutrient Feeds and Supplements CDFv6.2 Nutrient Feed Solution, a proprietary feed, is a chemically defined powder manufactured by Invitrogen (Carlsbad, Calif.) in a powder formulation. The CDFv6.2 Lipid-Free Nutrient Feed solution was formulated without fatty acid precursor subgroups. Reconstitution of these feeds involved dissolving the feed in WFI and adjusting pH to 7.0.

Glucose Feed Solution: The feed was 300 g/L (30%) glucose (Cat No. G-8920, Sigma) solution.

2-deoxy-D-glucose treatment: 2-deoxy-D-glucose (Cat No. D8375-100G or Cat No. D3179, Sigma) was dissolved in approximately 40 ml water for injection (WFI) and bolus injected based on the dosing strategy for each reactor as seen in Table 6 below.

TABLE 6

2-Deoxy-D-Glucose Dosing Strategies

| Bioreactor | Run # | Medium | Feed | Dose Strategy |
|---|---|---|---|---|
| 0.5L DASGIP | R39 | CD CHO | CDFv6.2 | No addition |
| | R53 | CD CHO | CDFv6.2 | 2-deoxy-D-glucose (1 g/L at day 9; 11) |
| | R57 | CD CHO | CDFv6.2 | 2-deoxy-D-glucose (0.5 g/L at day 9, 11) |
| | R66 | CD OptiCHO lipid-free | CDFv6.2 lipid-free | 2-deoxy-D-glucose (1 g/L at day 9) |
| 1L Applikon | R79 | Ex Cell 325 PF CHO | CDFv6.2 | 2-deoxy-D-glucose (1 g/L at day 7; 9) |
| | R80 | CD CHO | CDFv6.2 | 2-deoxy-D-glucose (1 g/L at day 7; 9) |

ViCell Cell Numerator: An automated cell viability analyzer manufactured by Beckman Coulter (Model No. ViCell XR) performs trypan blue exclusion method through video imaging of the flow through cell.

Cedex Cell Numerator: An automated cell counter (Model No. CEDEX AS20, innovatis AG, Bielefeld, Germany) that detects and differentiates viable and dead cells by trypan blue exclusion method through image analysis of microscopic images of the Cedex Flow Cell, designed to equal a hemacytometer.

NOVA BioProfile 400 and Flex Analyzers: Automated metabolite analyzers for mammalian cell suspension (Model No. BioProfile 400 and Model No. BioProfile Flex, NOVA Biomedical, Waltham, Mass.) were used. The BioProfile 400 analyzes cell suspension for nutrient/metabolites (glutamine, glucose, lactate, glutamate), acid/base status (pH, PCO2, PO2), electrolytes (sodium, potassium), and calculated parameters (Osmolality, Air and CO2 saturation, $HCO_3$) via specific enzymatic or non-enzymatic sensors. The BioProfile Flex consolidated multiple analyzers in a single modular instrument, which analyzes cell suspension in Module 1: Gluc, Lac, Gln, Glu, NH4+, pH, $PCO_2$, $PO_2$, Na+, K+, Ca++, by Electrochemistry; Module 2: Osmolality, by Freezing Point Depression; and Module 3: Cell Density/Cell Viability, by Digital Imaging.

Osmometer: An Advanced Micro-osmometer (Model No. 3320), an automated, single-sample osmometer designed to process 20-μl sample, was used (Advanced Instruments, Inc., Norwood, Mass.). The Model 3320 employs the freezing-point depression method via the sample is cooled before the sample is analyzed for osmolality.

Agilent HPLC Analyses: Unpurified cell culture broth samples were analyzed for sRAGE-Ig Fc fusion protein production titers using the antibody affinity method protocol POROS6B.M (Lincoln PGM SOP "Protein A HPLC, HB-0004-01") and Agilent 1100 Series instruments (Model No. G1316A, SN DE11122116 and Model No. G1329A, SN DE91603800). The protocol involves the following chromatographic conditions: Equilibrium Mobile Phase: 1×PBS (Invitrogen without $MgCl_2$ and $CaCl_2$); Elution Mobile Phase: 12 mM HCl, 150 ml NaCl, pH 2.25; Wash Buffer: WFI water; Cleaning Buffers: 6 M guanidine and 70% ethanol; Column: Applied BioSystems Protein A Immuno Detection Sensor Cartridge (Cat. No. 2-1001-00, SN 6940, 7318); Injection volume: 20 μL; and Detector: Ultraviolet Absorbance λ=280 nm.

Results and Discussion

Tunicamycin Treatment—Determining the Binding of Site Occupancy Variants to S100b The antibiotic tunicamycin is a glycosylation inhibitor that inhibits the glycosyltransferase that transfers phospho-N-acetylglucosamine (P-GlcNAc) from uridine diphosphate (UDP)-GlcNAc to form dolichol phosphate (Dol-P)-GlcNAc. The data disclosed previously elsewhere herein demonstrate that tunicamycin can be used to decrease glycan site occupancy of a protein and, more preferably, to affect the binding of the protein to its ligand. However, tunicamycin is not a desirable inhibitor for a bioreactor process since toxic and costly. Therefore, another glycan site occupancy inhibitor, 2-deoxy-D-glucose, was used to control glycan site occupancy in the RAGE-Ig fusion protein assay.

As pointed out previously elsewhere herein, S100b is a known RAGE ligand whose interaction with RAGE has been mapped to the ligand binding site within the V/C1 domain. Mixtures and fractions of site occupancy variants isolated from the tunicamycin treated RAGE-Fc fusion protein as described above, were tested for their ability to bind to S100b and the results are shown in Table 5, supra. Results are reported as both IC50 values and relative binding to S100b (%) compared to the S1 control (unfractioned RAGE-Fc produced by untreated cells). When the RAGE-Fc fusion protein was expressed in CHO cells treated with tunicamycin (sample S2) the glycan occupancy profile shifted from a mixture of about 67% 3-glycan+22% 2-glycan (untreated/control sample S1) to a mix comprising about 42% 3-glycan+16% 2-glycan+31% 0-glycan (treated with tunicamycin/sample S2). The relative binding of sample S2 to S100b (295%) is approximately three fold that of sample S1(100%) which suggests that the lower glycan occupancy of the mixture leads to better binding of RAGE-Fc to S100b. Additional binding studies with isolated glycan fractions confirmed this finding. The 2-glycan fraction (S1F2) isolated from the S1 control showed improved binding to S100b (173%) compared to the 3-glycan fraction (46%) (S1F1) also isolated from the S1 control. The highest binding to S100b was observed with the 0-glycan fraction (S2F3) isolated from the tunicamycin treated sample S2. The aglycosylated variant (S2F3) showed a ten-fold increase (529%) in binding to S100b compared to the fully occupied 3-glycan version (46%) for sample S1F1 and a five-fold increase compared to the untreated S1 control (100%).

2-Deoxy-D-glucose Treatment—Determining the Binding of Site Occupancy Variants to S100b Treatment of cultures with 2-deoxy-d-glucose has been reported to interfere with specific steps in the N-linked glycosylation pathway or function as a substrate antagonist. 2-Deoxy-D-glucose functions as a glycolysis antagonist by competitively inhibiting hexokinase and glucose phospho-isomerase. In addition, it has been reported that this sugar analogue competes with mannose by incorporating into dolichol-pyrophosphate linked oligosaccharides during N-linked glycosylation.

Reactor run 39 (R39) sampled on day 10 as listed in Table 6 represents the baseline glycan site occupancy profile and S100b binding activity of the RAGE-Fc fusion protein, purified from conditioned medium harvested on days 10, using the CHO control process in a 0.5 L DASGIP bioreactor. The CHO control process includes a temperature shift from 34° C. to 31° C. on day 7. The results as shown in Table 7 are essentially the same on day 10 and day 12 for this reactor. The RAGE-Fc fusion protein is predominantly hyperglycosylated in this control process with the majority of the molecule being in the 3-glycan (about 46%) and 2 glycan (about 28%) form. These samples show the least amount of binding to S100b.

TABLE 7

Glycan occupancy and S100b binding activity of the RAGE-Fc fusion protein purified from bioreactors dosed with the glycosylation inhibitor 2-deoxy-D-glucose.

| Reactor/Sample ID | | Glycan Occupancy Assay (%) | | | | Relative binding compared to control |
|---|---|---|---|---|---|---|
| | | 3-Glycan | 2-Glycan | 1-Glycan | 0-Glycan | |
| R39 | Day 10 | 46.7 | 29.6 | 5.0 | 0.4 | NA |
| | Day 12 | 45.8 | 25.4 | 4.1 | 0.3 | 100 |
| R53 | Day 10 | 34.8 | 35.8 | 10.7 | 2.4 | 296 |
| | Day 12 | 23.4 | 27.2 | 12.5 | 17.8 | 1521 |
| R66 | Day 12 | 32.9 | 16.7 | 15.9 | 12.2 | 3246 |
| | Day 14 | 28.1 | 17.0 | 19.9 | 13.6 | 3523 |
| R79 | Day 12 | 68.0 | 25.2 | 4.9 | 0.8 | 527 |
| | Day 13 | 42.4 | 33.6 | 13.6 | 7.3 | 2957 |
| R80 | Day 12 | 21.7 | 25.8 | 18.5 | 31.8 | 1632 |
| | Day 14 | 12.2 | 18.0 | 16.2 | 53.2 | 8077 |

Reactor R53 the results of which are set forth in Table 7, is an identical reactor to R39 run with the same process but with the addition of two 1 mg/mL (6 mM based on reactor volume) bolus injections of 2-deoxy-D-glucose administered on days 9 and 11 of the process. The glycan site occupancy profile and S100b binding activity of the RAGE-Fc fusion protein purified from conditioned medium harvested on days 10 and 12 of this reactor are also shown in Table 2 and FIG. 1. The data disclosed herein demonstrate an increase of 100-1521% in binding activity on day 12 in this reactor compared to the binding activity of the baseline bioreactor R39. This increase in binding activity correlates with an increase in the aglycosylated species together with a decrease in the higher glycosylated forms.

The correlation between binding activity and site occupancy was observed in different medium formulations and dosing strategies. Commercially available CHO media (i.e., Ex Cell 325 PF CHO and OptiCHO) are formulated with proprietary concentrations of medium components such as amino acids, glucose, vitamins, salts, and trace elements. To demonstrate the influence of medium in conjunction with 2-deoxy-D-glucose addition on glycosylation distribution patterns in a bioreactor, CHO cells expressing the RAGE-Fc fusion protein were directly adapted into CD OptiCHO (Invitrogen) media and Ex Cell 325 PF CHO (Sigma). CD OptiCHO, a chemically defined, a medium free of animal components and protein, was formulated into different batches: catalog formulation and custom formulation without lipids to correspond to lipid-free formulation of the Invitrogen CD CHO catalog medium. Bioreactor R66 utilized the 1 L CHO Applikon control process minus the amino acid preload, CD OptiCHO medium without lipid precursors and CDFv6.2 nutrient feed without fatty acid precursor subgroups. A single 1 mg/ml (6 mM based on 1 L reactor volume) bolus injection of 2-deoxy-d-glucose was administered to the bioreactor on day 9. Culture medium samples were harvested on days 12 and 14, and the conditioned medium samples were purified and assayed for glycan site occupancy and S100b binding activity with the results tabulated in Table 7 and FIG. 12. The results indicate a decrease in fully glycosylated species and an increase in aglycosylated species relative to the baseline "control" bioreactor, R39, at harvest (3-glycan: 45.8 for R39 day 12 vs. 32.9% for R66 day 12; 0-glycan: 0.3 for R39 day 12 vs. 12.2% for R66 day 12). This shift in glycoform distribution correlates with a 32 fold increase (100% baseline compared with day 10 for R39 vs. 3246% for R66 at day 12) in S100b binding activity when compared to the day 12 baseline bioreactor, R39, sample. In addition, the results shown in Table 6 and FIG. 12 suggest improvement in glycan occupancy profiles and S100b binding activity with continued culturing.

Ex-Cell 325 PF CHO medium, a protein-free medium formulated without glutamine, was investigated in a 1 L Applikon bioreactor run, R79, which utilized the CHO control process minus the 6 amino acid medium preload. Two 1 mg/mL (6 mM based on 1 L bioreactor volume) bolus injections of 2-deoxy-d-glucose were administered to the bioreactor on days 7 and 9. Culture medium samples were harvested on days 12 and 14, and the conditioned medium was purified and assayed for glycan site occupancy and S100b binding activity. The data for these bioreactor conditions are shown as R79 in Table 7 and FIG. 12. The data disclosed herein indicate an increase in fully glycosylated species (3-glycan: 68.0% for R79 day 12 vs. 45.8% for R39 day 12) and an increase in the 0-glycan form (0.8% R79 day 12 vs. 0.3% R39 day 12). This change in glycoform distribution correlates with a five-fold increase (100% of baseline for R39 compared with 527% relative to baseline for R79, with baseline being the binding of control R39 on day 10) in S100b binding activity on day 12 compared to the baseline bioreactor R39 (day 10). In addition, the data disclosed herein, e.g., Table 7 and FIG. 12, suggest improvement in glycan occupancy profiles and S100b binding activity with continued culturing.

A similar increase in aglycosylated variants and S100b binding was obtained when implementing the 2-deoxy-d-glucose bolus doses using CD CHO medium. Reactor R80 in Table 7 is identical to reactor R79 run with the same process but using CD-CHO instead of the Ex Cell 325 PF CHO medium. The data for this bioreactor are shown as R80 in Table 7 and FIG. 12. The data disclosed herein indicate that similar to R79, treatment with 2-deoxy-D-glucose produced an overall decrease in fully glycosylated species and also mediated an increase in the 0-glycan forms. Notably, the fully glycosylated species decreased (45.7-21.7%) and aglycosylated increased (0.3-31.8%) relative to the baseline bioreactor (R39 on day 10). The shift in glycan occupancy dramatically increased the S100b binding activity (100-1632%) for conditioned media obtained on day 12 of each bioreactor run. The S100b binding activity from the day 14 sample of the R80 reactor was the highest obtained and was significantly higher than binding activity associated with samples from the baseline reactor R39— surprisingly, bioreactor run R80 was about 8077% or approximately eighty-fold greater than the control bioreactor R39 on day 10.

In summary, 2-deoxy-D-glucose supplementation produced an increase in the RAGE-Ig aglycosylated (0-glycan site occupancy) variant which also showed improved binding to the S100b ligand. The surprising increase in aglycosylated variants with improved binding affinity was the result of a shift in the glycosylation distribution pattern following the 2-deoxy-D-glucose dosing strategy. Using the CHO control process in combination with two 1 g/L doses of 2-deoxy-D-glucose an increase was demonstrated in bioreactors in the production of aglycosylated variant of the RAGE-Ig fusion protein. Increased production of aglycosylated variant, in turn, mediated a surprising increase in S100b binding activity compared with the untreated reference bioreactor having greater amounts of fully glycosylated (3-glycan sites occupied) variant. The data disclosed herein demonstrate that glycan site occupancy inhibitors such as, but not limited to, 2-deoxy-D-glucose can be used in a manufacturing process to control the N-linked site occupancy of a recombinant protein in order to manipulate preferred features of the protein that are impacted by glycosylation, such as optimum target/ligand/tissue binding activity, solubility, half life, clearance from serum, among many others. One skilled in the art would appreciate once provided with the disclosure provided herein that control of glycan site occupancy in recombinant proteins using glycan site occupancy inhibitors without need of introducing amino acid mutations to delete the glycosylation sites provides an important new method for controlling protein features rapidly and without the effects on protein conformation, loss of activity, increased immunogenicity, and the like, potentially associated with such mutations.

Example 4

Control of Glycosylation Using 2-deoxy-D-glucose: Decreased Glycan Site Occupancy for an Antibody An antibody that specifically binds human immunoglobulin E was used to determine that the novel cell culture methods of the present invention can be used to produce glycoproteins comprising reduced glycosylation compared with the glycosylation level of the same protein produced under otherwise identical cell culture conditions but in the absence of a glycosylation inhibitor.

As shown on FIGS. 13A through 13D, the fully human anti-IgE antibody designated Antibody 5.948.1 (also referred to herein as "IgE mAb" or mAb 5.948.1"). Antibody 5.948.1 comprises a potential N-linked glycosylation site, i.e., [nts], at amino acid residues 73-75 of the heavy chain polypeptide V domain, and at amino acid residues 301-303, i.e., [NST], of the constant domain (see FIG. 13A). See also International Patent Application No. PCT/US2008/004286 filed Apr. 1, 2008, now published as WO 2008/123999 on Oct. 16, 2008 (incorporated by reference in its entirety herein). FIG. 13A shows the amino acid sequence of the heavy chain (SEQ ID NO:8) with the variable domain residues in lower case letters with the CDRs underlined. The V domain glycosylation site (N2) is capitalized and the constant domain glycosylation site (N301) is underlined. FIG. 13B shows a nucleic acid sequence (SEQ ID NO:9) encoding the amino acid sequence of the heavy chain (SEQ ID NO:8). FIG. 13C shows the amino acid sequence of the light chain (SEQ ID NO:10) with the variable domain residues in lower case letters with the CDRs underlined. FIG. 13D shows a nucleic acid sequence (SEQ ID NO:11) encoding the amino acid sequence of the light chain (SEQ ID NO:10).

Thus, mAb 5.948.1 is a fully human $IgG_2$ comprising a heavy chain comprising two glycosylation sites: Asn73 in framework region 3 (FR3) of the V domain and at Asn301, the canonical Fc heavy chain glycosylation site. FIG. 14 provides a diagram depicting the four possible glycan occupancy site variants for antibody 5.948.1. That is, a 0-glycan occupancy site variant comprising no glycans, a 1-glycan occupancy site variant comprising a glycan at Asn301, a 1-glycan occupancy site variant comprising a glycan at Asn73, and a 2-glycan occupancy variant comprising a glycan at Asn73 and at Asn301. Because each antibody comprises two heavy chains, various permutations are possible comprising various combinations of each of the aforementioned glycan occupancy variants along with two light chains.

Cell cultures expressing mAb 5.948.1 were grown in the presence and absence of 2-deoxy-D-glucose. Briefly, a clonal population of CHO cells expressing the mAb 5.948.1 were seeded into 6×500 mL vented shake flasks at $0.3 \times 10^6$ cells/mL in 100 mL of medium per flask. Shake flasks (S5, S6, S7, S9, S10, S11, see Table 9) containing cells were placed in a non humidified shaking incubator at 36.5° C. with 5% $CO_2$ and an agitation of 140 rpm with a 1 inch throw. Cell counts and viabilities were taken daily for 14 days of culture. Starting on day 3 of culture, all shake flasks were fed with nutrients (16 mL/L/day) and a bolus of glucose (100 g/L glucose stock at 2.5 mL/day). On day 7 and day 9 of culture 1 g/L of 2-deoxy-d-glucose was added to the test shake flasks (S10 and S11, respectively) whereas no 2-deoxy-d-glucose inhibitor was added to the control shake flasks (S6 and S7). On day seven of culture, shake flasks S5 and S9 were harvested for titer determination via HPLC and glycan site occupancy analysis. S9 was harvested before the addition of 2-deoxy-d-glucose. On day twelve of culture, shake flasks S6 (without inhibitor) and S10 (with inhibitor) were harvested for titer determination and glycan site occupancy analysis. On day fourteen of culture, shake flasks S7 (without inhibitor) and S11 (with inhibitor) were harvested for titer determination and glycan site occupancy analysis.

The protein titer was measured for each sample and the results are provided in Table 8. The protein titer increased with time in culture and there was no significant difference in protein titer between cultures without 2-deoxy-D-glucose and cultures comprising the glycosylation inhibitor. Thus, the presence of 2-deoxy-D-glucose did not appear to affect the protein expression by cells grown in the presence of the inhibitor.

TABLE 8

| Sample | Sample ID | 2-deoxy-D-glucose | Titer (mg/ml) |
| --- | --- | --- | --- |
| S5 | S5 day 7 | No | 3.77 |
| S6 | S6 day 12 | No | 4.37 |
| S7 | S7 day 14 | No | 4.92 |
| S9 | S9 day 7 | No | 3.79 |
| S10 | S10 day 12 | Yes | 4.43 |
| S11 | S11 day 14 | yes | 4.61 |

The effect on glycan site occupancy of addition of 2-deoxy-D-glucose was compared with the glycan site occupancy of mAb 5.948.1 produced by cells in the absence of the inhibitor. The glycan profiles for each sample was determined and the chromatograms are shown in FIGS. 16 through 24. The amount of each glycan site occupancy variant in each sample was determined and the results are set forth in Table 9 below.

TABLE 9

| Sample | mAb 5.948.1 Sample ID | 2-Deoxy-D-glucose | mg/ml | Glycan Site Occupancy Profile (%) | | | |
| --- | --- | --- | --- | --- | --- | --- | --- |
| | | | | 0-glycan | 1-glycan-Fc | 1-glycan-Fab | 2-glycan |
| control | control | no | 48.5 | | 1.4 | 0.4 | 98.2 |
| S5 | S5 Day 7 | no | 3.8 | | 1.2 | 0.4 | 98.4 |
| S6 | S6 Day 12 | no | 4.4 | | 2.0 | 0.6 | 97.4 |
| S7 | S7 Day 14 | no | 4.9 | | 4.1 | 0.5 | 95.5 |
| S9 | S9 Day 7 | No | 3.8 | | 1.1 | 0.4 | 98.6 |
| S10 | S10 Day 12 | yes | 4.4 | 0.9 | 3.5 | 1.6 | 94.0 |
| S11 | S11 Day 14 | yes | 4.6 | 1.7 | 5.2 | 2.3 | 90.7 |

More specifically, the glycan profile of a control sample of mAb 5.948.1 produced under conditions providing for maximum glycosylation is shown in FIG. 15. Further, the control demonstrated about 98% 2-glycan, and approximately 2% 1-glycan with no detectable 0-glycan present. Interestingly, of the 1-glycan variant present, most (approximately 75%) was the glycan comprising a saccharide at Asn301, the Fc glycosylation site present in the constant region, with the remaining 25% of the 1-glycan fraction comprising the Asn73 glycan comprising an N-linked glycan in the variable region (antigen binding fragment; Fab).

The glycan profiles of both culture samples taken at day 7(S5 and S9), both without inhibitor were similar to the control. That is, at day seven, the glycan comprised about 98% 2-glycan and about 2% 1-glycan with no detectable 0-glycan variant. Moreover, most of the 1-glycan form was glycosylated at the Fc glycosylation site (Asn301) with the remaining 1-glycan being glycosylated at the variable region.

The glycan profile for the antibody produced in the control culture grown in the absence of inhibitor demonstrated a decrease in the percent of 2-glycan present over time, with the percent of 2-glycan decreasing from about 98% to about 95.5% by day 14. Further, the percent of 1-glycan glycosylated in the Fc region increased from about 1.2% to about 4.1%. However, no 0-glycan was detected at any time in the control culture, and the amount of 1-glycan glycosylated in the Fab did not change over time.

By day 12, the antibody produced in the culture grown in the presence of the inhibitor (S10) demonstrated a shift in the glycan profile. More specifically, the percent of 2-glycan decreased to about 94% and the percent of 1-glycan increased dramatically with increased levels of both 1-glycan glycosylated at the Fab region (1.6%) and 1-glycan glycosylated at the Fc region (3.5%). Even more surprisingly, cells grown in the presence of 2-deoxy-D-glucose produced detectable amounts (0.9%) of 0-glycan variant. Two days later, at day 14, the increase in 1-glycan and 0-glycan variants was even more dramatic and the decrease in the 2-glycan fraction was more pronounced. That is, in S11, the 2-glycan variant comprised about 90% of the antibody produced and the 1-glycan variants comprised 2.3% glycosylated at the Fab region and 5.2% glycosylated at the Fc region. The percent of the antibody having no glycosylation (0-glycan) comprised about 1.7% of antibody 5.948.1 produced.

These results demonstrate that glycosylation of glycoproteins produced in mammalian cell culture can be controlled using a glycosylation inhibitor. More specifically, an antibody comprising two glycosylation sites in the heavy chain produced in cell culture in the presence of 2-deoxy-D-glucose comprised decreasing amounts of 2-glycan variants and increasing amounts of 1-glycan and 0-glycan forms. Without wishing to be bound by any particular theory, it appears that glycosylation in the Fc domain of the antibody occurs preferentially compared with glycosylation at the Fab region of the antibody. Also without wishing to be bound by any particular theory, it may be that the 2-glycan antibody produced in the time before the inhibitor is added to the culture medium remains in present in culture. Thus, the relative decrease in 2-glycan variant present over time with a concomitant increase in 1-glycan and, eventually, 0-glycan, variants likely indicates that very little, if any, additional 2-glycan variant is produced once the inhibitor is added. It may also indicate that while some additional 1-glycan Fc variant continues to be produced, the 1-glycan Fab form is produced once the inhibitor is added. The results also suggest that addition of the inhibitor mediates the production of the 0-glycan aglycosylated variant. Therefore, the data disclosed herein demonstrate, for the first time, that glycosylation of glycoproteins can be controlled, and, even more preferably, without significant decrease in protein titer. The results further suggest that additional modification of culture conditions, including, but not limited to, increasing the length of the culture period, may provide further increase in production of 0- and 1-glycan forms to about or greater than 30% of the glycoprotein produced.

Example 5

Reduced Glycosylation of Anti-IgE Antibody Using 2-deoxy-D-glucose: Decreased Glycan Site Occupancy and Effects on Antibody Binding to IgE Any effect on antigen binding by mAb 5.948.1 mediated by decreased glycan site occupancy is assessed using standard methods such as, but not limited to, those disclosed in WO 2008/123999 (e.g., IgE cell binding assay using RBL-2H3 cells, inhibition of degranulation assay, free IgE depletion from serum, ELISA IgE binding assay, BIAcore™ assay, and the like), and other assays well known in the art for assessing antibody binding characteristics.

More specifically, the binding characteristics of mAb 5.948.1 produced by cells cultured in the absence (S5, S6, and S7) and presence (S9, S10, S11) of 2-deoxy-D-glucose is assessed by BIAcore™ analysis using a BIAcore™ 3000 instrument (BIAcore™, Uppsala, Sweden). Briefly, antibody from each sample is covalently immobilized on a CM5 sensor chip (BIAcore™) using standard EDC-NHS coupling chemistry and an immobilization buffer of 10 mM sodium acetate, ph 5.0. The reference flow cell is activated by EDC-NHS and blocked with ethanolamine but no protein is immobilized thereon.

Kinetic measurements are obtained using HBS-EP buffer (10 mM HEPES, 150 mM NaCl, 3 mM EDTA, 0.005% Surfactant P-20 pH 7.4, supplied by BIAcore™) at a flow rate of 50 or 100 µL/min using an IgE (Serotec, Cat. No. PHP008X2 or Europa Bioproducts, Cat. No. CP1035K) at a concentration ranging from about 0.09 to 600 nM. Injection time for each concentration is approximately 3.25 minutes, followed by 20 minutes dissociation phase. A regeneration step using a regeneration solution (10 mM glycine, pH 1.7) is included after the dissociation phase. Sensorgrams are fitted locally using BIA evaluation software 4.1 (BIAcore™) and Scrubber software version 2.0 (BioLogic Software).

The affinity (KD), on rate (ka, M-1s-1) and off rate (kd) for each sample produced in the absence of inhibitor (S5, S6 and S7) are compared with samples produced in the presence of inhibitor (S9, S10 and S11) to assess the effect(s) of reduced glycosylation on antibody binding of mAb 5.948.1 with its antigen, human IgE.

The nucleic and amino acid sequences described herein are listed below in Table 10 with their sequence identifier numbers.

TABLE 10

SEQUENCES

| SEQ ID NO: | Description |
|---|---|
| 1 | Amino acid sequence of a human sRAGE-Fc fusion protein |
| 2 | Nucleic acid sequence encoding the human sRAGE-Fc fusion protein of SEQ ID NO: 1 |
| 3 | Amino acid sequence of full-length human RAGE |
| 4 | Nucleic acid sequence encoding amino acids 1-251 of human RAGE |
| 5 | Amino acid sequence of tryptic digest T1 of RAGE: pENITAR |
| 6 | Amino acid sequence of tryptic digest T10 of RAGE: VLPNGSFLPAVGIQDEGIFR |
| 7 | Amino acid sequence of tryptic digest T31 of RAGE: EEQYNSTYR |
| 8 | Amino acid sequence of mAb 5.948.1 heavy chain |
| 9 | Nucleic acid sequence encoding heavy chain of mAb 5.948.1 of SEQ ID NO: 8 |
| 10 | Amino acid sequence of mAb 5.948.1 light chain of mAb 5.948.1 |
| 11 | Nucleic acid sequence encoding light chain of mAb 5.948.1 of SEQ ID NO: 10 |
| 12 | Nucleic acid sequence encoding native human RAGE signal sequence: ATGGCAGCCGGAACAGCAGTTGGAGCCTGGGTGCTGGTCCTCAG TCTGTGGGGGCAGTAGTAGGTGCT |
| 13 | Amino acid sequence comprising human RAGE ligand binding site (without 22 amino acid signal): AQNITARI GEPLVLKCKG APKKPPQRLE WK |
| 14 | Amino acid sequence comprising human RAGE ligand binding site (without 23 amino acid signal): QNITARI GEPLVLKCKG APKKPPQRLE WK |
| 15 | Amino acid sequence comprising human RAGE ligand binding site (without 23 amino acid signal and cyclized glutamic acid to pyroglutamic acid): pENITARI GEPLVLKCKG APKKPPQRLE WK |
| 16 | Amino acid sequence comprising human RAGE V-domain (without 22 amino acid signal): AQNITARI GEPLVLKCKG APKKPPQRLE WKLNTGRTEA WKVLSPQGGG PWDSVARVLP NGSLFLPAVG IQDEGIFRCQ |

TABLE 10-continued

SEQUENCES

| SEQ ID NO: | Description |
|---|---|
| | AMNRNGKETK SNYRVR |
| 17 | Amino acid sequence comprising human RAGE V-domain (without 23 amino acid signal): QNITARI GEPLVLKCKG APKKPPQRLE WKLNTGRTEA WKVLSPQGGG PWDSVARVLP NGSLFLPAVG IQDEGIFRCQ AMNRNGKETK SNYRVR |
| 18 | Amino acid sequence comprising human RAGE V-domain (without 23 amino acid signal and cyclized glutamic acid to pyroglutamic acid): pENITARI GEPLVLKCKG APKKPPQRLE WKLNTGRTEA WKVLSPQGGG PWDSVARVLP NGSLFLPAVG IQDEGIFRCQ AMNRNGKETK SNYRVR |
| 19 | Amino acid sequence comprising human interleukin-3 (IL-3) signal sequence: MSRLPVLLLLQLLVRPAMA |
| 20 | Nucleic acid sequence encoding human IL-3 signal sequence of SEQ ID NO: 19: ATGAGCCGCCTGCCCGTCCTGCTCCTGCTCCAACTCCTGGTCCG CCCCGCCATGGCT |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition comprising an amount of a fusion protein, wherein the fusion protein comprises a RAGE polypeptide linked to an immunoglobulin polypeptide,
   a) wherein the RAGE polypeptide comprises a fragment of human RAGE (SEQ ID NO: 3) wherein the fragment of human RAGE comprises a ligand binding site and at least one amino acid residue that may be glycosylated,
   b) wherein the immunoglobulin polypeptide comprises a $C_H2$ domain or a portion of a $C_H2$ domain of an immunoglobulin and a $C_H3$ domain of an immunoglobulin, and
   c) wherein the N-terminal residue of the immunoglobulin polypeptide is linked to the C-terminal residue of the RAGE polypeptide; and
wherein at least 0.5% of the amount of the fusion protein is aglycosylated and wherein no more than 53.2% of the amount of the fusion protein is aglycosylated.

2. The composition of claim 1, wherein at least 30% of the total amount of the fusion protein is aglycosylated.

3. The composition of claim 1, wherein the percentage of the amount of the fusion protein in the fully glycosylated form is less than the percentage of the amount of the fusion protein in all of the non-fully glycosylated forms.

4. The composition of claim 1, wherein the fusion protein comprises at least three amino acid residues that may be glycosylated, wherein a first potential site of glycosylation is an amino acid residue of the RAGE ligand binding site, a second potential site of glycosylation is an amino acid residue of the RAGE polypeptide, and a third potential site of glycosylation is an amino acid residue of the immunoglobulin polypeptide.

5. The composition of claim 1, wherein the RAGE polypeptide comprises a sequence selected from the group consisting of SEQ ID NO:13, SEQ ID NO:14, and SEQ ID NO:15.

6. The composition of claim 1, wherein the RAGE polypeptide comprises a sequence selected from the group consisting of SEQ ID NO:16, SEQ ID NO:17, and SEQ ID NO:18.

7. A pharmaceutical composition comprising the composition of claim 1 and a pharmaceutically acceptable carrier.

8. A pharmaceutical composition comprising the composition of claim 2 and a pharmaceutically acceptable carrier.

9. A pharmaceutical composition comprising the composition of claim 3 and a pharmaceutically acceptable carrier.

10. A pharmaceutical composition comprising the composition of claim 4 and a pharmaceutically acceptable carrier.

11. A pharmaceutical composition comprising the composition of claim 5 and a pharmaceutically acceptable carrier.

12. A pharmaceutical composition comprising the composition of claim 6 and a pharmaceutically acceptable carrier.

13. A composition comprising an amount of a fusion protein, wherein the fusion protein comprises the amino acid sequence of SEQ ID NO:1 without the signal sequence which comprises from amino acid residue 1 through amino acid residue number 23 or from amino acid residue 1 through amino acid residue number 22, wherein said fusion protein lacks the terminal lysine residue (Lys438), and further wherein at least 0.5% of the amount of the fusion protein is aglycosylated and wherein no more than 53.2% of the amount of the fusion protein is aglycosylated.

14. A pharmaceutical composition comprising the composition of claim 13 and a pharmaceutically acceptable carrier.

* * * * *

SEQUENCE LISTING

```
<160> NUMBER OF SEQ ID NOS: 20

<210> SEQ ID NO 1
<211> LENGTH: 461
<212> TYPE: PRT
<213> ORGANISM: Artificial Sequence
<220> FEATURE:
<223> OTHER INFORMATION: human soluble RAGE fused to human Fc domain

<400> SEQUENCE: 1

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
                20                  25                  30

Pro Leu Val Leu Lys Cys Lys Gly Ala Pro Lys Lys Pro Pro Gln Arg
            35                  40                  45

Leu Glu Trp Lys Leu Asn Thr Gly Arg Thr Glu Ala Trp Lys Val Leu
        50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Pro Gly Gly Asp Pro Arg Pro Thr Phe Ser Cys
```

```
                195                 200                 205
Ser Phe Ser Pro Gly Leu Pro Arg His Arg Ala Leu Arg Thr Ala Pro
    210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Val Asp Val Ser His Glu Asp Pro Glu Val Lys
        275                 280                 285
Phe Asn Trp Tyr Val Asp Gly Val Glu Val His Asn Ala Lys Thr Lys
    290                 295                 300
Pro Arg Glu Glu Gln Tyr Asn Ser Thr Tyr Arg Val Val Ser Val Leu
305                 310                 315                 320
Thr Val Leu His Gln Asp Trp Leu Asn Gly Lys Glu Tyr Lys Cys Lys
                325                 330                 335
Val Ser Asn Lys Ala Leu Pro Ala Pro Ile Glu Lys Thr Ile Ser Lys
            340                 345                 350
Ala Lys Gly Gln Pro Arg Glu Pro Gln Val Tyr Thr Leu Pro Pro Ser
        355                 360                 365
Arg Asp Glu Leu Thr Lys Asn Gln Val Ser Leu Thr Cys Leu Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Pro Phe Phe Leu Tyr Ser Lys Leu Thr Val Asp Lys Ser Arg Trp Gln
            420                 425                 430
Gln Gly Asn Val Phe Ser Cys Ser Val Met His Glu Ala Leu His Asn
        435                 440                 445
His Tyr Thr Gln Lys Ser Leu Ser Leu Ser Pro Gly Lys
    450                 455                 460

<210> SEQ ID NO 2
<211> LENGTH: 1386
<212> TYPE: DNA
<213> ORGANISM: Artificial Sequence
<220> FEATURE:
<223> OTHER INFORMATION: human soluble RAGE fused to human Fc domain

<400> SEQUENCE: 2
atggcagccg gaacagcagt tggagcctgg gtgctggtcc tcagtctgtg gggggcagta      60
gtaggtgctc aaaacatcac agcccggatt ggcgagccac tggtgctgaa gtgtaagggg     120
gcccccaaga accaccccca gcggctggaa tggaaactga cacaggccg acagaagct      180 tggaaggtcc tgtctcccca gggaggaggc ccctgggaca gtgtggctcg tgtccttccc     240
aacggctccc tcttccttcc ggctgtcggg atccaggatg aggggatttt ccggtgccag     300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga ggggagctac cctgcaggga ctcttagctg cacttggat      480 gggaagcccc tggtgcctaa tgagaaggga gtatctgtga ggaacagac caggagacac     540 cctgagacag ggctcttcac actgcagtcg gagctaatgg tgaccccagc ccggggagga     600
```

```
gatccccgtc caccttctc ctgtagcttc agcccaggcc ttccccgaca ccgggccttg    660
cgcacagccc ccatccagcc ccgtgtctgg gagcctgtgc ctctggagga ggtccaattg    720
gtggtggagc cagaaggtgg agcagtagct cctccgtcag tcttcctctt ccccccaaaa    780
cccaaggaca ccctcatgat ctcccggacc cctgaggtca catgcgtggt ggtggacgtg    840
agccacgaag accctgaggt caagttcaac tggtacgtgg acggcgtgga ggtgcataat    900
gccaagacaa agccgcggga ggagcagtac aacagcacgt accgtgtggt cagcgtcctc    960
accgtcctgc accaggactg gctgaatggc aaggagtaca agtgcaaggt ctccaacaaa    1020 gcctcccag ccccatcga gaaaaccatc tccaaagcca agggcagcc ccgagaacca    1080 caggtgtaca ccctgccccc atcccgggat gagctgacca gaaccaggt cagcctgacc    1140 tgcctggtca aaggcttcta tcccagcgac atcgccgtgg agtgggagag caatgggcag    1200
ccggagaaca actacaagac cacgcctccc gtgctggact ccgacggctc cttcttcctc    1260
tacagcaagc tcaccgtgga caagagcagg tggcagcagg ggaacgtctt ctcatgctcc    1320
gtgatgcatg aggctctgca caaccactac acgcagaaga gcctctccct gtctccgggt    1380
aaatga                                                               1386

<210> SEQ ID NO 3
<211> LENGTH: 404
<212> TYPE: PRT
<213> ORGANISM: Homo sapiens

<400> SEQUENCE: 3

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220
```

```
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
        275                 280                 285
Pro Glu Ile Gly Pro Gln Asp Gln Gly Thr Tyr Ser Cys Val Ala Thr
290                 295                 300
His Ser Ser His Gly Pro Gln Glu Ser Arg Ala Val Ser Ile Ser Ile
305                 310                 315                 320
Ile Glu Pro Gly Glu Glu Gly Pro Thr Ala Gly Ser Val Gly Gly Ser
                325                 330                 335
Gly Leu Gly Thr Leu Ala Leu Ala Leu Gly Ile Leu Gly Gly Leu Gly
            340                 345                 350
Thr Ala Ala Leu Leu Ile Gly Val Ile Leu Trp Gln Arg Arg Gln Arg
        355                 360                 365
Arg Gly Glu Glu Arg Lys Ala Pro Glu Asn Gln Glu Glu Glu Glu Glu
370                 375                 380
Arg Ala Glu Leu Asn Gln Ser Glu Glu Pro Glu Ala Gly Glu Ser Ser
385                 390                 395                 400

Thr Gly Gly Pro

<210> SEQ ID NO 4
<211> LENGTH: 753
<212> TYPE: DNA
<213> ORGANISM: Homo sapiens

<400> SEQUENCE: 4
atggcagccg aacagcagt tggagcctgg gtgctggtcc tcagtctgtg gggggcagta      60
gtaggtgctc aaaacatcac agcccggatt ggcgagccac tggtgctgaa gtgtaagggg    120
gcccccaaga accacccca gcggctggaa tggaaactga acacaggccg acagaagct     180 tggaaggtcc tgtctcccca gggaggaggc ccctgggaca gtgtggctcg tgtccttccc    240
aacggctccc tcttccttcc ggctgtcggg atccaggatg aggggatttt ccggtgccag    300
gcaatgaaca ggaatggaaa ggagaccaag tccaactacc gagtccgtgt ctaccagatt    360
cctgggaagc cagaaattgt agattctgcc tctgaactca cggctggtgt tcccaataag    420
gtggggacat gtgtgtcaga ggggagctac cctgcaggga ctcttagctg cacttggat     480 gggaagcccc tggtgcctaa tgagaaggga gtatctgtga aggaacagac caggagacac    540
cctgagacag ggctcttcac actgcagtcg gagctaatgg tgaccccagc ccggggagga    600
gatccccgtc ccaccttctc ctgtagcttc agcccaggcc ttccccgaca ccgggccttg    660
cgcacagccc ccatccagcc ccgtgtctgg gagcctgtgc ctctggagga ggtccaattg    720
gtggtggagc cagaaggtgg agcagtagct cct                                 753

<210> SEQ ID NO 5
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glutamic Acid is modified to be Pyroglutamic
      Acid (PyroGlu also pE)
```

<400> SEQUENCE: 5

Glu Asn Ile Thr Ala Arg
1               5

<210> SEQ ID NO 6
<211> LENGTH: 20
<212> TYPE: PRT
<213> ORGANISM: Homo sapiens

<400> SEQUENCE: 6

Val Leu Pro Asn Gly Ser Phe Leu Pro Ala Val Gly Ile Gln Asp Glu
1               5                   10                  15

Gly Ile Phe Arg
            20

<210> SEQ ID NO 7
<211> LENGTH: 9
<212> TYPE: PRT
<213> ORGANISM: Homo sapiens

<400> SEQUENCE: 7

Glu Glu Gln Tyr Asn Ser Thr Tyr Arg
1               5

<210> SEQ ID NO 8
<211> LENGTH: 451
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Tyr Asp Ser Asp Gly Tyr Tyr Ser Phe Ser Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu

```
                  210               215               220
Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 9
<211> LENGTH: 1342
<212> TYPE: DNA
<213> ORGANISM: Homo sapiens

<400> SEQUENCE: 9
caggtgcagc tggtgcagtc tggggctgag gtgaagaagc ctggggcctc agtgaaggtc     60
tcctgcaagg cttctggata caccttcacc agttatgata tcaactgggt gcgacaggcc    120
actggacaag gcttgagtg gatgggatgg atggacccta acagtggtaa cacaggctat    180
gcacagaagt tccagggcag agtcaccatg accaggaaca cctccataag cacagcctac    240
atggagctga gcagcctgag atctgaggac acggccgtgt attactgtgc gagaggccac    300
tatgatagtg atggttatta ctccttctcc ggtatggacg tctggggcca agggaccacg    360
gtcaccgtct cctcacctcc accaacccat ctcttccccc tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca acaccaaggt ggacaagaca    660
gttgagcgca aatgttgtgt cgagtgccca ccgtgcccag caccacctgt ggcaggaccg    720
```

-continued

| | |
|---|---|
| tcagtcttcc tcttcccccc aaacccaag gacaccctca tgatctcccg gaccctgag | 780 |
| gtcacgtgcg tggtggtgga cgtgagccac gaagacccg aggtccagtt caactggtac | 840 |
| gtggacggcg tggaggtgca taatgccaag acaaagccac gggaggagca gttcaacagc | 900 |
| acgttccgtg tggtcagcgt cctcaccgtt gtgcaccagg actggctgaa cggcaaggag | 960 |
| tacaagtgca aggtctccaa caaaggcctc ccagccccca tcgagaaaac catctccaaa | 1020 |
| accaaagggc agccccgaga accacaggtg tacaccctgc ccccatcccg ggaggagatg | 1080 |
| accaagaacc aggtcagcct gacctgcctg gtcaaaggct tctaccccag cgacatcgcc | 1140 |
| gtggagtggg agagcaatgg gcagccggag aacaactaca agaccacacc tcccatgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gg | 1342 |

<210> SEQ ID NO 10
<211> LENGTH: 220
<212> TYPE: PRT
<213> ORGANISM: Homo sapiens

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Ala Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 11
<211> LENGTH: 660
<212> TYPE: DNA
<213> ORGANISM: Homo sapiens

<400> SEQUENCE: 11

```
gatattgtga tgactcagtc tccactctcc ctgcccgtca ccctggaga gccggcctcc    60 atctcctgta ggtctagtca gagcctcctg cataggaatg gatacaacta cttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ccggccactt tcggcggagg gaccaaggtg gagatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc   600 gaagtcaccc atcagggcct gagctcgccc gtcacaaaga gcttcaacag gggagagtgt   660
```

<210> SEQ ID NO 12
<211> LENGTH: 69
<212> TYPE: DNA
<213> ORGANISM: Homo sapiens

<400> SEQUENCE: 12

```
atggcagccg aacagcagt tggagcctgg gtgctggtcc tcagtctgtg gggggcagta    60
gtaggtgct                                                            69
```

<210> SEQ ID NO 13
<211> LENGTH: 30
<212> TYPE: PRT
<213> ORGANISM: Homo sapiens

<400> SEQUENCE: 13

Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys
            20                  25                  30

<210> SEQ ID NO 14
<211> LENGTH: 29
<212> TYPE: PRT
<213> ORGANISM: Homo sapiens

<400> SEQUENCE: 14

Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys
            20                  25

<210> SEQ ID NO 15
<211> LENGTH: 29
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glutamic Acid modified to be Pyroglutamic Acid
      (PyroGlu also pE)

<400> SEQUENCE: 15

Glu Asn Ile Thr Ala Arg Ile Gly Glu Pro Leu Val Leu Lys Cys Lys
1               5                   10                  15

```
Gly Ala Pro Lys Lys Pro Pro Gln Arg Leu Glu Trp Lys
            20                  25
```

<210> SEQ ID NO 16
<211> LENGTH: 94
<212> TYPE: PRT
<213> ORGANISM: Homo sapiens

<400> SEQUENCE: 16

```
Ala Gln Asn Ile Thr Ala Arg Ile Gly Glu Pro Leu Val Leu Lys Cys
1               5                   10                  15

Lys Gly Ala Pro Lys Lys Pro Pro Gln Arg Leu Glu Trp Lys Leu Asn
            20                  25                  30

Thr Gly Arg Thr Glu Ala Trp Lys Val Leu Ser Pro Gln Gly Gly Gly
        35                  40                  45

Pro Trp Asp Ser Val Ala Arg Val Leu Pro Asn Gly Ser Leu Phe Leu
    50                  55                  60

Pro Ala Val Gly Ile Gln Asp Glu Gly Ile Phe Arg Cys Gln Ala Met
65                  70                  75                  80

Asn Arg Asn Gly Lys Glu Thr Lys Ser Asn Tyr Arg Val Arg
                85                  90
```

<210> SEQ ID NO 17
<211> LENGTH: 93
<212> TYPE: PRT
<213> ORGANISM: Homo sapiens

<400> SEQUENCE: 17

```
Gln Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60

Ala Val Gly Ile Gln Asp Glu Gly Ile Phe Arg Cys Gln Ala Met Asn
65                  70                  75                  80

Arg Asn Gly Lys Glu Thr Lys Ser Asn Tyr Arg Val Arg
                85                  90
```

<210> SEQ ID NO 18
<211> LENGTH: 93
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glutamic Acid is modified to be Pyroglutamic
      Acid (PyroGlu also pE)

<400> SEQUENCE: 18

```
Glu Asn Ile Thr Ala Arg Ile Gly Glu Pro Leu Val Leu Lys Cys Lys
1               5                   10                  15

Gly Ala Pro Lys Lys Pro Pro Gln Arg Leu Glu Trp Lys Leu Asn Thr
            20                  25                  30

Gly Arg Thr Glu Ala Trp Lys Val Leu Ser Pro Gln Gly Gly Gly Pro
        35                  40                  45

Trp Asp Ser Val Ala Arg Val Leu Pro Asn Gly Ser Leu Phe Leu Pro
    50                  55                  60
```

```
Ala Val Gly Ile Gln Asp Glu Gly Ile Phe Arg Cys Gln Ala Met Asn
 65                  70                  75                  80

Arg Asn Gly Lys Glu Thr Lys Ser Asn Tyr Arg Val Arg
                 85                  90

<210> SEQ ID NO 19
<211> LENGTH: 19
<212> TYPE: PRT
<213> ORGANISM: Homo sapiens

<400> SEQUENCE: 19

Met Ser Arg Leu Pro Val Leu Leu Leu Gln Leu Leu Val Arg Pro
  1               5                  10                  15

Ala Met Ala

<210> SEQ ID NO 20
<211> LENGTH: 57
<212> TYPE: DNA
<213> ORGANISM: Homo sapiens

<400> SEQUENCE: 20
atgagccgcc tgcccgtcct gctcctgctc caactcctgg tccgccccgc catggct      57
```